United States Patent
Cerione et al.

(12) 
(10) Patent No.: US 10,767,212 B2
(45) Date of Patent: Sep. 8, 2020

(54) METHOD OF SCREENING COMPOUNDS

(71) Applicant: Cornell University, Ithaca, NY (US)

(72) Inventors: Richard Cerione, Ithaca, NY (US);
Jon W Erickson, Freeville, NY (US);
Clint A Stalnecker, Chapel Hill, NC (US)

(73) Assignee: Cornell University, Ithaca, NY (US)

( * ) Notice: Subject to any disclaimer, the term of this patent is extended or adjusted under 35 U.S.C. 154(b) by 0 days.

(21) Appl. No.: 15/714,885

(22) Filed: Sep. 25, 2017

(65) Prior Publication Data

US 2018/0100178 A1    Apr. 12, 2018

Related U.S. Application Data

(60) Provisional application No. 62/399,074, filed on Sep. 23, 2016.

(51) Int. Cl.
*C12N 11/02* (2006.01)
*C12Q 1/34* (2006.01)
*C12N 9/80* (2006.01)

(52) U.S. Cl.
CPC .............. *C12Q 1/34* (2013.01); *C12N 9/80* (2013.01); *C12Y 305/01002* (2013.01); *G01N 2500/04* (2013.01); *G01N 2500/20* (2013.01)

(58) Field of Classification Search
None
See application file for complete search history.

(56) References Cited

U.S. PATENT DOCUMENTS

| | | | | |
|---|---|---|---|---|
| 2012/0220610 A1* | 8/2012 | Cerione | ................ | A61K 31/00 514/270 |
| 2013/0252983 A1* | 9/2013 | Cerione | ............ | G01N 33/5011 514/270 |

OTHER PUBLICATIONS

Stalnecker et al., "Conformational Changes in the Activation Loop of Mitochondrial Glutaminase C: A Direct Fluorescence Readout That Distinguishes the Binding of Allosteric Inhibitors from Activators," J. Biol. Chem. 292 (15):6095-107 (2017).

* cited by examiner

*Primary Examiner* — Hope A Robinson
(74) *Attorney, Agent, or Firm* — Troutman Pepper Hamilton Sanders LLP (Rochester)

(57) ABSTRACT

The present technology relates to kidney-type glutaminase (GLS) proteins that have a phenylalanine to tryptophan substitution at the position corresponding to residue 322 of human glutaminase C (GAC), and methods of using such proteins to screen for compounds that bind to the activation loop of GLS and/or modulate glutaminase activity of GLS.

9 Claims, 14 Drawing Sheets

Specification includes a Sequence Listing.

Figures 2A–B

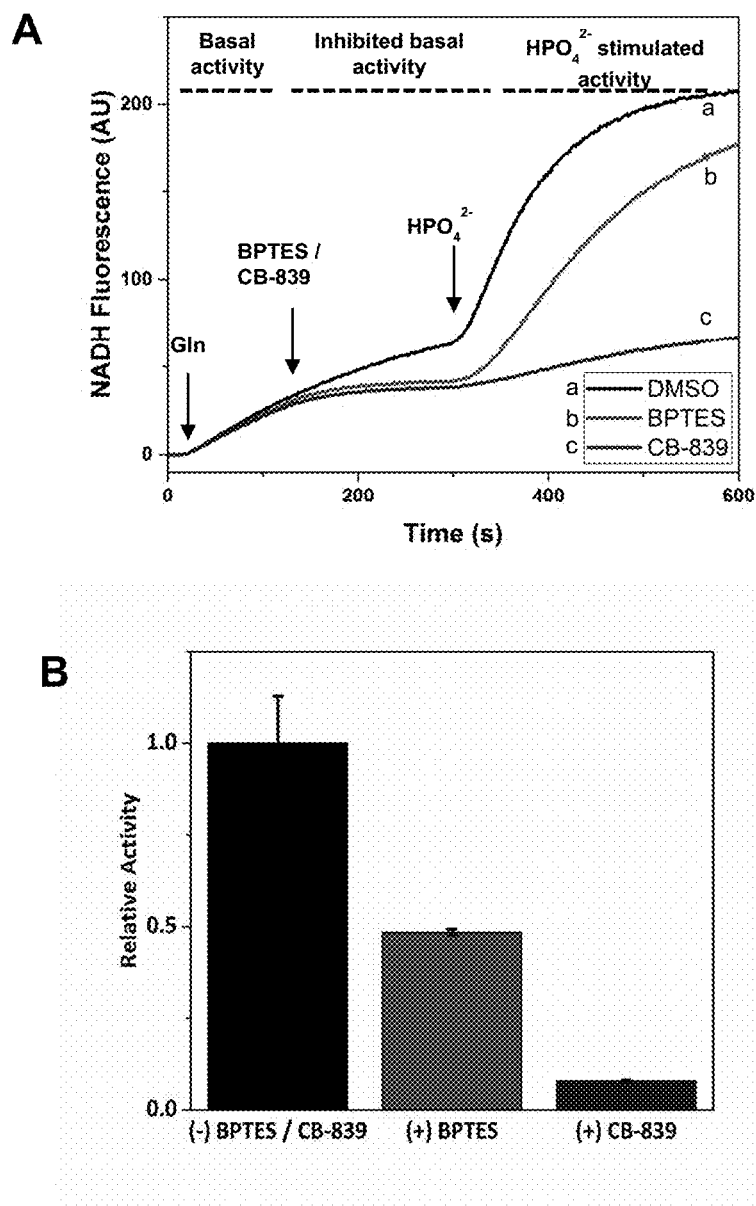
Figures 4A–B

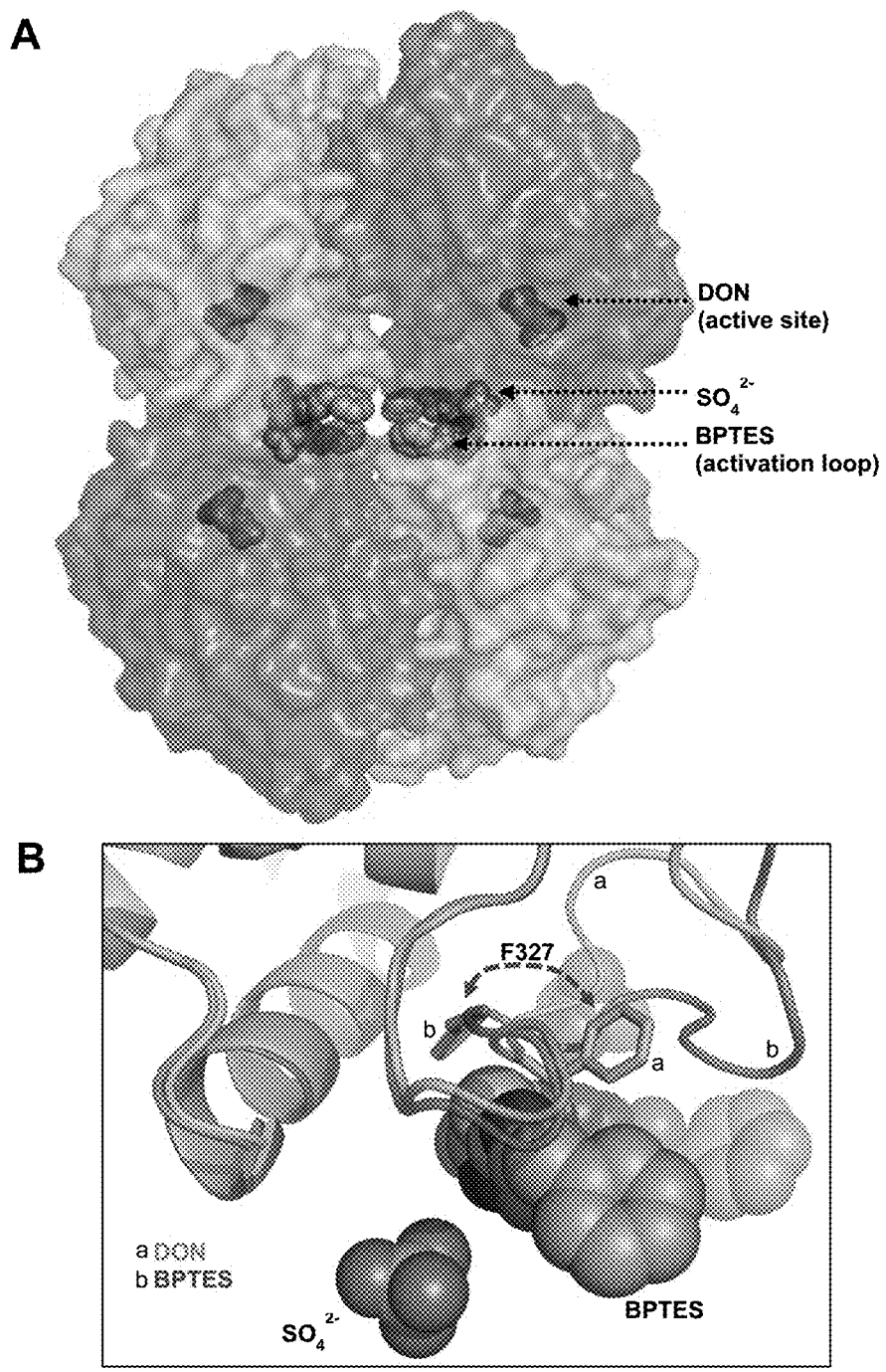
Figures 5A–B

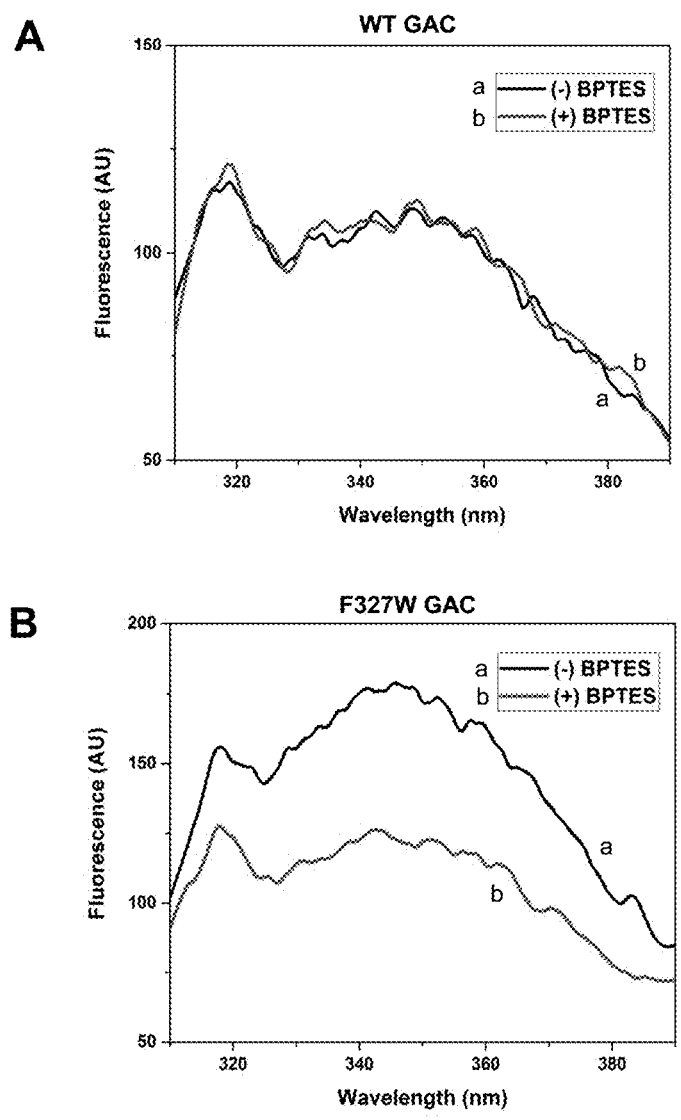
Figures 6A–B

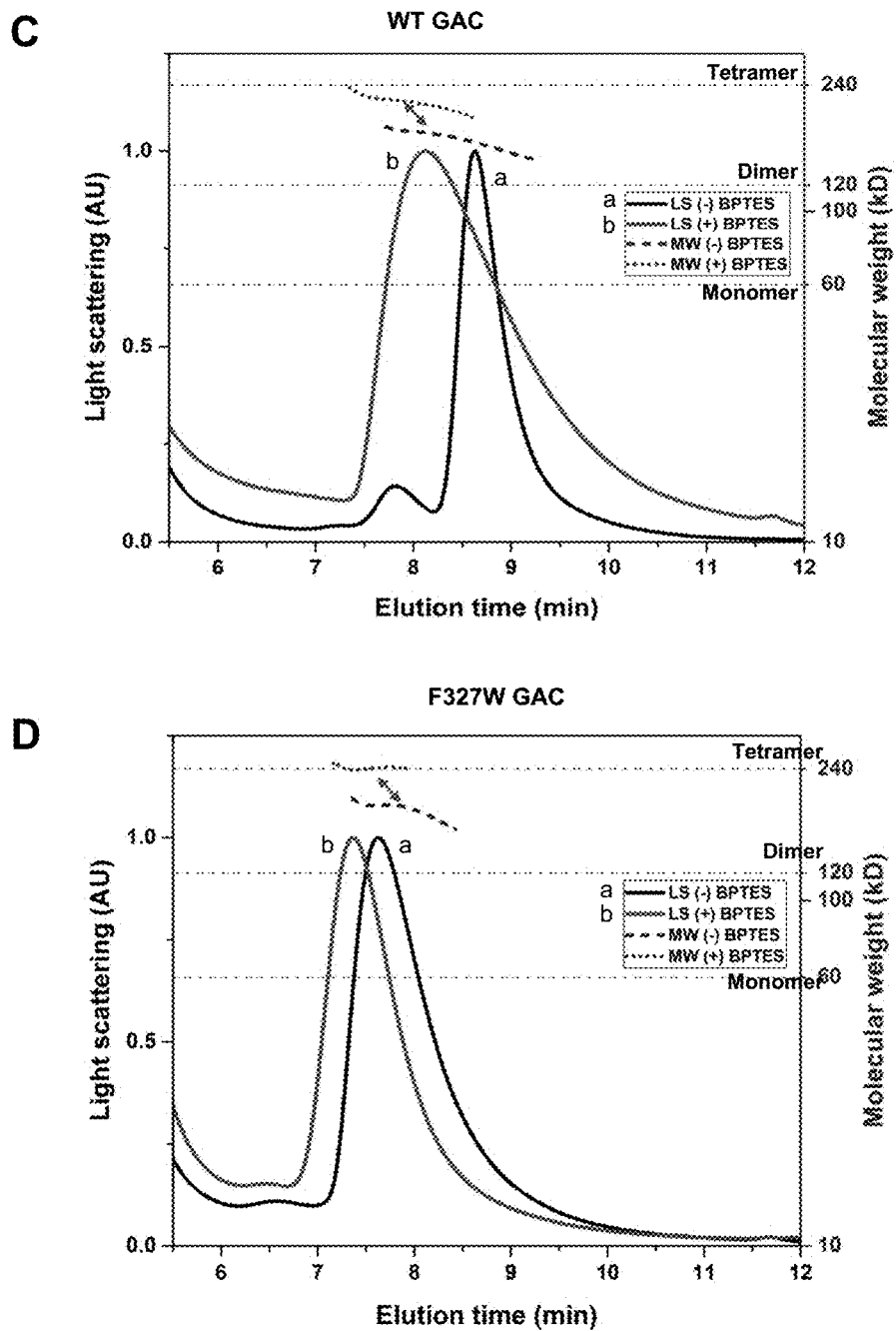
Figures 6C–D

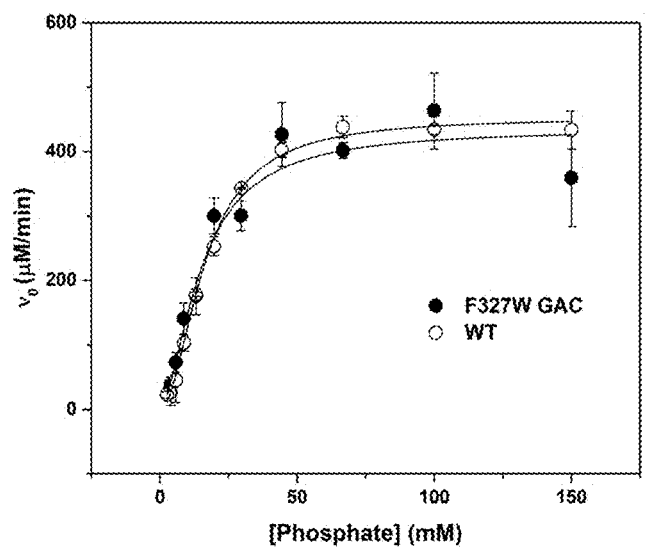
Figure 6E
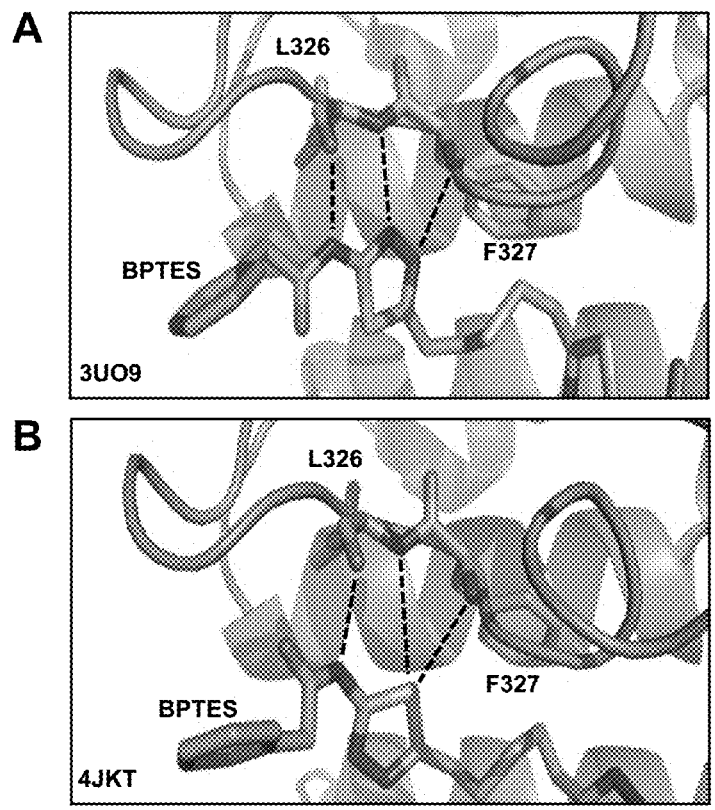
Figures 7A–B

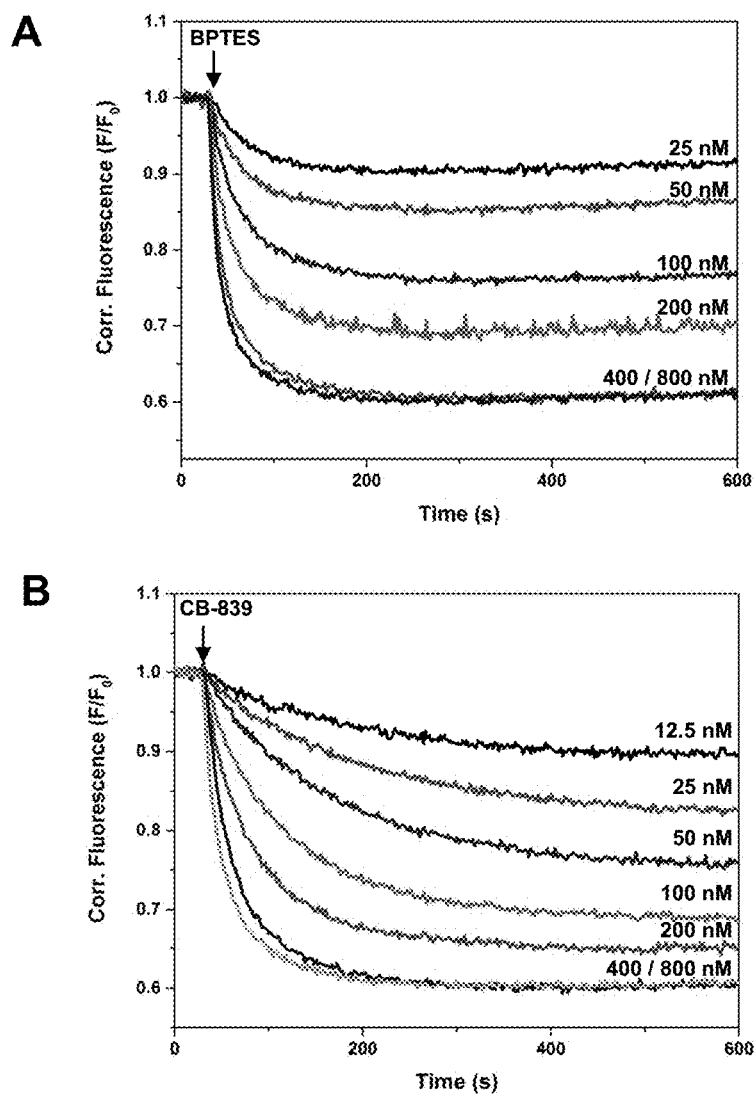
Figures 8A–B

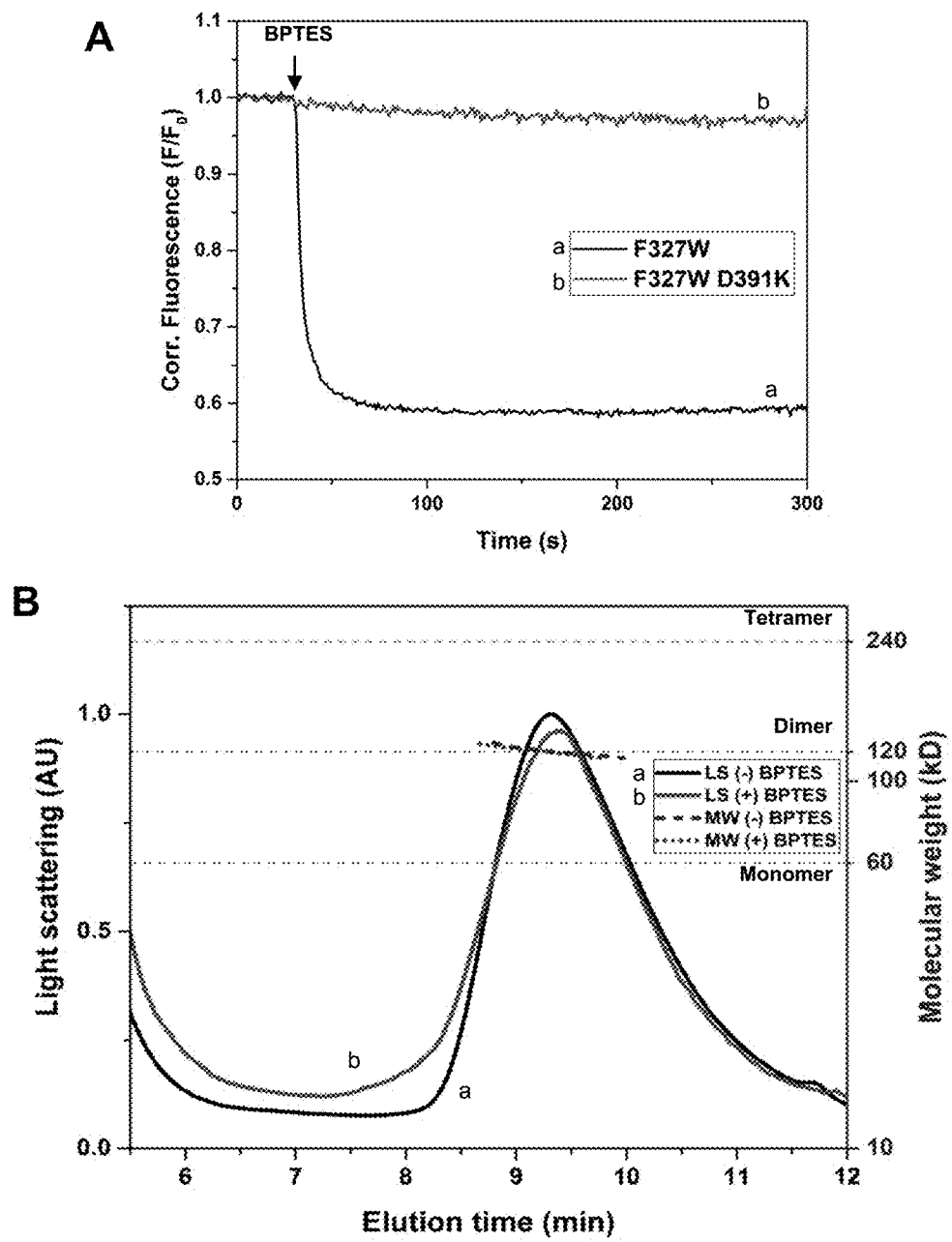
Figures 9A–B

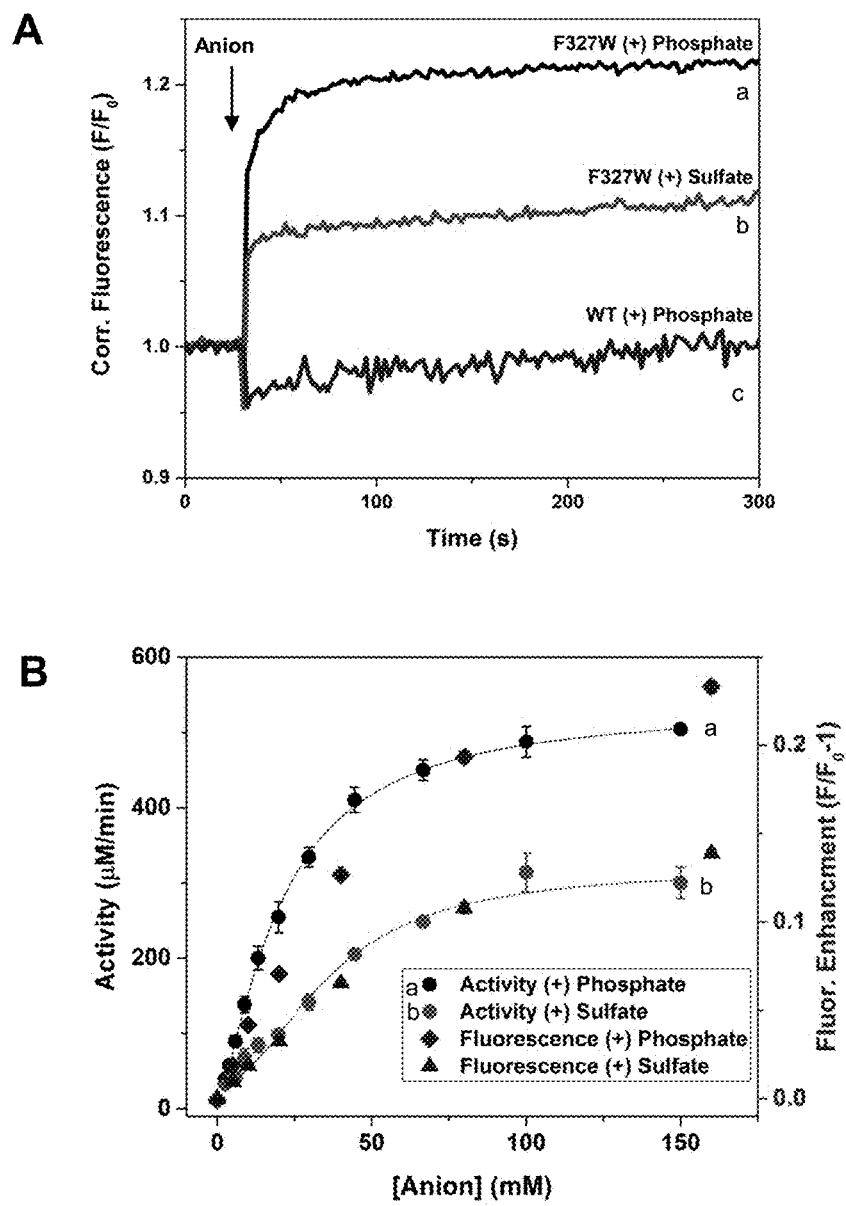
Figures 10A–B

METHOD OF SCREENING COMPOUNDS

This application claims the priority benefit of U.S. Provisional Patent Application Ser. No. 62/399,074, filed Sep. 23, 2016, which is hereby incorporated by reference in its entirety.

This invention was made with government support under R01GM040654 and R01GM047458 awarded by National Institutes of Health. The government has certain rights in the invention.

FIELD OF THE INVENTION

This invention is directed generally to mutant GLS proteins and methods of using them to screen for compounds that bind to and/or modulate GLS.

BACKGROUND OF THE INVENTION

The increased reliance on glutamine catabolism by proliferating cancer cells, termed glutamine addiction, has recently attracted significant attention as a route to developing new therapeutics that target this unique metabolic requirement of transformed cells (Hensley et al., "Glutamine and Cancer: Cell Biology, Physiology, and Clinical Opportunities," *J. Clin. Invest.* 123:3678-84 (2013); DeBerardinis & Cheng, "Q's Next: The Diverse Functions of Glutamine in Metabolism, Cell Biology and Cancer," *Oncogene* 29:313-24 (2010); Krall & Christofk, "Rethinking Glutamine Addiction," *Nat. Cell Biol.* 17:1515-17 (2015); DeBerardinis et al., "The Biology of Cancer: Metabolic Reprogramming Fuels Cell Growth and Proliferation," *Cell Metab.* 7:11-20 (2008)). The outcome of elevated glutamine metabolism leads to increases in glutamine-fueled anaplerosis, where glutamine is first deamidated by the mitochondrial enzyme glutaminase to produce stoichiometric amounts of glutamate and ammonia. Glutamate is then deamidated by glutamate dehydrogenase (GDH) or by one of two transaminases (GOT/GPT), producing α-ketoglutarate, which is incorporated into the TCA cycle. In this way, glutamine, being the most abundant amino acid in the blood, acts as a primary carbon and nitrogen source for highly proliferative cells. Increased glutamine metabolism is triggered by several signal transduction pathways, including those influenced by HIF1α, Myc, and Rho GTPases, as well as by Ras/MAPK- and mechanistic target of rapamycin (mTOR)/Akt-signaling activities (Sun & Denko, "Hypoxic Regulation of Glutamine Metabolism Through HIF1 and SIAH2 Supports Lipid Synthesis That Is Necessary for Tumor Growth," *Cell Metab.* 19:285-92 (2014); Wise et al., "Hypoxia Promotes Isocitrate Dehydrogenase-Dependent Carboxylation of α-Ketoglutarate to Citrate to Support Cell Growth and Viability," *Proc. Natl. Acad. Sci. U.S.A.* 108: 19611-16 (2011); Gao et al., "c-Myc Suppression of miR-23a/b Enhances Mitochondrial Glutaminase Expression and Glutamine Metabolism," *Nature* 458:762-65 (2009); Wise et al., "Myc Regulates a Transcriptional Program That Stimulates Mitochondrial Glutaminolysis and Leads to Glutamine Addiction," *Proc. Natl. Acad. Sci. U.S.A.* 105:18782-87 (2008); Wang et al., "Targeting Mitochondrial Glutaminase Activity Inhibits Oncogenic Transformation," *Cancer Cell* 18:207-19 (2010); Stalnecker et al., "Mechanism by Which a Recently Discovered Allosteric Inhibitor Blocks Glutamine Metabolism in Transformed Cells," *Proc. Natl. Acad. Sci. U.S.A.* 112:394-99 (2015); Thangavelu et al., "Structural Basis for the Allosteric Inhibitory Mechanism of Human Kidney-Type Glutaminase (KGA) and Its Regulation by Raf-Mek-Erk Signaling in Cancer Cell Metabolism," *Proc. Natl. Acad. Sci. U.S.A.* 109:7705-10 (2012); Duran et al., "Glutaminolysis Activates Rag-mTORC1 Signaling," *Mol. Cell* 47:349-58 (2012); Csibi et al., "The mTORC1/S6K1 Pathway Regulates Glutamine Metabolism Through the eIF4B-Dependent Control of c-Myc Translation," *Curr. Biol.* 24:2274-80 (2014)).

Glutaminases are encoded by two different genes: GLS1, which encodes kidney-type glutaminase (GLS), and GLS2, which encodes liver-type glutaminase. There are also two isoforms of GLS: one that is commonly referred to as kidney-type glutaminase (KGA) and the other, a C-terminal splice variant, designated glutaminase C (GAC). Because GAC is often highly expressed in cancer cells, it has been described as a "gate-keeper" enzyme for the elevated glutamine metabolism exhibited by these cells ("glutamine addiction"). Thus, GAC, as well as the longer GLS isoform KGA, are attractive therapeutic targets (Lukey et al., "Therapeutic Strategies Impacting Cancer Cell Glutamine Metabolism," *Future Med. Chem.* 5:1685-700 (2013); van den Heuvel et al., "Analysis of Glutamine Dependency in Non-Small Cell Lung Cancer," *Cancer Biol. Ther.* 13:1185-94 (2012)).

Currently, there are three classes of inhibitors for KGA and GAC. One class is represented by the benzophenanthridines, and, specifically, compound 968, which was previously demonstrated to act as a non-competitive allosteric inhibitor of GAC by interfering with its ability to undergo normal monomer-monomer interactions that lead to GAC dimers and, ultimately, to activated tetramers (Wang et al., "Targeting Mitochondrial Glutaminase Activity Inhibits Oncogenic Transformation," *Cancer Cell* 18:207-19 (2010); Stalnecker et al., "Mechanism by Which a Recently Discovered Allosteric Inhibitor Blocks Glutamine Metabolism in Transformed Cells," *Proc. Natl. Acad. Sci. U.S.A.* 112: 394-99 (2015); Katt et al., "Dibenzophenanthridines as Inhibitors of Glutaminase C and Cancer Cell Proliferation," *Mol. Cancer Ther.* 11:1269-78 (2012)). A second class of KGA/GAC inhibitors consists of analogs of the substrate glutamine, such as diazo-O-norleucine (DON), which binds to the enzyme active site and covalently modifies the catalytic serine (Ser-291) (Thangavelu et al., "Structural Basis for the Active Site Inhibition Mechanism of Human Kidney-Type Glutaminase (KGA)," *Sci. Rep.* 4:3827 (2014)). The third class of inhibitors, depicted in FIG. 1, consists of a number of bisthiadiazole derivatives, the prototype being bis-2-(5-phenylacetamido-1,2,4-thiadiazol-2-yl)ethyl (BPTES) (Thangavelu et al., "Structural Basis for the Allosteric Inhibitory Mechanism of Human Kidney-Type Glutaminase (KGA) and Its Regulation by Raf-Mek-Erk Signaling in Cancer Cell Metabolism," *Proc. Natl. Acad. Sci. U.S.A.* 109:7705-10 (2012); Robinson et al., "Novel Mechanism of Inhibition of Rat Kidney-Type Glutaminase by Bis-2-(5-Phenylacetamido-1,2,4-Thiadiazol-2-yl)Ethyl Sulfide (BPTES)," *Biochem. J.* 406:407-14 (2007); Hartwick & Curthoys, "BPTES Inhibition of hGA124-551, a Truncated Form of Human Kidney-Type Glutaminase," *J. Enzyme Inhib. Med. Chem.* 27:861-67 (2012); DeLaBarre et al., "Full-Length Human Glutaminase in Complex with an Allosteric Inhibitor," *Biochemistry* 50:10764-70 (2011); Cassago et al., "Mitochondrial Localization and Structure-Based Phosphate Activation Mechanism of Glutaminase C with Implications for Cancer Metabolism," *Proc. Natl. Acad. Sci. U.S.A.* 109:1092-97 (2012)). Gross et al. (Gross et al., "Antitumor Activity of the Glutaminase Inhibitor CB-839 in Triple-Negative Breast Cancer," *Mol. Cancer Ther.* 13:890-901 (2014)) have described a BPTES derivative, CB-839, which is a more potent inhibitor than BPTES, and showed it to be effective against triple-negative breast cancer cells. CB-839 efficacy has been examined in vivo and subsequently tested in clinical trials (Matre et al., "Efficacy of Novel Glutaminase Inhibitor CB-839 in Acute Myeloid Leukemia," Blood 124:3763 (2014)).

The discovery of BPTES as an inhibitor of KGA/GAC activity was first reported by Robinson et al. (Robinson et al., "Novel Mechanism of Inhibition of Rat Kidney-Type Glutaminase by Bis-2-(5-Phenylacetamido-1,2,4-Thiadiazol-2-yl)Ethyl Sulfide (BPTES)," Biochem. J. 406:407-14 (2007)). Elucidation of the binding site of BPTES, based on the X-ray crystal structure solved for the inhibitor bound to the KGA/GAC enzymes, revealed that its interactions with a flexible loop within the dimer-dimer interface of the tetrameric forms of these enzymes (i.e., the "activation loop"), accounted for its mode of inhibition. Indeed, mutations along this loop ($^{316}$KEPSGLRFNKLF$^{327}$ (SEQ ID NO:1); unless expressly stated otherwise, the amino acid numbering used in this application is in reference to mouse GAC) can markedly impact enzyme activity. The functional consequences of these mutations vary from inducing constitutive activation in the absence of phosphate (K325A), to shifting the dose response for phosphate (F322Y/F327S, K316A), to inhibiting the formation of higher-order oligomers (K316Q) (DeLaBarre et al., "Full-Length Human Glutaminase in Complex with an Allosteric Inhibitor," Biochemistry 50:10764-70 (2011); McDonald et al., "Effect of Lysine to Alanine Mutations on the Phosphate Activation and BPTES Inhibition of Glutaminase," Neurochem. Int 88:10-14 (2015); Ferreira et al., "Active Glutaminase C Self-Assembles into a Supratetrameric Oligomer That Can Be Disrupted by an Allosteric Inhibitor," J. Biol. Chem. 288: 28009-20 (2013)). Therefore, probing the conformation of this loop and how small molecules affect its orientation should provide a more detailed understanding of the fundamental mechanisms underlying the activation of the GLS isoforms.

The technology described herein is directed to overcoming these and other deficiencies in the art.

SUMMARY OF THE INVENTION

A first aspect of the present technology relates to a GLS protein that includes a phenylalanine to tryptophan substitution at the residue corresponding to position 322 of human glutaminase C (GAC).

A second aspect of the present technology relates to a method of screening for compounds that bind to the activation loop of GLS. This method involves contacting GLS protein according to the first aspect of the technology, where the GLS protein comprises an activation loop, with a test compound under conditions effective to permit binding between the activation loop and the test compound. Fluorescence of the substituted tryptophan is detected in the presence of the test compound and the detected fluorescence is compared to fluorescence of a control. A test compound is then identified as being a compound that binds to the activation loop of GLS based on the compared fluorescence, where a change in fluorescence relative to the control indicates that the test compound binds to the activation loop of GLS.

In at least one embodiment, the method of screening for a compound that binds to the activation loop of GLS further involves contacting GLS protein with glutamine in the presence of the test compound under conditions effective for the protein, if active, to convert glutamine to glutamate. The production of glutamate, if any, following said contacting with glutamine is measured and the measured glutamate production is compared to glutamate production of a second control. A test compound is further identified, based on comparing glutamate production, as being a modulator of glutaminase activity of GLS, where a change in glutamate production relative to the second control indicates that the test compound modulates glutaminase activity of GLS.

In at least one embodiment, the method of screening for a compound that binds to the activation loop of GLS further involves identifying a compound that also modulates glutaminase activity of GLS. In this embodiment, a compound identified as being a compound that binds to the activation loop according to the identifying step is selected. GLS protein is then contacted with glutamine in the presence of the selected test compound under conditions effective for the protein, if active, to convert glutamine to glutamate. Production of glutamate, if any, is measured following the contacting with glutamine and the measured glutamate production is compared to glutamate production of a second control. A selected test compound is further identified, based on the comparing, as also being a modulator of glutaminase activity of GLS, where a change in glutamate production relative to the second control indicates that the selected test compound also modulates glutaminase activity of GLS.

A third aspect of the present technology relates to a method of identifying a compound that potentially modulates glutaminase activity of GLS. This method involves contacting GLS protein according to the first aspect of the technology, where the GLS protein comprises an activation loop, with a test compound under conditions effective to permit binding between the activation loop and the test compound. Fluorescence of the substituted tryptophan is detected in the presence of the test compound and the detected fluorescence is compared to fluorescence of a control. A test compound is then identified as being a potential modulator of glutaminase activity of GLS based on the comparing, where a change in fluorescence relative to the control indicates that the test compound potentially modulates glutaminase activity of GLS.

In at least one embodiment, the method of screening for a compound that potentially modulates glutaminase activity of GLS further involves contacting GLS protein with glutamine in the presence of the test compound under conditions effective for the protein, if active, to convert glutamine to glutamate. The production of glutamate, if any, following said contacting with glutamine is measured and the measured glutamate production is compared to glutamate production of a second control. A test compound is further identified, based on comparing glutamate production, as being a modulator of glutaminase activity of GLS, where a change in glutamate production relative to the second control indicates that the test compound modulates glutaminase activity of GLS.

In at least one embodiment, the method of screening for a compound that potentially modulates glutaminase activity of GLS further involves verifying whether the compound modulates glutaminase activity of GLS. In this embodiment, a compound identified as being a potential modulator of glutaminase activity of GLS according to the identifying step is selected. GLS protein is then contacted with glutamine in the presence of the selected test compound under conditions effective for the protein, if active, to convert glutamine to glutamate. Production of glutamate, if any, is measured following contacting with glutamine, and the measured glutamate production is compared to glutamate production of a second control. A selected test compound is further verified as a modulator of glutaminase activity of GLS, based on the comparing, where a change in glutamate production relative to the second control indicates that the test compound modulates glutaminase activity of GLS.

A fourth aspect of the present technology relates to a kit for identifying a compound that binds to the activation loop of GLS and/or potentially modulates glutaminase activity of GLS. This kit includes GLS protein comprising a phenylalanine to tryptophan substitution at the residue corresponding to position 322 of human GAC.

As described more fully herein, it is shown that substituting a tryptophan residue for a phenylalanine at the residue corresponding to position 322 of human GAC provides a sensitive reporter group for reading out the direct binding of BPTES and its clinically relevant analog CB-839. Moreover, this tryptophan reporter group now provides a real-time assay for the direct binding of other allosteric inhibitors, as well as allosteric activators such as inorganic phosphate, and offers strong evidence for the distinct conformational changes induced within the activation loop by activators versus inhibitors.

BRIEF DESCRIPTION OF THE DRAWINGS

FIGS. 2A and 2B are FRET assay spectra in which the FRET signal (1-F/F$_o$) for 25 nM 488-labeled GAC fluorescence (i.e., FRET donor) is increased by the addition of 75 nM QSY9-GAC (i.e., FRET acceptor), representing the formation of GAC tetramers. Addition of 100 mM inorganic phosphate ($HPO_4^{2-}$) (b, red) or sulfate ($SO_4^{2-}$) (c, blue), as shown in FIG. 2A, or 500 nM BPTES (b, red) or CB-839 (c, blue), as shown in FIG. 2B, rapidly increases the FRET signal, indicating the formation of GAC tetramers. In FIG. 2B, the increase in FRET is not readily reversible by addition of a 10-fold excess of unlabeled GAC subunits compared with DMSO control (a, black), reflecting the formation of stable drug-bound tetramers. In contrast, in FIG. 2A tetramers bound to anionic activators are readily reversible ("-" indicates water (b, black)). The results shown are representative of three experiments.

FIGS. 4A-B relate to the inhibition of phosphate-stimulated GAC activity by CB-839 and BPTES. FIG. 4A is a spectra of real-time NADH assays of GAC activity, in which the increased NADH fluorescence (in arbitrary units (AU)) results from the coupled reaction where GAC catalyzes glutamate production, and GDH converts glutamate to α-ketoglutarate and NAD to NADH. The basal activity of 10 nM GAC was first measured upon addition of 20 mM glutamine (Gln), followed by treatment with 1 μM BPTES (b, red), CB-839 (c, blue), or the vehicle DMSO (a, black) and, finally, addition of 100 mM $HPO_4^{2-}$ at the indicated times. FIG. 4B is a graph of relative glutaminase activity. Relative rate analysis was performed on the inhibition of phosphate-stimulated GAC activity by BPTES and CB-839 from FIG. 4A and normalized to the DMSO control. Error bars represent the standard deviation of three independent experiments.

FIGS. 5A-B show a comparison of BPTES-bound and unbound GAC structures. FIG. 5A is a surface representation of the crystal structure of the GAC tetramer bound with ligands DON (PDB code 4O7D), BPTES, and sulfate ($SO_4^{2-}$) (aligned from PDB code 3VOZ), where BPTES and sulfate bind proximal to the activation loop and DON binds within the active site. FIG. 5B is a magnified view of the region of the DON-bound (a, cyan) and BPTES/$SO_4^{2-}$-bound (b, magenta) GAC structures depicting the reorientation of the activation loop. The −180° rotation of the Phe-327 residue with and without bound BPTES is highlighted (dashed line).

FIGS. 6A-E show that F327W detects BPTES binding while retaining wild-type (WT) properties. FIGS. 6A and 6B are tryptophan fluorescence spectra (in arbitrary units (AU)) of the $GAC_{F327W}$ mutant (FIG. 6B) and WT GAC (FIG. 6A) before (a, black) and after (b, red) addition of 1 μM BPTES. Addition of BPTES results in no change in the tryptophan fluorescence of WT GAC (FIG. 6A) but significant quenching of the tryptophan emission of the $GAC_{F327W}$ mutant (FIG. 6B). The results shown are representative of three experiments. FIGS. 6C and 6D are SEC-MALS elution profiles (in arbitrary units (AU)) (solid lines) and molecular weight distribution (broken lines) of 5 mg/ml samples of WT GAC (FIG. 6C) and $GAC_{F327W}$ (FIG. 6D) before (a, black, dashed blue) and after (b, red, dotted blue) preincubation with 50 μM BPTES, illustrating a significant shift from a heterogeneous population of GAC dimers and tetramers to a more homogenous population of tetramers following preincubation with BPTES. LS=light scattering; MW=molecular weight. FIG. 6E is a graph showing that the $GAC_{F327W}$ mutant (closed circles) retains its catalytic properties compared with WT GAC (open circles), with an observed $K_M$ of 15.0±1.7 mmol/liter and a $V_{max}$ value of 435±19 μmol/min versus a $K_M$ of 16.4±0.4 mmol/liter and a $V_{max}$ value of 453±8 μmol/min for WT GAC. Points represent the mean and error bars the standard deviation of three independent experiments.

FIGS. 7A-B show that the Phe-327 peptide backbone interacts with the thiadiazole ring of BPTES-class inhibitors. FIGS. 7A and 7B are close-up ribbon diagrams of the binding interactions of BPTES in two different orientations from two separate published structures (FIG. 7A, PDB code 3UO9; FIG. 7B, PDB code 4JKT) with the native residues Leu-326 and Phe-327 (DeLaBarre et al., "Full-Length Human Glutaminase in Complex with an Allosteric Inhibitor," *Biochemistry* 50:10764-70 (2011); Cassago et al., "Mitochondrial Localization and Structure-Based Phosphate Activation Mechanism of Glutaminase C with Implications for Cancer Metabolism," *Proc. Natl. Acad. Sci. U.S.A.* 109:1092-97 (2012), each of which is hereby incorporated by reference in its entirety). Interactions of the peptide backbone of these residues with the bisthiadiazole ring of BPTES are highlighted with dashed lines.

FIGS. 8A-C demonstrate that changes in F327W fluorescence provide a direct binding assay for BPTES-like molecules. FIGS. 8A and 8B are tryptophan fluorescence spectra showing that addition of increasing concentrations of BPTES (FIG. 8A) and CB-839 (FIG. 8B) quenches the tryptophan fluorescence of 100 nM $GAC_{F327W}$. FIG. 8C is a graph of fluorescence quenching of the $GAC_{F327W}$ mutant by BPTES (a, black) and CB-839 (b, red) quantified and fit to a bimolecular interaction equation, giving $K_D$ values of 70±5 nM and 34±5 nM for BPTES and CB-839, respectively. Points represent the mean and error bars the standard deviation of three independent experiments.

FIGS. 9A-B demonstrate that GAC tetramer formation is required for BPTES binding. FIG. 9A is a tryptophan fluorescence spectra showing that tryptophan fluorescence emission of 500 nM $GAC_{F327W}$ mutant (a, black) is rapidly quenched following addition of 1 µM BPTES. Under the same conditions, BPTES does not quench the fluorescence of 500 nM dimeric $GAC_{F327W,D391K}$ double mutant (b, red). FIG. 9B is a SEC-MALS elution profile of the $GAC_{F327W,D391K}$ double mutant (5 mg/ml) and shows a molecular weight distribution consistent with a dimer both before (a, black, broken blue line) and after (b, red, dotted blue line) preincubation with 50 µM BPTES. LS=light scattering; MW=molecular weight.

FIGS. 10A-C demonstrate that F327W fluorescence is enhanced by allosteric activators and correlates with their ability to activate GAC activity. FIG. 10A is a tryptophan fluorescence spetra showing that addition of inorganic phosphate ($HPO_4^{2-}$) or sulfate ($SO_4^{2-}$) to give a final concentration of 50 mM to the F327W mutant (400 nM) resulted in enhancement of tryptophan fluorescence, where inorganic phosphate stimulated the greater enhancement (a, black) compared with sulfate (b, red). Addition of inorganic phosphate to WT GAC (c, blue) is also shown. FIG. 10B is a graph of glutaminase activity of 50 nM WT GAC measured in the presence of increasing concentrations of phosphate (a, black circles) or sulfate (b, red circles), giving $K_D$ values of 20.6±0.4 mM and 36.4±3.0 mM, respectively. Tryptophan fluorescence enhancement upon addition of these anions to 400 nM $GAC_{F327W}$ is overlaid (blue diamonds and blue triangles). Data points and error bars represent the mean±S.D. of three independent experiments. FIG. 10C is a SEC-MALS elution profile of 5 mg/ml WT GAC, where phosphate (c, orange) or sulfate (b, green) was included in the running buffer at a concentration of 50 mM, and shows the shift from a molecular weight distribution of a heterogeneous population of GAC dimers and tetramers in the absence of either anion (broken blue line) to an equilibrium of 8- to 16-mers for sulfate (dotted blue line) up to greater than 32-mers for phosphate (spaced dotted blue lines). LS=light scattering; MW=molecular weight; a, black, indicates no anion addition.

DETAILED DESCRIPTION OF THE INVENTION

Figure 1:
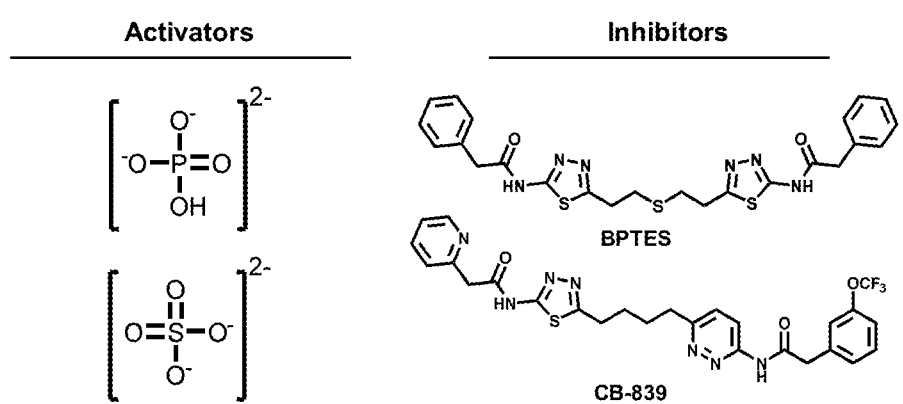
FIG. 1 shows the chemical structures of the allosteric anionic activators inorganic phosphate ($HPO_4^{2-}$) and sulfate ($SO_4^{2-}$) and inhibitors BPTES and CB-839.

The present technology relates to mutant GLS proteins. In addition, the present invention relates to methods of using these proteins in methods of screening for compounds that bind to the activation loop of GLS and methods of identifying compounds that potentially modulate glutaminase activity of GLS. The present invention further relates to a screening kit for compounds that bind to the GLS activation loop and/or potentially modulate glutaminase activity of GLS.

The first step in glutamine catabolism is catalysis by the mitochondrial enzyme glutaminase, with a specific isoform, glutaminase C (GAC), being highly expressed in cancer cells. GAC activation requires the formation of homotetramers, promoted by anionic allosteric activators such as inorganic phosphate. This leads to the proper orientation of a flexible loop proximal to the dimer-dimer interface that is essential for catalysis (i.e., the "activation loop"). A major class of allosteric inhibitors of GAC, with the prototype being bis-2-(5-phenylacetamido-1,2,4-thiadiazol-2-yl)ethyl sulfide (BPTES) and the related molecule CB-839, binds to the activation loop and induces the formation of an inactive tetramer (two inhibitors bound per active tetramer). Described herein is a direct readout for monitoring the dynamics of the activation loop of GAC in response to these allosteric inhibitors using mutant mouse GLS protein having a substitution of phenylalanine with tryptophan at position 327 (F327W), which corresponds to residue 322 of human GAC. The tryptophan fluorescence of the $GAC_{F327W}$ mutant undergoes a marked quenching upon the binding of BPTES or CB-839, yielding titration profiles that make it possible to measure the binding affinities of these inhibitors for the enzyme. Allosteric activators like phosphate induce the opposite effect (i.e., fluorescence enhancement). These results describe direct readouts for the binding of the BPTES class of allosteric inhibitors as well as for inorganic phosphate and related activators of GAC (and other GLS enzymes), which should facilitate screening for additional modulators of this important metabolic enzyme. Further, because the activation loop is conserved in GAC and KGA (and across taxa), it is expected that GAC can be subsituted with other GLS enzymes in these assays (e.g., substituting GAC with KGA, substituting mouse protein with human or rat protein, etc.). It is similarly expected that a compound's effect on GAC in these assays is predictive of the effect that compound would have on KGA, and vice versa.

According to a first aspect, the present technology relates to a mutant GLS protein comprising a phenylalanine to tryptophan substitution at the residue corresponding to position 322 of human GAC.

According to this and all aspects of the present technology, mutant GLS proteins include both GLS isoforms GAC and KGA. In at least one embodiment, the protein is from a human, mouse, or rat. The GLS isoforms GAC and KGA are splice variants of each other. Specifically, their C-terminal regions are unique (i.e., residues 550-603 of mouse GAC and residues 550-674 of mouse KGA). Likewise, human GAC and KGA proteins each have unique C-terminal regions (i.e., residues 545-598 of human GAC and residues 545-669 of human KGA). In each of the human, mouse, and rat GAC and KGA proteins, the activation loop (i.e., residues 311-322 of human GAC and human KGA, residues 316-327 of mouse GAC and KGA, and residues 316-327 of rat GAC and KGA) is conserved.

The wild-type human GAC protein is set forth in Gen-Bank Accession No. NP_001243239.1, which is hereby incorporated by reference in its entirety, and has the amino acid sequence of SEQ ID NO:2, as follows (the activation loop is underlined).

```
Met Met Arg Leu Arg Gly Ser Gly Met Leu Arg Asp Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Arg Pro Ala Ala Gly Pro
        35                  40                  45

Ala Ala Ala Ala Arg Leu His Pro Trp Trp Gly Gly Gly Trp Pro
50                      55                  60

Ala Glu Pro Leu Ala Arg Gly Leu Ser Ser Ser Pro Ser Glu Ile Leu
65                      70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
                100                 105                 110

Asp Ala Phe Gly Asn Ser Glu Gly Lys Glu Leu Val Ala Ser Gly Glu
            115                 120                 125

Asn Lys Ile Lys Gln Gly Leu Leu Pro Ser Leu Glu Asp Leu Leu Phe
        130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
    290                 295                 300

Val His Arg Tyr Val Gly Lys Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
        355                 360                 365

Glu Tyr Val Gly Phe Ser Asn Ala Thr Phe Gln Ser Glu Arg Glu Ser
    370                 375                 380

Gly Asp Arg Asn Phe Ala Ile Gly Tyr Tyr Leu Lys Glu Lys Lys Cys
```

```
                385                 390                 395                 400
            Phe Pro Glu Gly Thr Asp Met Val Gly Ile Leu Asp Phe Tyr Phe Gln
                            405                 410                 415

Leu Cys Ser Ile Glu Val Thr Cys Glu Ser Ala Ser Val Met Ala Ala
                            420                 425                 430

Thr Leu Ala Asn Gly Gly Phe Cys Pro Ile Thr Gly Glu Arg Val Leu
                            435                 440                 445

Ser Pro Glu Ala Val Arg Asn Thr Leu Ser Leu Met His Ser Cys Gly
                    450                 455                 460

Met Tyr Asp Phe Ser Gly Gln Phe Ala Phe His Val Gly Leu Pro Ala
            465                 470                 475                 480

Lys Ser Gly Val Ala Gly Gly Ile Leu Leu Val Val Pro Asn Val Met
                            485                 490                 495

Gly Met Met Cys Trp Ser Pro Pro Leu Asp Lys Met Gly Asn Ser Val
                            500                 505                 510

Lys Gly Ile His Phe Cys His Asp Leu Val Ser Leu Cys Asn Phe His
                            515                 520                 525

Asn Tyr Asp Asn Leu Arg His Phe Ala Lys Lys Leu Asp Pro Arg Arg
                            530                 535                 540

Glu Gly Gly Asp Gln Arg His Ser Phe Gly Pro Leu Asp Tyr Glu Ser
            545                 550                 555                 560

Leu Gln Gln Glu Leu Ala Leu Lys Glu Thr Val Trp Lys Lys Val Ser
                            565                 570                 575

Pro Glu Ser Asn Glu Asp Ile Ser Thr Thr Val Val Tyr Arg Met Glu
                            580                 585                 590

Ser Leu Gly Glu Lys Ser
                    595
```

The cDNA sequence encoding the above wild-type human GAC protein is set forth in GenBank Accession No. NM_014905.4, which is hereby incorporated by reference in its entirety.

The wild-type mouse GAC protein is set forth in GenBank Accession No. NP_001106854.1, which is hereby incorporated by reference in its entirety, and has the amino acid sequence of SEQ ID NO:3, as follows (the activation loop is underlined).

```
            Met Met Arg Leu Arg Gly Ser Ala Met Leu Arg Glu Leu Leu Leu Arg
            1                   5                   10                  15

Pro Pro Ala Ala Val Gly Ala Val Leu Arg Arg Ala Gln Pro Leu Gly
                            20                  25                  30

Thr Leu Cys Arg Arg Pro Arg Gly Gly Ser Arg Pro Thr Ala Gly Leu
                            35                  40                  45

Val Ala Ala Ala Arg Leu His Pro Trp Trp Gly Gly Gly Arg Ala
                    50                  55                  60

Lys Gly Pro Gly Ala Gly Gly Leu Ser Ser Ser Pro Ser Glu Ile Leu
            65                  70                  75                  80

Gln Glu Leu Gly Lys Gly Gly Thr Pro Pro Gln Gln Gln Gln Gln Gln
                            85                  90                  95

Gln Gln Gln Pro Gly Ala Ser Pro Pro Ala Ala Pro Gly Pro Lys Asp
                            100                 105                 110

Ser Pro Gly Glu Thr Asp Ala Phe Gly Asn Ser Glu Gly Lys Glu Met
                            115                 120                 125

Val Ala Ala Gly Asp Asn Lys Ile Lys Gln Gly Leu Leu Pro Ser Leu
                            130                 135                 140

Glu Asp Leu Leu Phe Tyr Thr Ile Ala Glu Gly Gln Glu Lys Ile Pro
            145                 150                 155                 160
```

-continued

```
Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
    210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
            340                 345                 350

Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
    370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
        435                 440                 445

Gly Glu Arg Val Leu Ser Pro Glu Ala Val Arg Asn Thr Leu Ser Leu
    450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Ile Leu Leu Val
                485                 490                 495

Val Pro Asn Val Met Gly Met Met Cys Trp Ser Pro Leu Asp Lys
            500                 505                 510

Met Gly Asn Ser Val Lys Gly Ile His Phe Cys His Asp Leu Val Ser
        515                 520                 525

Leu Cys Asn Phe His Asn Tyr Asp Asn Leu Arg His Phe Ala Lys Lys
    530                 535                 540

Leu Asp Pro Arg Arg Glu Gly Gly Asp Gln Arg His Ser Phe Gly Pro
545                 550                 555                 560

Leu Asp Tyr Glu Ser Leu Gln Gln Glu Leu Ala Leu Lys Asp Thr Val
                565                 570                 575
```

-continued

```
Trp Lys Lys Val Ser Pro Glu Ser Ser Asp Asp Thr Ser Thr Thr Val
            580                 585                 590

Val Tyr Arg Met Glu Ser Leu Gly Glu Arg Ser
            595                 600
```

The cDNA sequence encoding the above wild-type mouse GAC protein is set forth in GenBank Accession No. NM_001113383.1, which is hereby incorporated by reference in its entirety.

The wild-type rat GAC protein is set forth in GenBank Accession No. NP_001103438.1, which is hereby incorporated by reference in its entirety, and has the amino acid sequence of SEQ ID NO:4, as follows (the activation loop is underlined).

```
Met Met Arg Leu Arg Gly Ser Ala Met Leu Arg Glu Leu Leu Arg
1               5                   10                  15

Pro Pro Ala Ala Val Gly Gly Val Leu Arg Arg Ala Gln Pro Leu Gly
            20                  25                  30

Thr Leu Cys Arg Arg Pro Arg Gly Gly Ser Arg Pro Ala Ala Gly Leu
            35                  40                  45

Val Ala Ala Ala Arg Leu His Pro Trp Trp Gly Gly Gly Arg Ala
            50                  55                  60

Lys Gly Pro Gly Ser Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln
            85                  90                  95

Gln Gln Gln Pro Gly Ala Ser Pro Ala Ala Pro Gly Pro Lys Asp
            100                 105                 110

Ser Pro Gly Glu Thr Asp Ala Phe Gly Asn Ser Glu Gly Lys Glu Met
            115                 120                 125

Val Ala Ala Gly Asp Asn Lys Val Lys Gln Gly Leu Leu Pro Ser Leu
            130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
            195                 200                 205

Val Gln Ser Asn Ile Val Leu Leu Thr Gln Ala Phe Arg Arg Lys Phe
            210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
            245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
            275                 280                 285

Leu Gln Ser Cys Val Lys Pro Leu Lys Tyr Ala Ile Ala Val Asn Asp
            290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
```

-continued

```
                340                 345                 350
Gly Val Asn Asn Ala Glu Lys Phe Asp Tyr Val Met Gln Phe Leu Asn
                355                 360                 365
Lys Met Ala Gly Asn Glu Tyr Val Gly Phe Ser Asn Ala Thr Phe Gln
                370                 375                 380
Ser Glu Arg Glu Ser Gly Asp Arg Asn Phe Ala Ile Gly Tyr Tyr Leu
385                 390                 395                 400
Lys Glu Lys Lys Cys Phe Pro Glu Gly Thr Asp Met Val Gly Ile Leu
                405                 410                 415
Asp Phe Tyr Phe Gln Leu Cys Ser Ile Glu Val Thr Cys Glu Ser Ala
                420                 425                 430
Ser Val Met Ala Ala Thr Leu Ala Asn Gly Gly Phe Cys Pro Ile Thr
                435                 440                 445
Gly Glu Arg Val Leu Ser Pro Glu Ala Val Arg Asn Thr Leu Ser Leu
                450                 455                 460
Met His Ser Cys Gly Met Tyr Asp Phe Ser Gly Gln Phe Ala Phe His
465                 470                 475                 480
Val Gly Leu Pro Ala Lys Ser Gly Val Ala Gly Gly Ile Leu Leu Val
                485                 490                 495
Val Pro Asn Val Met Gly Met Met Cys Trp Ser Pro Pro Leu Asp Lys
                500                 505                 510
Met Gly Asn Ser Val Lys Gly Ile His Phe Cys His Asp Leu Val Ser
                515                 520                 525
Leu Cys Asn Phe His Asn Tyr Asp Asn Leu Arg His Phe Ala Lys Lys
                530                 535                 540
Leu Asp Pro Arg Arg Glu Gly Gly Asp Gln Arg His Ser Phe Gly Pro
545                 550                 555                 560
Leu Asp Tyr Glu Ser Leu Gln Gln Glu Leu Ala Leu Lys Asp Thr Val
                565                 570                 575
Trp Lys Lys Val Ser Pro Glu Ser Ser Asp Asp Thr Ser Thr Thr Ile
                580                 585                 590
Val Tyr Arg Met Glu Ser Leu Gly Glu Arg Ser
                595                 600
```

The cDNA sequence encoding the above wild-type rat GAC protein is set forth in GenBank Accession No. NM_001109968.1, which is hereby incorporated by reference in its entirety.

The wild-type human KGA protein is set forth in GenBank Accession No. NP_055720.3, which is hereby incorporated by reference in its entirety, and has the amino acid sequence of SEQ ID NO:5, as follows (the activation loop is underlined).

```
Met Met Arg Leu Arg Gly Ser Gly Met Leu Arg Asp Leu Leu Leu Arg
1                   5                   10                  15
Ser Pro Ala Gly Val Ser Ala Thr Leu Arg Arg Ala Gln Pro Leu Val
                20                  25                  30
Thr Leu Cys Arg Arg Pro Arg Gly Gly Gly Arg Pro Ala Ala Gly Pro
                35                  40                  45
Ala Ala Ala Ala Arg Leu His Pro Trp Trp Gly Gly Gly Trp Pro
                50                  55                  60
Ala Glu Pro Leu Ala Arg Gly Leu Ser Ser Ser Pro Ser Glu Ile Leu
65                  70                  75                  80
Gln Glu Leu Gly Lys Gly Ser Thr His Pro Gln Pro Gly Val Ser Pro
                85                  90                  95
Pro Ala Ala Pro Ala Ala Pro Gly Pro Lys Asp Gly Pro Gly Glu Thr
                100                 105                 110
```

```
Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
        130                 135                 140

Tyr Thr Ile Ala Glu Gly Gln Glu Lys Ile Pro Val His Lys Phe Ile
145                     150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
                180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
        210                 215                 220

Met Ser Phe Thr Ser His Ile Asp Glu Leu Tyr Glu Ser Ala Lys Lys
225                     230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
                260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
        290                 295                 300

Val His Arg Tyr Val Gly Lys Glu Pro Ser Gly Leu Arg Phe Asn Lys
305                     310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
                340                 345                 350

Glu Lys Phe Asp Tyr Val Met Gln Phe Leu Asn Lys Met Ala Gly Asn
                355                 360                 365

Glu Tyr Val Gly Phe Ser Asn Ala Thr Phe Gln Ser Glu Arg Glu Ser
        370                 375                 380

Gly Asp Arg Asn Phe Ala Ile Gly Tyr Tyr Leu Lys Glu Lys Lys Cys
385                     390                 395                 400

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
                420                 425                 430

Thr Leu Ala Asn Gly Gly Phe Cys Pro Ile Thr Gly Glu Arg Val Leu
        435                 440                 445

Ser Pro Glu Ala Val Arg Asn Thr Leu Ser Leu Met His Ser Cys Gly
        450                 455                 460

Met Tyr Asp Phe Ser Gly Gln Phe Ala Phe His Val Gly Leu Pro Ala
465                     470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
                500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
        530                 535                 540
```

-continued

```
Glu Gly Gly Asp Gln Arg Val Lys Ser Val Ile Asn Leu Leu Phe Ala
545                 550                 555                 560

Ala Tyr Thr Gly Asp Val Ser Ala Leu Arg Arg Phe Ala Leu Ser Ala
            565                 570                 575

Met Asp Met Glu Gln Arg Asp Tyr Asp Ser Arg Thr Ala Leu His Val
            580                 585                 590

Ala Ala Ala Glu Gly His Val Glu Val Val Lys Phe Leu Leu Glu Ala
        595                 600                 605

Cys Lys Val Asn Pro Phe Pro Lys Asp Arg Trp Asn Asn Thr Pro Met
        610                 615                 620

Asp Glu Ala Leu His Phe Gly His Asp Val Phe Lys Ile Leu Gln
625                 630                 635                 640

Glu Tyr Gln Val Gln Tyr Thr Pro Gln Gly Asp Ser Asp Asn Gly Lys
            645                 650                 655

Glu Asn Gln Thr Val His Lys Asn Leu Asp Gly Leu Leu
            660                 665
```

The cDNA sequence encoding the above wild-type human KGA protein is set forth in GenBank Accession No. NM_001256310.1, which is hereby incorporated by reference in its entirety.

The wild-type mouse KGA protein is set forth in GenBank Accession No. NP_001074550.1, which is hereby incorporated by reference in its entirety, and has the amino acid sequence of SEQ ID NO:6, as follows (the activation loop is underlined).

```
Met Met Arg Leu Arg Gly Ser Ala Met Leu Arg Glu Leu Leu Leu Arg
1                   5                   10                  15

Pro Pro Ala Ala Val Gly Ala Val Leu Arg Arg Ala Gln Pro Leu Gly
            20                  25                  30

Thr Leu Cys Arg Arg Pro Arg Gly Gly Ser Arg Pro Thr Ala Gly Leu
            35                  40                  45

Val Ala Ala Arg Leu His Pro Trp Trp Gly Gly Gly Arg Ala
            50                  55                  60

Lys Gly Pro Gly Ala Gly Leu Ser Ser Pro Ser Glu Ile Leu
65                  70                  75                  80

Gln Glu Leu Gly Lys Gly Thr Pro Pro Gln Gln Gln Gln Gln
                85                  90                  95

Gln Gln Gln Pro Gly Ala Ser Pro Pro Ala Ala Pro Gly Pro Lys Asp
            100                 105                 110

Ser Pro Gly Glu Thr Asp Ala Phe Gly Asn Ser Glu Gly Lys Glu Met
            115                 120                 125

Val Ala Ala Gly Asp Asn Lys Ile Lys Gln Gly Leu Leu Pro Ser Leu
            130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
                180                 185                 190

Thr Thr Ser Asp Gly Val Met Leu Asp Lys Asp Leu Phe Lys Lys Cys
            195                 200                 205

Val Gln Ser Asn Ile Val Leu Leu Thr Gln Ala Phe Arg Arg Lys Phe
            210                 215                 220

Val Ile Pro Asp Phe Met Ser Phe Thr Ser His Ile Asp Glu Leu Tyr
225                 230                 235                 240
```

-continued

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
                340                 345                 350

Gly Val Asn Asn Ala Glu Lys Phe Asp Tyr Val Met Gln Phe Leu Asn
            355                 360                 365

Lys Met Ala Gly Asn Glu Tyr Val Gly Phe Ser Asn Ala Thr Phe Gln
    370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
    435                 440                 445

Gly Glu Arg Val Leu Ser Pro Glu Ala Val Arg Asn Thr Leu Ser Leu
450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Gly Ile Leu Leu Val
                485                 490                 495

Val Pro Asn Val Met Gly Met Met Cys Trp Ser Pro Pro Leu Asp Lys
            500                 505                 510

Met Gly Asn Ser Val Lys Gly Ile His Phe Cys His Asp Leu Val Ser
    515                 520                 525

Leu Cys Asn Phe His Asn Tyr Asp Asn Leu Arg His Phe Ala Lys Lys
    530                 535                 540

Leu Asp Pro Arg Arg Glu Gly Gly Asp Gln Arg Val Lys Ser Val Ile
545                 550                 555                 560

Asn Leu Leu Phe Ala Ala Tyr Thr Gly Asp Val Ser Ala Leu Arg Arg
                565                 570                 575

Phe Ala Leu Ser Ala Met Asp Met Glu Gln Arg Asp Tyr Asp Ser Arg
            580                 585                 590

Thr Ala Leu His Val Ala Ala Glu Gly His Val Glu Val Val Lys
    595                 600                 605

Phe Leu Leu Glu Ala Cys Lys Val Asn Pro Phe Pro Lys Asp Arg Trp
    610                 615                 620

Asn Asn Thr Pro Met Asp Glu Ala Leu His Phe Gly His His Asp Val
625                 630                 635                 640

-continued

```
Phe Lys Ile Leu Gln Glu Tyr Gln Val Gln Tyr Thr Pro Gln Gly Asp
                645                 650                 655

Ser Asp Asp Gly Lys Gly Asn Gln Thr Val His Lys Asn Leu Asp Gly
            660                 665                 670

Leu Leu
```

The cDNA sequence encoding the above wild-type mouse KGA protein is set forth in GenBank Accession No. NM_001081081.2, which is hereby incorporated by reference in its entirety.

The wild-type rat KGA protein is set forth in GenBank Accession No. NP_036701.2, which is hereby incorporated by reference in its entirety, and has the amino acid sequence of SEQ ID NO:7, as follows (the activation loop is underlined).

```
Met Met Arg Leu Arg Gly Ser Ala Met Leu Arg Glu Leu Leu Leu Arg
1               5                   10                  15

Pro Pro Ala Ala Val Gly Gly Val Leu Arg Arg Ala Gln Pro Leu Gly
                20                  25                  30

Thr Leu Cys Arg Arg Pro Arg Gly Gly Ser Arg Pro Ala Ala Gly Leu
            35                  40                  45

Val Ala Ala Arg Leu His Pro Trp Trp Gly Gly Gly Arg Ala
        50              55                  60

Lys Gly Pro Gly Ser Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

Gln Gln Gln Pro Gly Ala Ser Pro Pro Ala Ala Pro Gly Pro Lys Asp
                100                 105                 110

Ser Pro Gly Glu Thr Asp Ala Phe Gly Asn Ser Glu Gly Lys Glu Met
            115                 120                 125

Val Ala Ala Gly Asp Asn Lys Val Lys Gln Gly Leu Leu Pro Ser Leu
        130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
                180                 185                 190

Thr Thr Ser Asp Gly Val Met Leu Asp Lys Asp Leu Phe Lys Lys Cys
            195                 200                 205

Val Gln Ser Asn Ile Val Leu Leu Thr Gln Ala Phe Arg Arg Lys Phe
        210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys V Alala Asp Tyr Ile Pro
                245                 250                 255

Gln Leu Ala Lys Phe Ser Pro Asp Leu Trp Gly Val Ser Val Cys Thr
                260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
            290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
                325                 330                 335
```

```
Pro Met Val Asn Ala Gly Ala Ile Val Val Thr Ser Leu Ile Lys Gln
            340             345             350

Gly Val Asn Asn Ala Glu Lys Phe Asp Tyr Val Met Gln Phe Leu Asn
            355             360             365

Lys Met Ala Gly Asn Glu Tyr Val Gly Phe Ser Asn Ala Thr Phe Gln
            370             375             380

Ser Glu Arg Glu Ser Gly Asp Arg Asn Phe Ala Ile Gly Tyr Tyr Leu
385                 390             395                 400

Lys Glu Lys Lys Cys Phe Pro Glu Gly Thr Asp Met Val Gly Ile Leu
                405             410             415

Asp Phe Tyr Phe Gln Leu Cys Ser Ile Glu Val Thr Cys Glu Ser Ala
            420             425             430

Ser Val Met Ala Ala Thr Leu Ala Asn Gly Gly Phe Cys Pro Ile Thr
            435             440             445

Gly Glu Arg Val Leu Ser Pro Glu Ala Val Arg Asn Thr Leu Ser Leu
            450             455             460

Met His Ser Cys Gly Met Tyr Asp Phe Ser Gly Gln Phe Ala Phe His
465                 470             475                 480

Val Gly Leu Pro Ala Lys Ser Gly V Alala Gly Gly Ile Leu Leu Val
                485             490             495

Val Pro Asn Val Met Gly Met Met Cys Trp Ser Pro Pro Leu Asp Lys
            500             505             510

Met Gly Asn Ser Val Lys Gly Ile His Phe Cys His Asp Leu Val Ser
            515             520             525

Leu Cys Asn Phe His Asn Tyr Asp Asn Leu Arg His Phe Ala Lys Lys
    530             535             540

Leu Asp Pro Arg Arg Glu Gly Gly Asp Gln Arg Val Lys Ser Val Ile
545             550             555                 560

Asn Leu Leu Phe Ala Ala Tyr Thr Gly Asp Val Ser Ala Leu Arg Arg
                565             570             575

Phe Ala Leu Ser Ala Met Asp Met Glu Gln Arg Asp Tyr Asp Ser Arg
                580             585             590

Thr Ala Leu His Val Ala Ala Glu Gly His Val Glu Val Val Lys
            595             600             605

Phe Leu Leu Glu Ala Cys Lys Val Asn Pro Phe Pro Lys Asp Arg Trp
    610             615             620

Asn Asn Thr Pro Met Asp Glu Ala Leu His Phe Gly His His Asp Val
625             630             635                 640

Phe Lys Ile Leu Gln Glu Tyr Gln Val Gln Tyr Thr Pro Gln Gly Asp
                645             650             655

Ser Asp Asp Gly Lys Glu Asn Gln Thr Val His Lys Asn Leu Asp Gly
            660             665             670

Leu Leu
```

The cDNA sequence encoding the above wild-type rat KGA protein is set forth in GenBank Accession No. NM_012569.2, which is hereby incorporated by reference in its entirety.

Mutant 0GLS proteins according to the present technology have a phenylaline to tryptophan substitution at the position corresponding to residue 322 of human GAC. This includes, for example, human GAC proteins containing a phenylalanine to tryptophan substitution at position 322 (F322W), mouse GAC proteins containing a phenylalanine to tryptophan substitution at position 327 (F327W), rat GAC proteins containing a phenylalanine to tryptophan substitution at position 327 (F327W), human KGA proteins containing a phenylalanine to tryptophan substitution at position 322 (F322W), mouse KGA proteins containing a phenylalanine to tryptophan substitution at position 327 (F327W), and rat KGA proteins containing a phenylalanine to tryptophan substitution at position 327 (F327W), each of which is shown in Table 1 below. Other suitable GLS proteins include GLS proteins from other organisms, as long as they contain the corresponding phenylalanine to tryptophan substitution in their activation loop.

TABLE 1

Full-Length Mutant GLS Proteins

| SEQ ID NO: | Amino Acid Sequence (the activation loop is in bold) | Description |
|---|---|---|
| 8 | MMRLRGSGMLRDLLLRSPAGVSATLRRAQPLVTLCRRPRGGGRPAAGPAAAARLHPWWGGGGWPAEPLARGLSSSPSEILQELGKGSTHPQPGVSPPAAPAAPGPKDGPGETDAFGNSEGKELVASGENKIKQGLLPSLEDLLFYTIAEGQEKIPVHKFITALKSTGLRTSDPRLKECMDMLRLTLQTTSDGVMLDKDLFKKCVQSNIVLLTQAFRRKFVIPDFMSFTSHIDELYESAKKQSGGKVADYIPQLAKFSPDLWGVSVCTVDGQRHSTGDTKVPFCLQSCVKPLKYAIAVNDLGTEYVHRYVGKEPSGLRFNKLWLNEDDKPHNPMVNAGAIVVTSLIKQGVNNAEKFDYVMQFLNKMAGNEYVGFSNATFQSERESGDRNFAIGYYLKEKKCFPEGTDMVGILDFYFQLCSIEVTCESASVMAATLANGGFCPITGERVLSPEAVRNTLSLMHSCGMYDFSGQFAFHVGLPAKSGVAGGILLVVPNVMGMMCWSPPLDKMGNSVKGIHFCHDLVSLCNFHNYDNLRHFAKKLDPRREGGDQRHSFGPLDYESLQQELALKETVWKKVSPESNEDISTTVVYRMESLGEKS | Human GAC F322W |
| 9 | MMRLRGSAMLRELLLRPPAAVGAVLRRAQPLGTLCRRPRGGSRPTAGLVAAARLHPWWGGGGRAKGPGAGGLSSSPSEILQELGKGGTPPQQQQQQQQPGASPPAAPGPKDSPGETDAFGNSEGKEMVAAGDNKIKQGLLPSLEDLLFYTIAEGQEKIPVHKFITALKSTGLRTSDPRLKECMDMLRLTLQTTSDGVMLDKDLFKKCVQSNIVLLTQAFRRKFVIPDFMSFTSHIDELYESAKKQSGGKVADYIPQLAKFSPDLWGVSVCTVDGQRHSIGDTKVPFCLQSCVKPLKYAIAVNDLGTEYVHRYVGKEPSGLRFNKLWLNEDDKPHNPMVNAGAIVVTSLIKQGVNNAEKFDYVMQFLNKMAGNEYVGFSNATFQSERESGDRNFAIGYYLKEKKCFPEGTDMVGILDFYFQLCSIEVTCESASVMAATLANGGFCPITGERVLSPEAVRNTLSLMHSCGMYDFSGQFAFHVGLPAKSGVAGGILLVVPNVMGMMCWSPPLDKMGNSVKGIHFCHDLVSLCNFHNYDNLRHFAKKLDPRREGGDQRHSFGPLDYESLQQELALKDTVWKKVSPESSDDTSTTVVYRMESLGERS | Mouse GAC F327W |
| 10 | MMRLRGSAMLRELLLRPPAAVGGVLRRAQPLGTLCRRPRGGSRPAAGLVAAARLHPWWGGGGRAKGPGSGGLSSSPSEILQELGKGGTPPQQQQQQQQPGASPPAAPGPKDSPGETDAFGNSEGKEMVAAGDNKVKQGLLPSLEDLLFYTIAEGQEKIPVHKFITALKSTGLRTSDPRLKECMDMLRLTLQTTSDGVMLDKDLFKKCVQSNIVLLTQAFRRKFVIPDFMSFTSHIDELYESAKKQSGGKVADYIPQLAKFSPDLWGVSVCTVDGQRHSIGDTKVPFCLQSCVKPLKYAIAVNDLGTEWHRYVGKEPSGLRFNKLWLNEDDKPHNPMVNAGAIVVTSLIKQGVNNAEKFDYVMQFLNKMAGNEYVGFSNATFQSERESGDRNFAIGYYLKEKKCFPEGTDMVGILDFYFQLCSIEVTCESASVMAATLANGGFCPITGERVLSPEAVRNTLSLMHSCGMYDFSGQFAFHVGLPAKSGVAGGILLVVPNVMGMMCWSPPLDKMGNSVKGIHFCHDLVSLCNFHNYDNLRHFAKKLDPRREGGDQRHSFGPLDYESLQQELALKDTVWKKVSPESSDDTSTTIVYRMESLGERS | Rat GAC F327W |
| 11 | MMRLRGSGMLRDLLLRSPAGVSATLRRAQPLVTLCRRPRGGGRPAAGPAAAARLHPWWGGGGWPAEPLARGLSSSPSEILQELGKGSTHPQPGVSPPAAPAAPGPKDGPGETDAFGNSEGKELVASGENKIKQGLLPSLEDLLFYTIAEGQEKIPVHKFITALKSTGLRTSDPRLKECMDMLRLTLQTTSDGVMLDKDLFKKCVQSNIVLLTQAFRRKFVIPDFMSFTSHIDELYESAKKQSGGKVADYIPQLAKFSPDLWGVSVCTVDGQRHSTGDTKVPFCLQSCVKPLKYAIAVNDLGTEYVHRYVGKEPSGLRFNKLWLNEDDKPHNPMVNAGAIVVTSLIKQGVNNAEKFDYVMQFLNKMAGNEYVGFSNATFQSERESGDRNFAIGYYLKEKKCFPEGTDMVGILDFYFQLCSIEVTCESASVMAATLANGGFCPITGERVLSPEAVRNTLSLMHSCGMYDFSGQFAFHVGLPAKSGVAGGILLVVPNVMGMMCWSPPLDKMGNSVKGIHFCHDLVSLCNFHNYDNLRHFAKKLDPRREGGDQRVKSVINLLFAAYTGDVSALRRFALSAMDMEQRDYDSRTALHVAAAEGHVEVVKFLLEACKVNPFPKDRWNNTPMDEALHFGHHDVFKILQEYQVQYTPQGDSDNGKENQTVHKNLDGLL | Human KGA F322W |
| 12 | MMRLRGSAMLRELLLRPPAAVGAVLRRAQPLGTLCRRPRGGSRPTAGLVAAARLHPWWGGGGRAKGPGAGGLSSSPSEILQELGKGGTPPQQQQQQQQPGASPPAAPGPKDSPGETDAFGNSEGKEMVAAGDNKIKQGLLPSLEDLLFYTIAEGQEKIPVHKFITALKSTGLRTSDPRLKECMDMLRLTLQTTSDGVMLDKDLFKKCVQSNIVLLTQAFRRKFVIPDFMSFTSHIDELYESAKKQSGGKVADYIPQLAKFSPDLWGVSVCTVDGQRHSIGDTKVPFCLQSCVKPLKYAIAVNDLGTEYVHRYVGKEPSGLRFNKLWLNEDDKPHNPMVNAGAIVVTSLIKQGVNNAEKFDYVMQFLNKMAGNEYVGFSNATFQSERESGDRNFAIGYYLKEKKCFPEGTDMVGILDFYFQLCSIEVTCESASVMAATLANGGFCPITGERVLSPEAVRNTLSLMHSCGMYDFSGQFAFHVGLPAKSGVAGGILLVVPNVMGMMCWSPPLDKMGNSVKGIHFCHDLVSLCNFHNYDNLRHFAKKLDPRREGGDQRVKSVINLLFAAYTGDVS | Mouse KGA F327W |

TABLE 1-continued

Full-Length Mutant GLS Proteins

| SEQ ID NO: | Amino Acid Sequence (the activation loop is in bold) | Description |
|---|---|---|
|  | ALRRFALSAMDMEQRDYDSRTALHVAAAEGHVEVVKFLLEACKV NPFPKDRWNNTPMDEALHFGHHDVFKILQEYQVQYTPQGDSDDG KGNQTVHKNLDGLL |  |
| 13 | MMRLRGSAMLRELLLRPPAAVGGVLRRAQPLGTLCRRPRGGSRP AAGLVAAARLHPWWGGGGRAKGPGSGGLSSSPSEILQELGKGGT PPQQQQQQQQQPGASPPAAPGPKDSPGETDAFGNSEGKEMVAAG DNKVKQGLLPSLEDLLFYTIAEGQEKIPVHKFITALKSTGLRTS DPRLKECMDMLRLTLQTTSDGVMLDKDLFKKCVQSNIVLLTQAF RRKFVIPDFMSFTSHIDELYESAKKQSGGKVADYIPQLAKFSPD LWGVSVCTVDGQRHSIGDTKVPFCLQSCVKPLKYAIAVNDLGTE YVHRYVGKEPSGLRFNKLWLNEDDKPHNPMVNAGAIVVTSLIKQ GVNNAEKFDYVMQFLNKMAGNEYVGFSNATFQSERESGDRNFAI GYYLKEKKCFPEGTDMVGILDFYFQLCSIEVTCESASVMAATLA NGGFCPITGERVLSPEAVRNTLSLMHSCGMYDFSGQFAFHVGLP AKSGVAGGILLVVPNVMGMMCWSPPLDKMGNSVKGIHFCHDLVS LCNFHNYDNLRHFAKKLDPRREGGDQRVKSVINLLFAAYTGDVS ALRRFALSAMDMEQRDYDSRTALHVAAAEGHVEVVKFLLEACKV NPFPKDRWNNTPMDEALHFGHHDVFKILQEYQVQYTPQGDSDDG KENQTVHKNLDGLL | Rat KGA F327W |

The central pfam04960 domain in GLS proteins (i.e., residues 244-530 of human GAC/KGA; residues 249-535 of mouse and rat GAC/KGA) is responsible for their glutaminase activity and this domain can function without the N-terminus and/or C-terminus (Thangavelu et al., "Structural Basis for the Active Site Inhibition Mechanism of Human Kidney-Type Glutaminase (KGA)," *Sci. Rep.* 4:3827 (2014), which is hereby incorporated by reference in its entirety). Thus, suitable GLS proteins according to the present technology also include GLS proteins that are less than full-length. In at least one embodiment, the GLS protein comprises a functional pfam04960 domain. The consensus sequence of the wild-type pfam04960 domain has the amino acid sequence of SEQ ID NO:14 (where X at position 32 is Ile or Thr), as follows (the activation loop is underlined).

```
GKVADYIPQL AKFSPDLWGV SVCTVDGQRH SXGDTKVPFC LQSCVKPLKY AIAVNDLGTE    60

YVHRYVGKEP SGLRFNKLFL NEDDKPHNPM VNAGAIVVTS LIKQGVNNAE KFDYVMQFLN   120

KMAGNEYVGF SNATFQSERE SGDRNFAIGY YLKEKKCFPE GTDMVGILDF YFQLCSIEVT   180

CESASVMAAT LANGGFCPIT GERVLSPEAV RNTLSLMHSC GMYDFSGQFA FHVGLPAKSG   240

VAGGILLVVP NVMGMMCWSP PLDKMGNSVK GIHFCHDLVS LCNFHNY                287
```

In at least one embodiment, the mutant GLS protein according to the present technology comprises a mutant pfam04960 domain (i.e., the pfam04960 domain having a phenylalanine to tryptophan substitution at the residue corresponding to position 322 of human GAC). The consensus sequence of the mutant pfam04960 domain has the amino acid sequence of SEQ ID NO:15 (where X at position 32 is Ile or Thr), as follows (the activation loop is underlined).

```
GKVADYIPQL AKFSPDLWGV SVCTVDGQRH SXGDTKVPFC LQSCVKPLKY AIAVNDLGTE    60

YVHRYVGKEP SGLRFNKLWL NEDDKPHNPM VNAGAIVVTS LIKQGVNNAE KFDYVMQFLN   120

KMAGNEYVGF SNATFQSERE SGDRNFAIGY YLKEKKCFPE GTDMVGILDF YFQLCSIEVT   180

CESASVMAAT LANGGFCPIT GERVLSPEAV RNTLSLMHSC GMYDFSGQFA FHVGLPAKSG   240

VAGGILLVVP NVMGMMCWSP PLDKMGNSVK GIHFCHDLVS LCNFHNY                287
```

In at least one embodiment of this aspect of the present technology, the mutant GLS protein comprises the amino acid sequence of SEQ ID NO:8, SEQ ID NO:9, SEQ ID NO:10, SEQ ID NO:11, SEQ ID NO:12, SEQ ID NO:13, or SEQ ID NO:15.

In at least one embodiment of this aspect of the present technology, the mutant GLS protein comprises the amino acid sequence of SEQ ID NO:8, SEQ ID NO:9, SEQ ID NO:10, SEQ ID NO:11, SEQ ID NO:12, SEQ ID NO:13, or SEQ ID NO:15. In at least one embodiment of this aspect of the present technology, the GLS protein comprises an amino acid sequence that is at least about 80%, 85%, 90%, 91%, 92%, 93%, 94%, 95%, 96%, 97%, 98%, 99%, or 100% identical to the amino acid sequence of SEQ ID NO:8, SEQ ID NO:9, SEQ ID NO:10, SEQ ID NO:11, SEQ ID NO:12, SEQ ID NO:13, or SEQ ID NO:15; preferably, the activation loop region has the amino acid sequence KEPSGLRF-NKLW (SEQ ID NO:16). In at least one embodiment of this aspect of the present technology, the GLS protein comprises a functional pfam04960 domain.

Percent identity as used herein refers to the comparison of one amino acid (or nucleic acid) sequence to another, as scored by matching amino acids (or nucleic acids). Percent identity is determined by comparing a statistically significant number of the amino acids (or nucleic acids) from two sequences and scoring a match when the same two amino acids (or nucleic acids) are present at a position. The percent identity can be calculated by any of a variety of alignment algorithms known and used by persons of ordinary skill in the art.

In a preferred embodiment (particularly suitable for use in the methods described infra), the mutant GLS protein is any GLS protein that contains a phenylalanine to tryptophan substitution at the residue corresponding to position 322 of human GAC and that has glutaminase activity. In at least one embodiment, having glutaminase activity means that the mutant GLS protein would be capable of producing a detectable level of glutamate in a method substantially similar to the glutaminase assay described in Example 1, infra.

GLS proteins of the present technology may be produced recombinantly, e.g., from a GLS-encoding nucleic acid molecule, using techniques that are known in the art. Wild-type GLS proteins may be isolated from a sample or tissue by methods commonly used by persons of ordinary skill in the art, or produced recombinantly.

Expression of a GLS protein can be carried out by introducing a nucleic acid molecule encoding the GLS protein into an expression system of choice using conventional recombinant technology. Generally, this involves inserting the nucleic acid molecule into an expression system to which the molecule is heterologous (i.e., not normally present). The introduction of a particular foreign or native gene into a host is facilitated by first introducing the gene sequence into a suitable nucleic acid vector. "Vector" is used herein to mean any genetic element, such as a plasmid, phage, transposon, cosmid, chromosome, virus, virion, etc., which is capable of replication when associated with the proper control elements and which is capable of transferring gene sequences between cells. Thus, the term includes cloning and expression vectors, as well as viral vectors. The heterologous nucleic acid molecule is inserted into the expression system or vector in proper sense (5'→3') orientation and correct reading frame. The vector contains the necessary elements for the transcription and translation of the inserted GLS protein coding sequence.

U.S. Pat. No. 4,237,224 to Cohen and Boyer, which is hereby incorporated by reference in its entirety, describes the production of expression systems in the form of recombinant plasmids using restriction enzyme cleavage and ligation with DNA ligase. These recombinant plasmids are then introduced by means of transformation and replicated in unicellular cultures including prokaryotic organisms and eukaryotic cells grown in tissue culture.

Recombinant genes may also be introduced into viruses, including vaccinia virus, adenovirus, and retroviruses, including lentivirus. Recombinant viruses can be generated by transfection of plasmids into cells infected with virus.

Suitable vectors include, but are not limited to, viral vectors such as lambda vector system gt11, gt WES.tB, and Charon 4, and plasmid vectors such as pBR322, pBR325, pACYC177, pACYC184, pUC8, pUC9, pUC18, pUC19, pLG339, pR290, pKC37, pKC101, SV 40, and pBluescript II SK+/− or KS+/− (see "Stratagene Cloning Systems" Catalog (1993) from Stratagene, La Jolla, Calif., which is hereby incorporated by reference in its entirety), pQE, pIH821, pGEX, pFastBac series (Invitrogen), pET series (see Studier et. al., "Use of T7 RNA Polymerase to Direct Expression of Cloned Genes," *Methods Enzymol.* 185:60-89 (1990), which is hereby incorporated by reference in its entirety), and any derivatives thereof. Recombinant molecules can be introduced into cells via transformation, particularly transduction, conjugation, mobilization, or electroporation. The DNA sequences are cloned into the vector using standard cloning procedures in the art, such as those described in MICHAEL R. GREEN & JOSEPH SAMBROOK, MOLECULAR CLONING: A LABORATORY MANUAL (4$^{th}$ ed. 2012), which is hereby incorporated by reference in its entirety.

A variety of host-vector systems may be utilized to express the GLS protein-encoding sequence in a cell. Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria. The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of prokaryotic promoters. Furthermore, eukaryotic promoters and accompanying genetic signals may not be recognized in or may not function in a prokaryotic system, and, further, prokaryotic promoters are not recognized and do not function in eukaryotic cells.

Similarly, translation of mRNA in prokaryotes depends upon the presence of the proper prokaryotic signals which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the PH promoter, T7 phage promoter, lac promoter, trp promoter, rec A promoter, ribosomal RNA promoter, the $P_R$ and $P_L$ promoters of coliphage lambda and others including, but not limited to, lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in prokaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno sequence about 7-9 bases 5' to the initiation codon (ATG) to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B, or A genes. Additionally, any SD-ATG combination produced by recombinant DNA or other techniques involving incorporation of synthetic nucleotides may be used.

Depending on the vector system and host utilized, any number of suitable transcription and/or translation elements, including constitutive, inducible, and repressible promoters, as well as minimal 5' promoter elements may be used.

The GLS protein-encoding nucleic acid, a promoter molecule of choice, a suitable 3' regulatory region, and if desired, a reporter gene, are incorporated into a vector-expression system of choice to prepare a nucleic acid construct using standard cloning procedures known in the art, such as described in MICHAEL R. GREEN & JOSEPH SAMBROOK, MOLECULAR CLONING: A LABORATORY MANUAL ($4^{th}$ ed. 2012), which is hereby incorporated by reference in its entirety.

The nucleic acid molecule encoding a GLS protein is inserted into a vector in the sense (i.e., 5'→3') direction, such that the open reading frame is properly oriented for the expression of the encoded GLS protein under the control of a promoter of choice. Single or multiple nucleic acids may be ligated into an appropriate vector in this way, under the control of a suitable promoter, to prepare a nucleic acid construct.

Once the isolated nucleic acid molecule encoding the GLS protein has been inserted into an expression vector, it is ready to be incorporated into a host cell. Recombinant molecules can be introduced into cells via transformation, particularly transduction, conjugation, lipofection, protoplast fusion, mobilization, particle bombardment, or electroporation. The DNA sequences are incorporated into the host cell using standard cloning procedures known in the art, as described by Sambrook et al., *Molecular Cloning: A Laboratory Manual*, Second Edition, Cold Springs Laboratory, Cold Springs Harbor, N.Y. (1989), which is hereby incorporated by reference in its entirety. Suitable hosts include, but are not limited to, bacteria, virus, yeast, fungi, mammalian cells, insect cells, plant cells, and the like.

Typically, an antibiotic or other compound useful for selective growth of the transformed cells only is added as a supplement to the media. The compound to be used will be dictated by the selectable marker element present in the plasmid with which the host cell was transformed. Suitable genes are those which confer resistance to gentamycin, G418, hygromycin, puromycin, streptomycin, spectinomycin, tetracycline, chloramphenicol, and the like. Similarly, "reporter genes" which encode enzymes providing for production of an identifiable compound, or other markers which indicate relevant information regarding the outcome of gene delivery, are suitable. For example, various luminescent or phosphorescent reporter genes are also appropriate, such that the presence of the heterologous gene may be ascertained visually.

A second aspect of the present technology relates to a method of screening for compounds that bind to the activation loop of GLS. This method involves contacting mutant GLS protein according to the first aspect of the technology with a test compound. The mutant GLS protein includes an activation loop (containing the phenylalanine to tryptophan substitution) and contacting is carried out under conditions effective to permit binding between the activation loop and the test compound. Fluorescence of the substituted tryptophan is detected in the presence of the test compound and the detected fluorescence is compared to fluorescence of a control. A test compound is then identified as being a compound that binds to the activation loop of GLS based on the compared fluorescence, where a change in fluorescence relative to the control indicates that the test compound binds to the activation loop of GLS.

In carrying out the screening methods of the present technology (including both the second aspect and the third aspect described infra), GLS protein can be provided as described supra. It is also contemplated that mutant and wild-type GLS proteins might now be, or might in future become, commercially available. In such cases, GLS protein could also be provided by purchasing the GLS protein. GLS protein could also be provided by obtaining the protein from a non-commercial source.

Mutant GLS protein suitable for use in this aspect of the present technology includes any mutant GLS protein described supra. In a preferred embodiment, the mutant GLS protein would be capable of emitting a detectable change in tryptophan fluorescence in the presence of BPTES in a method substantially similar to a tryptophan fluorescence assay described in Example 1 infra.

Contacting GLS proteins with test compounds according to the screening methods of the present technology (including both the second aspect and the third aspect described infra) may be carried out using standard methods that will be apparent to the skilled artisan. Typically, the mutant GLS protein will be incubated with the test compound(s) for a time sufficient to allow any reaction (e.g., binding) between the GLS protein and the test compound to reach equilibrium. In at least one embodiment, the protein is incubated with the test compound for a duration of 5 minutes, 10 minutes, 15 minutes, 20 minutes, 30 minutes, or 35 minutes. In a preferred embodiment, the duration is from five to thirty-five minutes or from ten to thirty minutes (e.g., 5-10, 5-15, 5-20, 5-25, 5-30, 5-35, 10-15, 10-20, 10-25, 10-30, 10-35, 15-20, 15-25, 15-30, 15-35, 20-25, 20-30, 20-35, 25-30, 25-35, or 30-35 minutes).

The screening methods of the present technology (including both the second aspect and the third aspect described infra) are typically carried out in vitro.

Suitable test compounds according to the screening methods of the present technology (including both the second aspect and the third aspect described infra) include any compound that potentially binds to the activation loop of GLS protein. In at least one preferred embodiment, the test compound is a bisthiadiazole. In at least one preferred embodiment, the test compound is selected from the group consisting of small inorganic anions and negatively-charged metabolites. As will be apparent to the skilled artisan, all screening methods of the present technology can be carried out using a single test compound or a library of two or more test compounds. If a library of test compounds is used, they can be screened sequentially or simultaneously. If a library of test compounds is used, screening is typically carried out using one type of test compound per well; however, assays in which different test compounds are tested in the same well are also contemplated. In at least one embodiment, a high-throughput screen is carried out using a very large library of test compounds.

As will be understood by the skilled artisan, tryptophan contains a fluorophore. As shown herein, the fluorescence of the substituted tryptophan residue in mutant GLS protein of the present technology emits a fluorescence at a first level (e.g., a particular wavelength or intensity) in the absence of any compounds that bind to the activation loop of the GLS protein. In the screening methods of the present technology (including both the second aspect and the third aspect described infra), candidate compounds can be screened for their ability to cause a detectable change in fluorescence of the substituted tryptophan (e.g., to emit a fluorescence at a level above or below the first level, cause a shift in the fluorescence wavelength or intensity, or cause a change in fluorescence lifetime). In at least one embodiment, candidates are screened for their ability to emit a fluorescence at a level above or below the first level. Detecting a change in fluorescence may be carried out by visual observation. Alternatively, detecting a change in fluorescence may be carried out with a spectrophotometer, or a microscope or macroscope system coupled to a camera or photomultiplier tube. Coupled with proper instrumentation, the optical readout can be followed in real time to obtain spatio-temporal information.

In the screening methods of the present technology (including both the second aspect and the third aspect described infra), the fluorescence of the substituted tryptophan in the presence of the test compound can be compared to a control using any suitable method known in the art. For example, the fluorescence values/intensities themselves can be compared. Alternatively or additionally, the fluorescence values can be used to calculate the binding affinity of the test compound, which can then be compared to that of a control.

In the screening methods of the present technology (including both the second aspect and the third aspect described infra), the control is typically a negative control. To obtain a negative control, the fluorescence of the substituted tryptophan can be determined before and after the test compound is added. Alternatively or additionally, a negative control can be obtained by using another mutant GLS protein that is evaluated in the absence of the test compound but under otherwise substantially identical conditions. In these embodiments, the mutant GLS protein used as the control is typically identical to the protein that is contacted with the test compound (e.g., if human GAC is contacted with the test compound, human GAC is used as the control). In the screening assay according to the second aspect of the present technology, any change in fluorescence (positive or negative) relative to the negative control indicates that the test compound binds to the activation loop of GLS.

Compounds can also be tested for their ability to modulate glutaminase activity of GLS using a glutaminase activity assay. In these assays, GLS protein is contacted with glutamine in the presence of the test compound under conditions effective for the GLS protein, if active, to convert glutamine to glutamate. Production of glutamate, if any, is measured following contacting the GLS protein with glutamine, and the measured glutamate production is compared to glutamate production of a control. A test compound is identified, based on the compared glutamate production, as being a modulator of glutaminase activity of GLS, where a change in glutamate production relative to the control indicates that the test compound modulates glutaminase activity of GLS. Glutamine and the test compound can be added sequentially, in either order, or simultaneously.

As will be apparent to the skilled artisan, by combining the binding assay according to the second aspect of the technology with a glutaminase activity assay, compounds that both bind to the activation loop and are capable of modulating glutaminase activity of GLS can be identified. As will also be apparent to the skilled artisan, the binding assay and the glutaminase activity assay could be performed sequentially, in either order, or simultaneously.

In at least one embodiment, the binding assay is performed before the glutaminase activity assay. In this embodiment, the second aspect of the present technology further includes identifying a compound that also modulates glutaminase activity of GLS. In this embodiment, a compound identified as being a compound that binds to the activation loop is selected. GLS protein is contacted with glutamine in the presence of the selected test compound under conditions effective for the GLS protein, if active, to convert glutamine to glutamate. Production of glutamate, if any, is measured following contacting the GLS protein with glutamine in the presence of the selected test compound, and the measured glutamate production is compared to glutamate production of a control. A selected test compound is further identified to also be a modulator of glutaminase activity of GLS based on the compared glutamate production, where a change in glutamate production relative to the control indicates that the selected test compound also modulates glutaminase activity of GLS.

Contacting in the glutaminase activity assays described herein may be carried out as described above.

In the glutaminase activity assays described herein, GLS protein is used to screen for the test compound's effect on activity. As will be apparent to the skilled artisan, because a glutaminase activity assay does not rely on the fluorescence of a substituted tryptophan, any GLS protein that is capable of converting glutamine to glutamate is suitable for use in the glutaminase activity assays described herein. Thus, the GLS protein used in the glutaminase activity assay can be mutant GLS protein of the present technology or GLS protein that does not have a phenylalanine to trytophan substitution.

As will be apparent to the skilled artisan, any suitable method known in the art for measuring the production of glutamate can be used in the glutaminase activity assays described herein. Active glutaminase converts glutamine to glutamate and ammonia. Glutaminase activity can be monitored by measuring production of either of the products of the reaction, glutamate or ammonia. Because glutamate is not spectroscopic, glutamate production is typically measured using a coupled enzymatic reaction in which GLS catalyzes a first reaction to produce glutamate and ammonia, and a second enzyme catalyzes a second reaction using the glutamate or ammonia produced in the first reaction to reflect the activity of the first reaction (i.e., the glutaminase activity). Coupled enzymatic reactions are well known in the art and include, but are not limited to, those using glutamate dehydrogenase, which catalyzes the reversible reaction of glutamate and NAD(+) into α-ketoglutarate, NADH, and ammonia. Kits for performing suitable coupled enzymatic assays are widely available and include, for example, the Glutaminase (GLS) Assay Kit (Biomedical Research Service and Clinical Application), the Glutamate Assay Kit (Abcam), the Ammonia Assay Kit (Abcam), the NADH fluorescence assay described in Example 1 below, and the fluorescence-based assay described in Mihali et al., "High-Throughput Screening of Glutaminase Inhibitors For the Pharmacotherapy of Schizophrenia: Implementation of a Fluorescence-Based Assay," *Columbia Undergraduate Science Journal* 4 (2009), which is hereby incorporated by reference in its entirety.

As will also be apparent to the skilled artisan, glutaminase activity assays typically use a negative control. To obtain a negative control, glutamate production can be determined before and after the test compound is added. Alternatively or additionally, a negative control can be obtained in a separate reaction using GLS protein that is evaluated in the absence of the test compound but under otherwise substantially identical conditions. In these embodiments, the GLS protein used as the control is typically identical to the protein that is contacted with the test compound (e.g., if wild-type human GAC is contacted with the test compound, wild-type human GAC is used as the control). An increase in glutamate production relative to the negative control indicates that the test compound is an activator of GLS activity, while a decrease in glutamate production relative to the negative control indicates that the test compound is an inhibitor of GLS activity.

A third aspect of the present technology relates to a method of screening for compounds that potentially modulate glutaminase activity of GLS. This method involves contacting mutant GLS protein according to the first aspect of the technology with a test compound. The mutant GLS protein includes an activation loop (containing the phenylalanine to tryptophan substitution) and contacting is carried out under conditions effective to permit binding between the activation loop and the test compound. Fluorescence of the substituted tryptophan is detected in the presence of the test compound and the detected fluorescence is compared to fluorescence of a control. A test compound is then identified as being a potential modulator of glutaminase activity of GLS based on the compared fluorescence, where a change in fluorescence relative to the control indicates that the test compound potentially modulates glutaminase activity of GLS.

In carrying out this any all other methods of the present technology, GLS protein can be provided as described supra.

Mutant GLS protein suitable for use in this aspect of the present technology includes any mutant GLS protein described supra. In a preferred embodiment, the mutant GLS protein would be capable of emitting a detectable change in tryptophan fluorescence in the presence of BPTES in a method substantially similar to a tryptophan fluorescence assay described in Example 1 infra.

Contacting may be carried out as described above.

Suitable test compounds are as described above.

As described above, candidate compounds can be screened for their ability to cause a detectable change in fluorescence of the substituted tryptophan and compared to a control. This can be carried out as described above, except that in the screening assay according to this aspect of the present technology, a change in fluorescence (positive or negative) relative to the control indicates that the test compound potentially modulates (inhibits or activates) glutaminase activity of GLS. An increase in fluorescence relative to a negative control indicates that the test compound is a potential activator of GLS activity, while a decrease in fluorescence relative to a negative control indicates that the test compound is a potential inhibitor of GLS activity.

As will be apparent to the skilled artisan, the screening assay according to the third aspect of the present technology can also be combined with a glutaminase activity assay, as described supra. The glutaminase activity assay according to this embodiment may be carried out as described above. As will be apparent to the skilled artisan, by combining the screening assay according to the third aspect of the technology with a glutaminase activity assay, compounds that are capable of modulating glutaminase activity of GLS can be identified. As will also be apparent to the skilled artisan, the screening assay and the glutaminase activity assay could be performed sequentially or simultaneously.

In at least one embodiment, the screening assay according to the third aspect of the technology is performed before the glutaminase activity assay. In this embodiment, the third aspect of the present technology further includes verifying whether a test compound modulates glutaminase activity of GLS. In this embodiment, a compound identified as being a potential modulator of glutaminase activity of GLS is selected. GLS protein is contacted with glutamine in the presence of the selected test compound under conditions effective for the GLS protein, if active, to convert glutamine to glutamate. Production of glutamate, if any, is measured following the contacting with glutamine in the presence of the selected test compound, and the measured glutamate production is compared to glutamate production of a control. A selected test compound is further verified to be a modulator of glutaminase activity of GLS based on the compared glutamate production, where a change in glutamate production relative to the control indicates that the selected test compound modulates glutaminase activity of GLS.

A fourth aspect of the present technology relates to a kit for identifying a compound that binds to the activation loop of GLS and/or potentially modulates glutaminase activity of GLS. The kit includes any mutant GLS protein described supra. In a preferred embodiment, the mutant GLS protein would be capable of emitting a detectable change in tryptophan fluorescence in the presence of BPTES in a method substantially similar to a tryptophan fluorescence assay described in Example 1 infra.

In at least one embodiment of this aspect of the present technology, the the mutant GLS protein comprises the amino acid sequence of SEQ ID NO:8, SEQ ID NO:9, SEQ ID NO:10, SEQ ID NO:11, SEQ ID NO:12, SEQ ID NO:13, or SEQ ID NO:15. In at least one embodiment of this aspect of the present technology, the GLS protein comprises an amino acid sequence that is at least about 80%, 85%, 90%, 91%, 92%, 93%, 94%, 95%, 96%, 97%, 98%, 99%, or 100% identical to the amino acid sequence of SEQ ID NO:8, SEQ ID NO:9, SEQ ID NO:10, SEQ ID NO:11, SEQ ID NO:12, SEQ ID NO:13, or SEQ ID NO:15; preferably, the activation loop region has the amino acid sequence KEPSGLRF-NKLW (SEQ ID NO:16). In at least one embodiment of this aspect of the present technology, the GLS protein comprises a functional pfam04960 domain.

In at least one embodiment, the kit also includes one or more test compounds. Suitable test compounds include those described above.

The present technology may be further illustrated by reference to the following examples.

EXAMPLES

Example 1—Materials and Methods

Abbreviations

Abbreviations used herein include: GLS, kidney-type mitochondrial enzyme glutaminase; GDH, glutamate dehydrogenase; GOT, glutamic-oxaloacetic transaminase; GPT, glutamic-pyruvic transaminase; mTOR, mechanistic target of rapamycin; KGA, kidney-type glutaminase; DON, diazo-O-norleucine; BPTES, (bis-2-(5-phenylacetamido-1,2,4-thiadiazol-2-yl)ethyl; SEC, size exclusion chromatography; MALS, multiangle light scattering; GAC, glutaminase C.
Preparation of Recombinant GAC GAC was expressed and purified as described previously (Stalnecker et al., "Mechanism by Which a Recently Discovered Allosteric Inhibitor Blocks Glutamine Metabolism in Transformed Cells," *Proc. Natl. Acad. Sci. U.S.A.* 112: 394-99 (2015), which is hereby incorporated by reference in its entirety). Briefly, a plasmid encoding the mouse kidney-type glutaminase isoform 2 (GAC, NP_001106854.1 (which is hereby incorporated by reference in its entirety), residues 73-603) was cloned into a pET28a vector containing an N-terminal histidine (His) tag and thrombin cleavage site. The expressed protein was purified using $Co^2$ affinity beads (Clontech), followed by anion exchange (GE Healthcare) and gel filtration chromatography. Purified GAC was stored in a high salt-containing buffer (20 mM Tris-HCl (pH 8.5), 500 mM NaCl, and 1 mM $NaN_3$) at $-80°$ C. following snap-freezing in liquid $N_2$ for long-term use.

The $GAC_{F327W}$ mutant was obtained using site-directed mutagenesis. Purification of the protein was performed as described for WT GAC above.
Protein Labeling with FRET Pairs Labeling recombinant GAC with small molecule probes was performed by methods described previously (Stalnecker et al., "Mechanism by Which a Recently Discovered Allosteric Inhibitor Blocks Glutamine Metabolism in Transformed Cells," *Proc. Natl. Acad. Sci. U.S.A.* 112:394-99 (2015), which is hereby incorporated by reference in its entirety). Briefly, 1.5 mg of GAC was first exchanged into 50 mM HEPES (pH 7.2) and 100 mM NaCl (labeling buffer) using a PD10 desalting column (GE Healthcare). The protein was then incubated with either 50 M (5-fold excess over enzyme) Alexa Fluor 488 succinimidyl ester or QSY9 succinimidyl ester (Molecular Probes) for 1 hour at 4° C. The labeling reaction was quenched with 150 mM Tris-HCl (pH 8.5), and unreacted probe was separated from labeled enzyme using a PD10 desalting column, eluting labeled GAC into the high salt-containing buffer.
MALS Analysis Purified GAC and GAC mutants were subjected to MALS as described previously (Møller et al., "Small Angle X-Ray Scattering Studies of Mitochondrial Glutaminase C Reveal Extended Flexible Regions, and Link Oligomeric State with Enzyme Activity," *PLoS ONE* 8:e74783 (2013), which is hereby incorporated by reference in its entirety). Briefly, 50-μl samples of 5 mg/ml GAC with or without 30-min preincubation with 100 M BPTES were injected onto a BioSep-SEC-S4000 size exclusion column (Wyatt Technology) coupled to a static 18-angle light scattering detector (DAWN HELEOS-II) and a refractive index detector (Opti-Lab T-rEX, Wyatt Technology) at 23° C. The size exclusion column was equilibrated with 20 mM Tris-HCl (pH 8.5) and 200 mM NaCl and, when appropriate, 50 mM $K_2HPO_4$ or $K_2SO_4$. The flow rate was kept at 1 ml/min. Root mean square radius and mass distribution (poly-dispersity) were analyzed using ASTRA software, with monomeric BSA (Sigma) serving to normalize the light-scattering signal.
Glutaminase Assays Activity assays used to evaluate the activity of GAC mutants and inhibition by BPTES and CB-839 followed a two-step protocol adapted from Robinson et al. (Robinson et al., "Novel Mechanism of Inhibition of Rat Kidney-Type Glutaminase by Bis-2-(5-Phenylacetamido-1,2,4-Thiadiazol-2-yl)Ethyl Sulfide (BPTES)," *Biochem. J.* 406:407-14 (2007), which is hereby incorporated by reference in its entirety). For example, when assaying phosphate- or sulfate-stimulated activity, 20 μl of 20 mM glutamine, 50 mM Tris acetate (pH 8.5), and 0.1 mM EDTA, containing the indicated concentrations of $K_2HPO_4$ or $K_2SO_4$, were added to a UV-transparent Costar 96-well plate (Corning). For inhibition assays, drugs dissolved in DMSO were added to 20 μl of 20 mM glutamine, 50 mM Tris acetate (pH 8.5), 0.1 mM EDTA, and 50 mM $K_2HPO_4$. To initiate the reaction, 5 μl of a solution of GAC prepared in 20 mM Tris-HCl (pH 8.5), 100 mM NaCl, and 1 mM $NaN_3$, to give a final enzyme concentration of 50 nM in the assay, or a GAC concentration of 100 nM for inhibition assays, was added to the glutamine solution and incubated at 23° C. for 2 min before the reaction was quenched using 2.5 μl of 3 M HCl. The second step was initiated by addition of 200 μl of 12 units/pi GDH, 2 mM NAD, 100 mM hydrazine (Sigma), and 100 mM Tris-HCl (pH 9.2) on top of the first quenched reaction and incubated for 45 min at 23° C. before reading NADH absorbance. Glutamate produced by the first reaction was determined from the amount of NADH generated in the second reaction by using the extinction coefficient for NADH (6220 $M^{-1}$ $cm^{-1}$).
Fluorescence Measurements Fluorescence experiments were performed with a Varian Cary Eclipse fluorimeter in counting mode, using 1 ml samples with continuous stirring at 20° C. in 50 mM Tris acetate (pH 8.5) and 0.1 mM EDTA. For FRET assays, 75 nM QSY9-labeled GAC was added to 25 nM 488-labeled GAC while monitoring fluorescence emission at 520 nm with excitation at 490 nm. After equilibration for 10 min, 100 mM $K_2HPO_4$ or $K_2SO_4$, or either 500 nM BPTES or CB-839, was added and equilibrated for 5 min. Finally, 1 M unlabeled WT GAC was added to the assay incubation. For tryptophan emission scans, the excitation and emission wavelengths were 285 and 310-390 nm, respectively. For kinetic experiments, the excitation and emission wavelengths were 285 and 340 nm, respectively. For drug titrations, BPTES and CB-839 at the indicated concentrations were added to 100 nM $GAC_{F327W}$ to give less than 0.5% (v/v) DMSO. Points for the dose-dependent quenching by inhibitors were taken from the equilibrated binding curves and fit to a bimolecular ligand binding equation after correcting for fractional saturation using the relation of free and unbound enzyme/drug complex (i.e., $f_{bound}+f_{free}=1$, where $f_{bound}=F/F_{max}$). Similarly, 1 M BPTES was added to 100 nM $GAC_{F327W,D391K}$. For allosteric activator titrations, the indicated concentrations of $K_2HPO_4$ or $K_2SO_4$ were added to 500 nM $GAC_{F327W}$.

Figure 2:
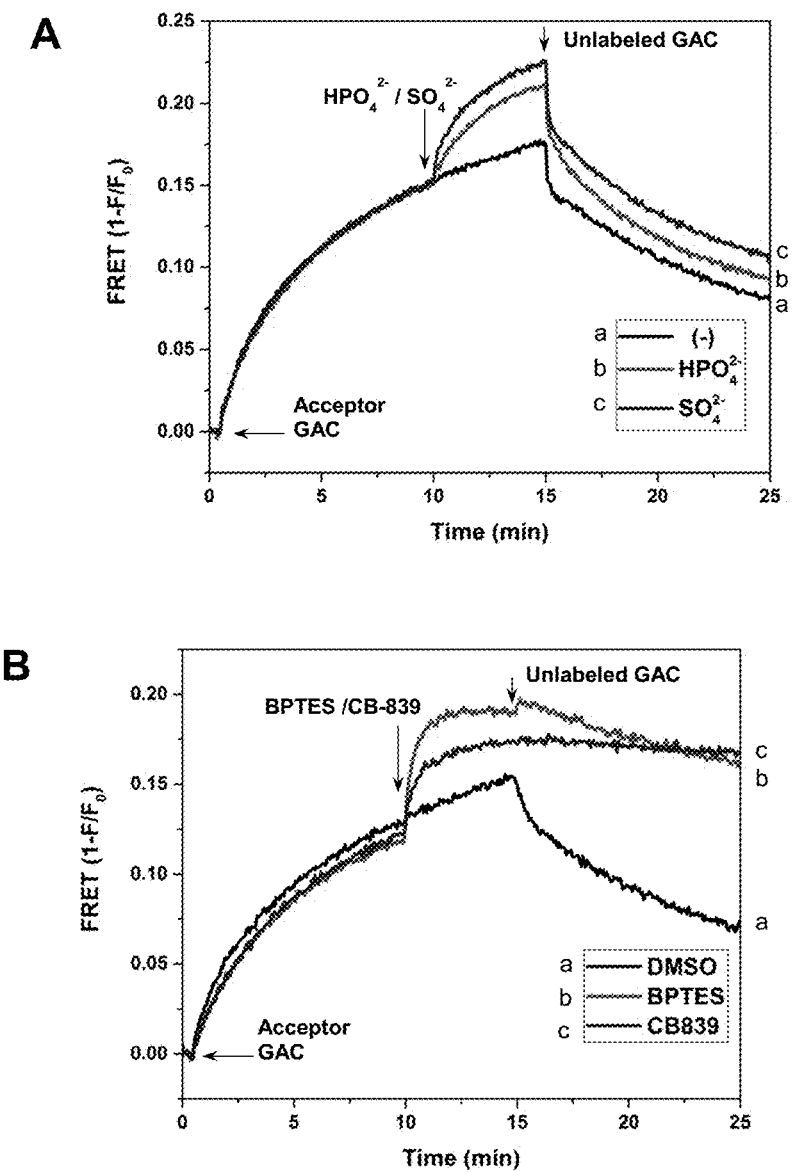
FIGS. 2A-B demonstrate that both allosteric activators and BPTES class inhibitors induce GAC tetramer formation.
Figure 3:
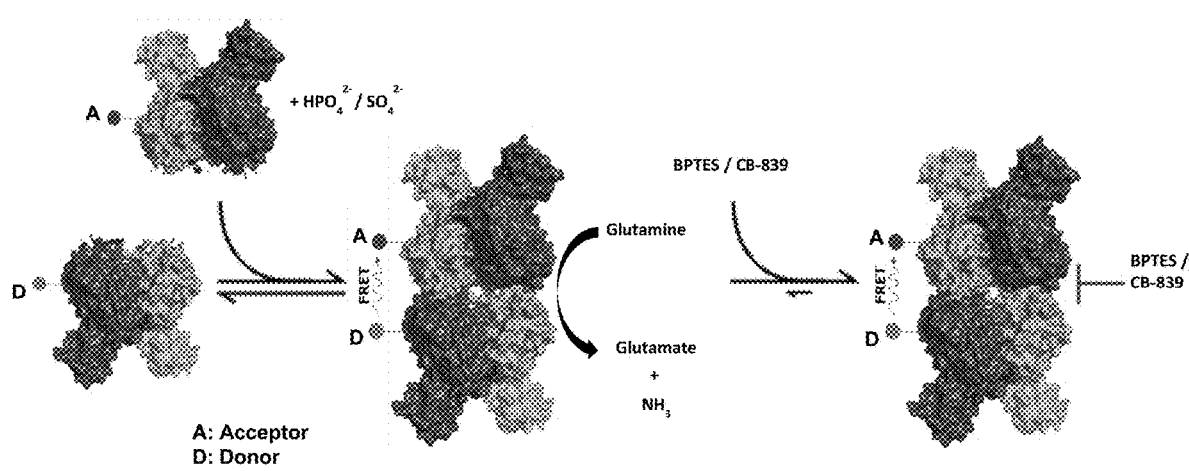
FIG. 3 is a schematic diagram illustrating the transition from a GAC dimer to a tetramer, where the tetramer species is depicted to give rise to the FRET signal and as being the active species. 488-labeled (D, green) GAC is the FRET donor, and QSY9-labeled (A, purple) GAC is the FRET acceptor. The allosteric activators inorganic phosphate ($HPO_4^{2-}$) and sulfate ($SO_4^{2-}$) are depicted to promote the dimer-to-tetramer transition to emphasize their ability to activate GAC, whereas the inhibitors BPTES and CB-839 bind to the FRET pairs at the dimer-dimer interface, forming a stable BPTES or CB-839-bound inactive GAC tetramer (BPTES is shown as green spheres).

Example 2—Comparison of the Effects of Allosteric Activators and BPTES Class Inhibitors on GAC Previous studies have demonstrated the requirement for both KGA and GAC to form homo-tetramers to become activated (Stalnecker et al., "Mechanism by Which a Recently Discovered Allosteric Inhibitor Blocks Glutamine Metabolism in Transformed Cells," *Proc. Natl. Acad. Sci. U.S.A.* 112:394-99 (2015); Møller et al., "Small Angle X-Ray Scattering Studies of Mitochondrial Glutaminase C Reveal Extended Flexible Regions, and Link Oligomeric State with Enzyme Activity," *PLoS ONE* 8:e74783 (2013); Curthoys et al., "Regulation of Renal Ammoniagenesis: Purification and Characterization of Phosphate-Dependent Glutaminase from Rat Kidney," *Arch. Biochem. Biophys.* 174:82-89 (1976); McGivan et al., "Rat Liver Glutaminase," *Eur. J. Biochem.* 148:323-27 (1985), each of which is hereby incorporated by reference in its entirety). Using a FRET assay, the effects that allosteric activators and inhibitors (FIG. 1) have on GAC tetramer formation were able to be monitored in real time. An increase in the degree of FRET by the addition of the allosteric activators inorganic phosphate ($HPO_4^{2-}$) and sulfate ($SO_4^{2-}$) was observed (FIG. 2A). The phosphate/sulfate-bound GAC tetramers were found to be readily reversible upon addition of excess unlabeled GAC subunits, which compete with the GAC FRET pairs, resulting in a decreased FRET signal. Similarly, addition of the allosteric inhibitors BPTES and CB-839 to GAC labeled with FRET pairs increased the FRET readout, reflecting the rapid formation of tetramers upon the binding of these inhibitors (FIG. 2B). However, in the presence of either BPTES or CB-839, GAC tetramers were resistant to dissociation following the addition of excess unlabeled GAC subunits, demonstrating the formation of stable inhibitor-bound tetramers. Under the same conditions, in the absence of either BPTES or CB-839, the addition of excess unlabeled GAC resulted in the ready exchange of dimeric subunits and the effective dilution of donor-acceptor FRET pairs (FIG. 2B, compare black (DMSO) versus blue (CB-839) and red (BPTES) curves). Notably, CB-839-bound GAC tetramers labeled with FRET pairs were more resistant to dissociation compared with their BPTES-bound GAC counterparts (FIG. 2B, compare blue (CB-839) versus red (BPTES)). GAC tetramer formation, which underlies the FRET changes and the stabilization provided by anions that stimulate glutaminase activity (i.e., $SO_4^{2-}$ and $HPO_4^{2-}$), or by inhibitors that enhance the formation and stability of GAC tetramers (i.e., BPTES and CB-839), are summarized schematically in FIG. 3.

The ability of BPTES and CB-839 to inhibit recombinant GAC activity was compared by monitoring the NADH fluorescence generated as an outcome of the coupled reactions used to assay the enzyme (Stalnecker et al., "Mechanism by Which a Recently Discovered Allosteric Inhibitor Blocks Glutamine Metabolism in Transformed Cells," *Proc. Natl. Acad. Sci. U.S.A.* 112:394-99 (2015), which is hereby incorporated by reference in its entirety). FIG. 4A shows a direct comparison of the inhibition by BPTES and CB-839 following initiation of the reaction by the addition of glutamine but prior to the addition of the activator $HPO_4^{2-}$. Consistent with the increased stability of the GAC tetramer conferred by CB-839 compared with BPTES in GAC FRET assays (FIG. 2B, compare red versus blue traces), tetramers that formed in the presence of CB-839 were more resistant to subsequent activation by inorganic phosphate (compare red (BPTES) and blue (CB-839) traces in FIG. 4A to red (BPTES) and blue (CB-839) traces following addition of unlabeled GAC in FIG. 2B). The relative phosphate-stimulated activity is shown in FIG. 4B, where an initial rate analysis reveals a stronger inhibition by CB-839 compared with the same concentration of BPTES upon stimulation by an excess of allosteric activator.

Given the inhibitory properties of the BPTES class of molecules toward GAC and the established link between the degree of cellular glutaminase activity and glutamine dependence in cancer cell lines (Lukey et al., "The Oncogenic Transcription Factor c-Jun Regulates Glutaminase Expression and Sensitizes Cells to Glutaminase-Targeted Therapy," *Nat. Commun.* 7:11321 (2016), which is hereby incorporated by reference in its entirety), there was interest in establishing an assay to probe the direct binding of these inhibitors to the enzyme and the underlying mechanisms by which they influence catalytic activity. Of particular interest was to better understand how they interact with the activation loop within the dimer-dimer interface of GAC, where BPTES has been shown to bind based on X-ray crystallographic studies, and how such interactions inhibit the enzyme. Thus, a fluorescence reporter group within the flexible activation loop was engineered to monitor its real-time movements in response to allosteric inhibitors and to compare such effects to those elicited by allosteric activators.

Example 3—Examination of the BPTES Binding Site Based on X-Ray Crystal Structures With respect to their ability to drive GAC tetramer formation, both inhibitors and activators result in similar FRET increases and yet elicit opposite outcomes regarding their effects on enzyme activity. To examine this at a structural level, the available X-ray crystal structures for GAC and KGA were compared. Currently, there are 16 high-resolution X-ray crystal structures for these GLS isoforms. It is important to note that KGA and GAC differ only in their C-terminal sequences, which are unresolved in all X-ray crystal structures. Upon careful analysis, only six of these structures provide sufficient electron density to resolve unambiguously the atomic positions of some of the residues within the activation loop (i.e., residues $^{320}$GLRFNKL$^{326}$ (SEQ ID NO:17)) (Thangavelu et al., "Structural Basis for the Allosteric Inhibitory Mechanism of Human Kidney-Type Glutaminase (KGA) and Its Regulation by Raf-Mek-Erk Signaling in Cancer Cell Metabolism," *Proc. Natl. Acad. Sci. U.S.A.* 109:7705-10 (2012); DeLaBarre et al., "Full-Length Human Glutaminase in Complex with an Allosteric Inhibitor," *Biochemistry* 50:10764-70 (2011); Cassago et al., "Mitochondrial Localization and Structure-Based Phosphate Activation Mechanism of Glutaminase C with Implications for Cancer Metabolism," *Proc. Natl. Acad. Sci. U.S.A.* 109:1092-97 (2012), each of which is hereby incorporated by reference in its entirety). Of those structures with a resolved activation loop, four are co-crystal structures with BPTES (PDB codes 3VOZ, 3VP1, 3UO9, and 4JKT), one is a co-crystal structure with the active site inhibitor DON (PDB code 4O7D), and the other is without either BPTES or DON but includes two inorganic anions of sulfate per KGA monomer (PDB code 3VOY). Interestingly, in this KGA structure (PDB code 3VOY), one sulfate is bound proximal to the activation loop through interactions formed directly with tyrosine 399 and lysine 403 and represents the likely binding site for allosteric activators, although this has not been directly demonstrated.

Significant differences were noted when comparing the two KGA/GAC structures that lack bound BPTES but have a sufficiently resolved activation loop (PDB codes 4O7D and 3VOY) with all BPTES-bound structures. To illustrate this, FIG. 5A presents a space-filling model of a DON-bound GAC tetramer (PDB code 4O7D), which has been aligned with the BPTES/$SO_4^{2-}$-bound GAC structure (3VOZ), to show the binding sites for BPTES and sulfate. The marked changes in the orientation of the activation loop are illustrated in FIG. 5B, with the loop in the DON-bound GAC complex (cyan) being significantly displaced relative to its position in the BPTES-bound GAC structure (magenta). The displacement of the activation loop represents the extremes of the available conformational states observed in the KGA/GAC X-ray crystal structures to date, where the loop assumes a variety of conformations. It was reasoned that it might be possible to observe this conformational transition in real time by replacing a wild-type residue with the amino acid tryptophan, i.e., to use it as a fluorescent reporter group. With this in mind, three residues were selected for tryptophan substitution: specifically, Phe-323, Phe-327, and Tyr-399. Both Phe-323 and Phe-327 are significantly displaced in the BPTES-bound structures (FIG. 5B, the Phe-327 movement is indicated by the red arrow), and Tyr-399 is directly adjacent to the thiadiazole ring of BPTES. These residues have been shown previously to be critical for the activation of the KGA/GAC enzymes as well as for the inhibition of their activity by BPTES (McDonald et al., "Effect of Lysine to Alanine Mutations on the Phosphate Activation and BPTES Inhibition of Glutaminase," *Neurochem. Int* 88:10-14 (2015); Ferreira et al., "Active Glutaminase C Self-Assembles into a Supratetrameric Oligomer That Can Be Disrupted by an Allosteric Inhibitor," *J. Biol. Chem.* 288:28009-20 (2013), each of which is hereby incorporated by reference in its entirety).

Example 4—the F327W Mutation is Sensitive to Inhibitor Binding

Upon individual substitution of these three residues to tryptophan, their fluorescence properties (excitation, 285 nm; emission, 310-390 nm) were initially analyzed before and after the addition of BPTES. It was found that BPTES induced a marked quenching in the tryptophan fluorescence of the $GAC_{F327W}$ mutant (FIG. 6B, compare black with red curves), whereas it did not change the fluorescence emission of WT GAC (FIG. 6A) or the F323W or Y399W mutants (data not shown). The molecular size of WT GAC and the individual tryptophan mutants was then determined in the absence and presence of BPTES using multiangle light scattering (MALS) downstream of size exclusion chromatography (SEC). Significant shifts in the molecular weight distribution for the F327W mutant and WT GAC were observed following their preincubation with BPTES (FIG. 6C and FIG. 6D; solid lines represent elution of GAC, and broken lines represent the calculated molecular weight). The comparable increases in the mean molecular weights of WT GAC and the F327W mutant following preincubation with BPTES further demonstrate that the F327W mutant is able to bind to and form complexes with the inhibitor molecule in a manner similar to the wild-type enzyme. Additionally, this mutant exhibited Vmax and $K_M$ values for phosphate-stimulated activity that closely matched those of WT GAC (FIG. 6E), further demonstrating the functional equivalence of $GAC_{F327W}$ with the wild-type protein.

Based on the available crystallographic data, the ability of the F327W mutation to read out BPTES binding is likely due to the interactions of the inhibitor with the peptide backbone of the substituted tryptophan and not the outcome of direct contact with the indole side chain (FIG. 7A). Consistent with this, the orientation of the native phenylalanine in the BPTES-bound GAC structures indicates that the phenylalanine side chain does not interact with other residues. Alternatively, DeLaBarre et al. described the electrostatic interaction of BPTES with the peptide backbone of residues Leu-326 and Phe-327 (DeLaBarre et al., "Full-Length Human Glutaminase in Complex with an Allosteric Inhibitor," *Biochemistry* 50:10764-70 (2011), which is hereby incorporated by reference in its entirety). These interactions are formed between the peptide backbone and the nitrogen atoms within the thiadiazole ring of BPTES (FIG. 7A, dotted lines). Others have reported the observed electrostatic interaction between BPTES and the peptide backbone of these two residues but involving the sulfur atom of the thiadiazole ring of BPTES rather than its nitrogen moieties (FIG. 7B) (Thangavelu et al., "Structural Basis for the Allosteric Inhibitory Mechanism of Human Kidney-Type Glutaminase (KGA) and Its Regulation by Raf-Mek-Erk Signaling in Cancer Cell Metabolism," *Proc. Natl. Acad. Sci. U.S.A.* 109:7705-10 (2012); Cassago et al., "Mitochondrial Localization and Structure-Based Phosphate Activation Mechanism of Glutaminase C with Implications for Cancer Metabolism," *Proc. Natl. Acad. Sci. U.S.A.* 109:1092-97 (2012), each of which is hereby incorporated by reference in its entirety). The requirement of BPTES analogs to possess a thiadiazole ring has been shown to be necessary to maintain potency (Robinson et al., "Novel Mechanism of Inhibition of Rat Kidney-Type Glutaminase by Bis-2-(5-Phenylacetamido-1,2,4-Thiadiazol-2-yl)Ethyl Sulfide (BPTES)," *Biochem. J.* 406:407-14 (2007); U.S. Pat. No. 6,451,828; Shukla et al., "Design, Synthesis, and Pharmacological Evaluation of Bis-2-(5-Phenylacetamido-1,2,4-Thiadiazol-2-yl)Ethyl Sulfide 3 (BPTES) Analogs as Glutaminase Inhibitors," *J. Med. Chem.* 55:10551-63 (2012), each of which is hereby incorporated by reference in its entirety). The interactions depicted in these two bound BPTES orientations suggest that the molecular basis for the observed changes in $GAC_{F327W}$ tryptophan emission, upon activation loop repositioning, results from the interaction of the loop with the thiadiazole group present in both BPTES and CB-839.

Example 5—Changes in F327W Fluorescence Provide a Direct Binding Readout for BPTES and CB-839

Figure 8C:
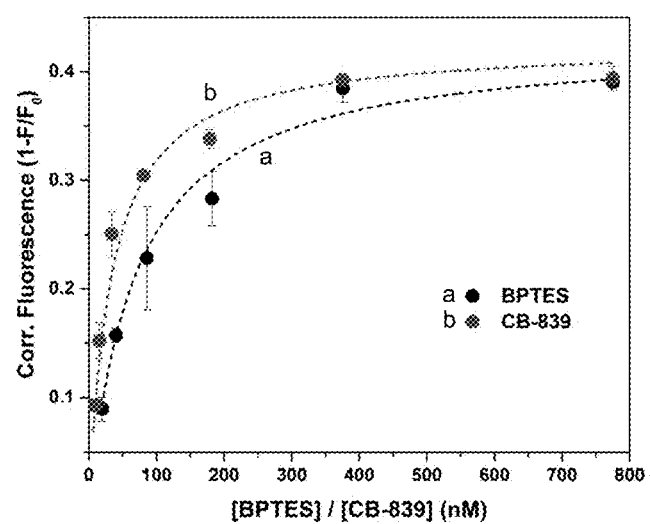

Derivatives of BPTES have proven to be effective inhibitors in vivo, with compound CB-839 being the most potent to date with a reported $IC_{50}$ value of −30 nM (Gross et al., "Antitumor Activity of the Glutaminase Inhibitor CB-839 in Triple-Negative Breast Cancer," *Mol. Cancer Ther.* 13:890-901 (2014), which is hereby incorporated by reference in its entirety). However, unlike BPTES, CB-839 achieved its maximal potency only when pre-incubated with GAC prior to assaying enzyme activity, suggesting that it has a slower rate of association with the enzyme (i.e., a slower on rate (Gross et al., "Antitumor Activity of the Glutaminase Inhibitor CB-839 in Triple-Negative Breast Cancer," *Mol. Cancer Ther.* 13:890-901 (2014), which is hereby incorporated by reference in its entirety)). Similarly, CB-839 appeared to dissociate more slowly from GAC compared with BPTES (i.e., a slower off rate (Gross et al., "Antitumor Activity of the Glutaminase Inhibitor CB-839 in Triple-Negative Breast Cancer," *Mol. Cancer Ther.* 13:890-901 (2014), which is hereby incorporated by reference in its entirety)). By monitoring the tryptophan fluorescence of the F327W mutant, the kinetics and binding efficiencies of these two inhibitors were able to be directly compared. As shown in FIGS. 8A-B, the addition of BPTES or CB-839 to the F327W mutant resulted in a dose-dependent quenching of tryptophan fluorescence. Each inhibitor reached equilibrium within 10 min, with CB-839 displaying slower binding kinetics than BPTES. The binding isotherms for the two inhibitors yielded $K_D$ values of 34±5 nM for CB-839 and 70±5 nM for BPTES (FIG. 8C). Thus, the binding affinities of these two inhibitors for GAC are more similar than the effects they show on the initial rates of phosphate-stimulated enzyme activity (FIGS. 4A-B) or when comparing their $IC_{50}$ values (i.e., 23±1 nM for CB-839 versus 108±17 nM for BPTES; data not shown). As described in Example 8 below, the differences observed between the direct binding and enzyme activity assays may reflect the differences in the on and off rates for the two inhibitors.

Example 6—BPTES Requires Tetramer Formation to Bind to GAC

To demonstrate the requirement of BPTES to bind to the tetrameric form of GAC, D391K, a mutation along the dimer-dimer interface that was shown previously to block the ability of GAC to form tetramers (Stalnecker et al., "Mechanism by Which a Recently Discovered Allosteric Inhibitor Blocks Glutamine Metabolism in Transformed Cells," *Proc. Natl. Acad. Sci. U.S.A.* 112:394-99 (2015), which is hereby incorporated by reference in its entirety), was taken advantage of. Aspartate 391 is critical for GAC tetramer formation, where it forms a salt bridge with Lys-401 (both residues reside at the interface between two GAC dimers). Because of the twofold axis of symmetry of the GAC tetramer, the single change of aspartate 391 to lysine, and hence the introduction of a charge-charge repulsion, results in the disruption of four salt bridges per GAC tetramer that is sufficient to prohibit tetramer formation (Stalnecker et al., "Mechanism by Which a Recently Discovered Allosteric Inhibitor Blocks Glutamine Metabolism in Transformed Cells," *Proc. Natl. Acad. Sci. U.S.A.* 112: 394-99 (2015), which is hereby incorporated by reference in its entirety). To investigate whether BPTES binds to the activation loop of an inactive GAC dimer, the D391K mutation was introduced into the $GAC_{F327W}$ background, and it was found that this single substitution completely ablated the ability of BPTES to induce a change in tryptophan fluorescence (FIG. 9A, compare the red and black curves). The $GAC_{F327W,D391K}$ double mutant was further examined using SEC-MALS to confirm that it existed in a dimeric state both with and without pre-incubation of BPTES. It was found that the GAC double mutant indeed exhibited a molecular weight distribution consistent with a dimer, in the presence and absence of BPTES, thus further illustrating the requirement of a GAC tetramer to form for BPTES to bind and induce an inhibitory state (FIG. 9B, solid lines represent elution of GAC, and broken lines represent the measured molecular weight).

Example 7—Allosteric Activators Enhance $GAC_{F327W}$ Fluorescence

Previous studies of the activation of the KGA/GAC enzymes revealed that their enzymatic activity was markedly increased upon addition of various inorganic anionic ions (Robinson et al., "Novel Mechanism of Inhibition of Rat Kidney-Type Glutaminase by Bis-2-(5-Phenylacetamido-1,2,4-Thiadiazol-2-yl)Ethyl Sulfide (BPTES)," *Biochem. J.* 406:407-14 (2007); Møller et al., "Small Angle X-Ray Scattering Studies of Mitochondrial Glutaminase C Reveal Extended Flexible Regions, and Link Oligomeric State with Enzyme Activity," *PLoS ONE* 8:e74783 (2013); Curthoys et al., "Regulation of Renal Ammoniagenesis: Purification and Characterization of Phosphate-Dependent Glutaminase from Rat Kidney," *Arch. Biochem. Biophys.* 174:82-89 (1976); Huang & Knox, "A Comparative Study of Glytaminase Isozymes in Rat Tissues," *Enzyme* 21:408-26 (1975), each of which is hereby incorporated by reference in its entirety). The most potent of these activators, inorganic phosphate, has been the most studied, having been shown to affect the oligomeric state of both the KGA and GAC isoforms. Additionally, recent high-resolution X-ray crystal structures have revealed potential binding sites for these anions (FIGS. 5A-B) and suggest that they exert their effects on enzymatic activity by changing the conformation of the activation loop (Thangavelu et al., "Structural Basis for the Allosteric Inhibitory Mechanism of Human Kidney-Type Glutaminase (KGA) and Its Regulation by Raf-Mek-Erk Signaling in Cancer Cell Metabolism," *Proc. Natl. Acad. Sci. U.S.A.* 109:7705-10 (2012), which is hereby incorporated by reference in its entirety).

Here the effects of these anionic activators on the tryptophan fluorescence of the $GAC_{F327W}$ mutant were examined. Anions that have been reported to activate glutaminase enzymes were first tested; namely, inorganic phosphate and sulfate. Unlike the changes observed for BPTES and CB-839, addition of these anions to $GAC_{F327W}$ resulted in marked enhancement of tryptophan fluorescence (FIG. 10A), thus providing evidence that they directly affect the conformation of the activation loop. Interestingly, it was found that the dose-dependent increases of fluorescence enhancement correlated well with the ability of a given anion to activate GAC. More specifically, sulfate ($SO_4^{2-}$) was ~50% as effective as phosphate ($HPO_4^{2-}$), which matched their abilities to enhance the tryptophan fluorescence of the F327W mutant (i.e., 15% versus 25%, respectively). Titrations with these anions yielded binding curves that were in good agreement with their ability to activate WT GAC (FIG. 10B, compare closed black and red circles with blue diamonds and triangles), suggesting that they act through a similar mechanism by affecting the conformation of the activation loop.

Figure 10C:
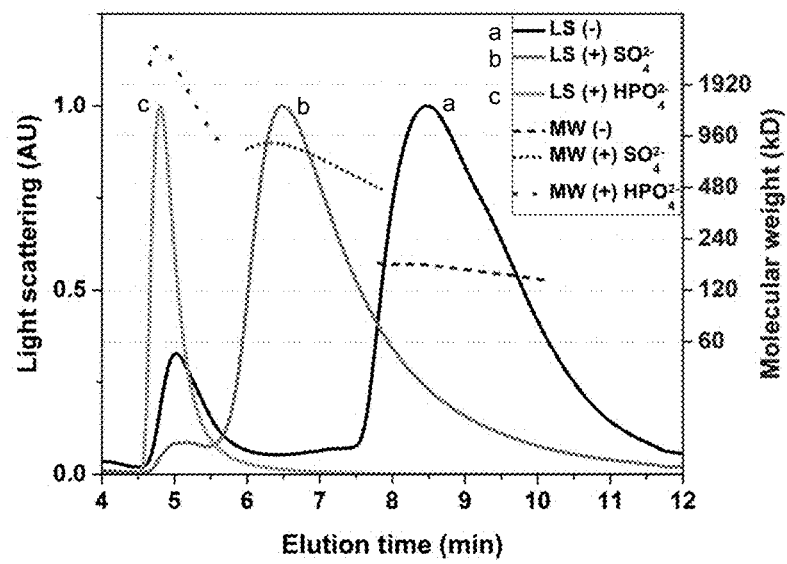

The effects of these ions on the molecular size distribution of GAC were next investigated as read out by SEC-MALS. Previous studies have described the formation of polytetrameric complexes that result from phosphate binding to high concentrations of enzyme (i.e., >1 mg/ml), where GAC tetramers bind end-on-end to form polymers. This led to the suggestion that these polytetrameric complexes might be necessary for stimulating enzyme activity (Ferreira et al., "Active Glutaminase C Self-Assembles into a Supratetrameric Oligomer That Can Be Disrupted by an Allosteric Inhibitor," *J. Biol. Chem.* 288:28009-20 (2013); Møller et al., "Small Angle X-Ray Scattering Studies of Mitochondrial Glutaminase C Reveal Extended Flexible Regions, and Link Oligomeric State with Enzyme Activity," *PLoS ONE* 8:e74783 (2013), which is hereby incorporated by reference in its entirety). Interestingly, it was found that sulfate, which has not been described previously to have an effect on the formation of GAC oligomers, stimulated the formation of a mixture of 16-mers and 8-mers but not the larger oligomers that are induced by phosphate (FIG. 10C, compare the dashed and dotted blue lines representing molecular weight for eluted species). These results, together with the $GAC_{F327W}$ fluorescence readout, suggest that the orientation of the activation loop results in an active conformation of the enzyme, which can then facilitate the formation of polytetrameric oligomers. They are also reflective of the differences in the ability of sulfate versus inorganic phosphate to stimulate GAC enzymatic activity and to enhance F327W fluorescence.

Example 8—Inorganic Phosphate Binds to the Tetrameric State of GAC

Figure 11:
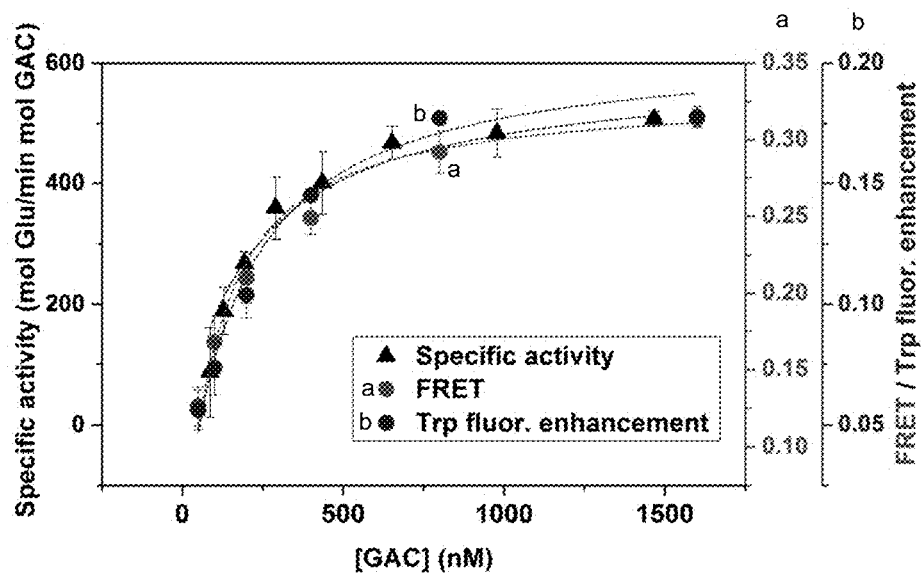
FIG. 11 is a graph of the enhancement of the F327W fluorescence upon addition of 50 mM $HPO_4^{2-}$ to increasing concentrations of $GAC_{F327W}$ (b, blue circles, right axis), plotted together with the previously reported FRET values (a, green circles, right axis) of 488- and QSY9-labeled WT GAC and the specific activity (black triangles, left axis) of WT GAC in the absence of phosphate (Stalnecker et al., "Mechanism by Which a Recently Discovered Allosteric Inhibitor Blocks Glutamine Metabolism in Transformed Cells," *Proc. Natl. Acad. Sci. U.S.A.* 112:394-99 (2015), which is hereby incorporated by reference in its entirety). Points represent the mean and error bars the standard deviation of three independent experiments.

The mechanism by which inorganic phosphate activates GAC activity is still unclear. In fact, it has been suggested that phosphate binds within the active site following catalysis, where it creates an electrostatic repulsion with the product to increase its off rate, thereby effectively increasing catalytic turnover (Cassago et al., "Mitochondrial Localization and Structure-Based Phosphate Activation Mechanism of Glutaminase C with Implications for Cancer Metabolism," *Proc. Natl. Acad. Sci. U.S.A.* 109:1092-97 (2012), which is hereby incorporated by reference in its entirety). The second proposed mechanism is that phosphate interacts with the activation loop at the dimer-dimer interface, much like allosteric inhibitors such as BPTES, and enables the loop to access an active conformation to stimulate catalysis (Thangavelu et al., "Structural Basis for the Allosteric Inhibitory Mechanism of Human Kidney-Type Glutaminase (KGA) and Its Regulation by Raf-Mek-Erk Signaling in Cancer Cell Metabolism," *Proc. Natl. Acad. Sci. U.S.A.* 109:7705-10 (2012), which is hereby incorporated by reference in its entirety). The enhancement of the tryptophan fluorescence of the F327W mutant observed here is consistent with the latter mechanism. Furthermore, it was found that the fluorescence enhancement induced by phosphate addition was dependent on GAC concentration and, therefore, the proportion of tetramers in solution. When this enhancement was plotted with respect to the concentration of GAC, it was in good agreement with FRET measurements that reflect the binding isotherm representing the transition of GAC dimers to tetramers and the concentration-dependent activation of the WT enzyme (FIG. 11, compare the black triangles on the left axis with the blue and green circles on the right axis). Taken together, these results suggest that phosphate binding promotes catalysis by interacting with the GAC tetramer, thereby inducing a conformational change within the activation loop, which, in turn, promotes enzymatic turnover.

Discussion of Examples 1-8

Prior studies of the structure-function relationships of glutaminases have revealed their essential role in glutamine metabolism within mammalian cells, where their activity is governed by their self-association to form tetramers (McGivan et al., "Rat Liver Glutaminase," *Eur. J. Biochem.* 148:323-27 (1985); Huang & Knox, "A Comparative Study of Glytaminase Isozymes in Rat Tissues," *Enzyme* 21:408-26 (1975); Darmaun et al., "Glutamine and Glutamate Kinetics in Humans," *Am. J. Physiol.* 251:E117-E126 (1986); Patel & McGivan, "Partial Purification and Properties of Rat Liver Glutaminase," *Biochem. J.* 220:583-90 (1984); Laake et al., "Postembedding Immunogold Labelling Reveals Subcellular Localization and Pathway-Specific Enrichment of Phosphate Activated Glutaminase in Rat Cerebellum," *Neuroscience* 88:1137-51 (1999), which are hereby incorporated by reference in their entirety). However, the mechanism by which tetramer formation stimulates enzymatic activity is not fully understood, presenting a significant challenge for rational drug design targeting this family of enzymes. The fact that a class of small molecule inhibitors, namely the bisthiadiazole derivatives, appeared to stabilize an inactive, tetrameric state of the KGA/GAC enzymes was an important discovery and further highlights the interest in understanding the mechanisms regulating glutaminase activity. Therefore, a spectroscopic readout for the flexible activation loop of GAC was developed, where BPTES binds, with the aim of obtaining mechanistic insights into how allosteric activators and inhibitors impact the loop and thereby exert their regulatory functions.

Recently, there has been a concerted effort to find small molecule inhibitors of the glutaminase enzymes using medicinal chemistry approaches (Gross et al., "Antitumor Activity of the Glutaminase Inhibitor CB-839 in Triple-Negative Breast Cancer," *Mol. Cancer Ther.* 13:890-901 (2014); Shukla et al., "Design, Synthesis, and Pharmacological Evaluation of Bis-2-(5-Phenylacetamido-1,2,4-Thiadiazol-2-yl)Ethyl Sulfide 3 (BPTES) Analogs as Glutaminase Inhibitors," *J. Med. Chem.* 55:10551-63 (2012); Zimmermann et al., "Allosteric Glutaminase Inhibitors Based on a 1,4-Di(5-Amino-1,3,4-Thiadiazol-2-yl)Butane Scaffold," *ACS Med. Chem. Lett.* 7:520-24 (2016); McDermott et al., "Design and Evaluation of Novel Glutaminase Inhibitors," *Bioorg. Med. Chem.* 24:1819-39 (2016), each of which is hereby incorporated by reference in its entirety). The differences between the allosteric activators inorganic phosphate and sulfate and the two most commonly used allosteric inhibitors, CB-839 and BPTES, were first compared in fluorescence assays that directly monitor GAC tetramer formation. It was found that both allosteric activators and inhibitors induced the formation of GAC tetramers; however, inhibitors were distinguished from activators by their ability to better stabilize the tetrameric state. CB-839 appears to act similarly to BPTES, so that the addition of either drug enhances tetramer formation. However, the CB-839-bound GAC tetramers labeled with FRET pairs were much less able to undergo exchange with excess unlabeled GAC subunits compared with BPTES-bound tetramers. Overall, these results agree with previous observations that CB-839 acts through a similar mechanism as BPTES, by binding at the dimer-dimer interface to promote the formation of an inactive tetramer, but with CB-839 having a significantly slower off rate compared with BPTES.

To address how allosteric activators and inhibitors both enhance GAC tetramer formation but exert opposing effects on enzyme activity, the available X-ray crystal structures of the KGA/GAC enzymes were examined and differences between the conformations of the activation loop were noticed. It was reasoned that, by comparing the activation loop in the BPTES-bound GAC structure versus that for free GAC, potential residues that, when substituted with the fluorescent amino acid tryptophan, may be able to be identified that would be sensitive to the dynamics of the loop. Indeed, it was found that the selective substitution of a single amino acid within the activation loop (specifically, changing phenylalanine 327 to a tryptophan residue) yields an enzyme that retains normal catalytic activity while providing a useful readout for the binding of allosteric inhibitors and activators. The native phenylalanine at position 327 has been shown previously to be an important residue for the activation of the KGA/GAC (GLS) isoforms (DeLaBarre et al., "Full-Length Human Glutaminase in Complex with an Allosteric Inhibitor," *Biochemistry* 50:10764-70 (2011), which is hereby incorporated by reference in its entirety). Additionally, Phe-327 is one of only two residues that differ between the liver-type (GLS2) and kidney-type (GLS) glutaminase enzymes in the activation loop, where the residue corresponding to phenylalanine at position 323 on the GLS enzymes is a tyrosine in GLS2, and phenylalanine 327 in GLS corresponds to a serine in GLS2 (Thangavelu et al., "Structural Basis for the Allosteric Inhibitory Mechanism of Human Kidney-Type Glutaminase (KGA) and Its Regulation by Raf-Mek-Erk Signaling in Cancer Cell Metabolism," *Proc. Natl. Acad. Sci. U.S.A.* 109:7705-10 (2012); DeLaBarre et al., "Full-Length Human Glutaminase in Complex with an Allosteric Inhibitor," *Biochemistry* 50:10764-70 (2011), each of which is hereby incorporated by reference in its entirety). GLS and GLS2 have been reported to have different catalytic properties (Curthoys et al., "Regulation of Renal Ammoniagenesis: Purification and Characterization of Phosphate-Dependent Glutaminase from Rat Kidney," *Arch. Biochem. Biophys.* 174:82-89 (1976), which is hereby incorporated by reference in its entirety), and it is of interest in this study that, of the various substitutions examined in the activation loop of GAC, only the F327W mutant provided a useful readout for both allosteric activators and inhibitors.

CB-839 has been suggested to be a more potent inhibitor of glutaminase activity compared with BPTES, with reported $IC_{50}$ values of 30 nM for CB-839 and between 80 nM and 3 M for BPTES (Thangavelu et al., "Structural Basis for the Allosteric Inhibitory Mechanism of Human Kidney-Type Glutaminase (KGA) and Its Regulation by Raf-Mek-Erk Signaling in Cancer Cell Metabolism," *Proc. Natl. Acad. Sci. U.S.A.* 109:7705-10 (2012); Robinson et al., "Novel Mechanism of Inhibition of Rat Kidney-Type Glutaminase by Bis-2-(5-Phenylacetamido-1,2,4-Thiadiazol-2-yl)Ethyl Sulfide (BPTES)," *Biochem. J.* 406:407-14 (2007); Hartwick & Curthoys, "BPTES Inhibition of hGA124-551, a Truncated Form of Human Kidney-Type Glutaminase," *J. Enzyme Inhib. Med. Chem.* 27:861-67 (2012); DeLaBarre et al., "Full-Length Human Glutaminase in Complex with an Allosteric Inhibitor," *Biochemistry* 50:10764-70 (2011); Gross et al., "Antitumor Activity of the Glutaminase Inhibitor CB-839 in Triple-Negative Breast Cancer," *Mol. Cancer Ther.* 13:890-901 (2014); Shukla et al., "Design, Synthesis, and Pharmacological Evaluation of Bis-2-(5-Phenylacetamido-1,2,4-Thiadiazol-2-yl)Ethyl Sulfide 3 (BPTES) Analogs as Glutaminase Inhibitors," *J. Med. Chem.* 55:10551-63 (2012); Thomas et al., "Small Molecule Glutaminase Inhibitors Block Glutamate Release from Stimulated Microglia," *Biochem. Biophys. Res. Commun.* 443:32-36 (2014), each of which is hereby incorporated by reference in its entirety). However, the direct binding of these inhibitors to KGA or GAC has never been compared, which has now been able to be done by taking advantage of the quenching of the intrinsic tryptophan fluorescence of the $GAC_{F327W}$ mutant induced by these compounds. Based on their titration profiles, it was determined that the two inhibitors have comparable dissociation constants (30 nM and 70 nM for CB-839 and BPTES, respectively (FIG. 8C)). The differences between the range of values reported for the $IC_{50}$ of BPTES from cell studies versus the $K_d$ value determined from direct binding assays may, at least in part, reflect a reduced efficiency in the ability of BPTES to reach its cellular target, GLS, because of the potential of this drug to accumulate in membranes. However, analysis of the real-time fluorescence data demonstrates that the rates of association and dissociation of CB-839 versus BPTES from the enzyme are different, with CB-839 showing slower binding kinetics (FIGS. 8A-B). This indicates a longer residence time for CB-839 that may contribute to some of its enhanced ability to inhibit phosphate-stimulated enzyme activity.

Figure 12:
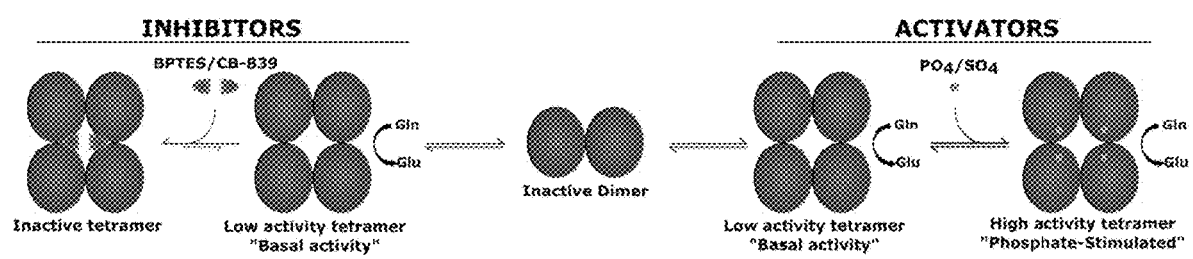
FIG. 12 is a schematic diagram showing the dimeric and tetrameric species of GAC as influenced by allosteric activators and BPTES class inhibitors. Inactive GAC dimers associate to form active GAC tetramers in the absence of allosteric activators or inhibitors (basal enzyme activity). Anionic activators, such as inorganic phosphate, bind to the GAC tetramer at the activation loop to induce an active conformation, resulting in activated tetramers with the potential of forming higher-order oligomers (not shown). BPTES class inhibitors bind to the activation loop in GAC tetramers, locking the activation loop in an inactive state, forming highly stable drug-bound tetramers. Gln=glutamine; Glu=glutamate.

The fluorescence assays described here for GAC tetramer formation, together with those for inhibitor binding and enzyme catalysis, allow for a more detailed analysis of how different classes of small molecule inhibitors interact with glutaminase to alter the activity of this important metabolic enzyme. FIG. 12 depicts a model in which BPTES-like inhibitors are incorporated into GAC tetramers in a manner that positions the activation loop in an orientation that prohibits catalysis and is reflected in the quenching of intrinsic $GAC_{F327W}$ fluorescence. Stabilization of the tetrameric form of GAC is similarly achieved by addition of anionic activators, but, conversely, the binding of phosphate or sulfate increases intrinsic $GAC_{F327W}$ fluorescence in proportion to the observed enzyme activity. The model proposes that the attendant increases in activity and fluorescence result from the stabilization of the activation loop in a conformation that reconfigures the glutamine binding site for catalysis. Although the model as drawn suggests that the binding of activators and inhibitors is mutually exclusive, the possibility that both reside simultaneously on GAC, competing for loop positioning and the corresponding fluorescence/activity changes on the same GAC monomer, cannot be ruled out.

The real-time fluorescence assays have provided an important and additional benefit; namely, the ability to directly monitor the interactions of allosteric anionic activators with GAC. Allosteric activators, such as inorganic phosphate, have been shown to promote changes in the oligomeric state of KGA/GAC enzymes that accompany their activation. However, although KGA/GAC oligomer formation has been consistently observed, the binding site for these anionic activators and the mechanistic outcome of oligomer formation are still not well understood. Recent studies have shown that mutations along the activation loop constitutively activate KGA/GAC so that anionic activators elicit no additional stimulatory effects (DeLaBarre et al., "Full-Length Human Glutaminase in Complex with an Allosteric Inhibitor," *Biochemistry* 50:10764-70 (2011); McDonald et al., "Effect of Lysine to Alanine Mutations on the Phosphate Activation and BPTES Inhibition of Glutaminase," *Neurochem. Int* 88:10-14 (2015); Ferreira et al., "Active Glutaminase C Self-Assembles into a Supratetrameric Oligomer That Can Be Disrupted by an Allosteric Inhibitor," *J. Biol. Chem.* 288:28009-20 (2013); Li et al., "Mechanistic Basis of Glutaminase Activation: A Key Enzyme That Promotes Glutamine Metabolism in Cancer Cells," *J. Biol. Chem.* 291:20900-10, each of which is hereby incorporated by reference in its entirety), suggesting that they exert their actions through the activation loop. The findings show that allosteric activators like inorganic phosphate induce an enhancement of the tryptophan fluorescence of the $GAC_{F327W}$ mutant, directly correlating with their ability to stimulate GAC activity. These results strongly support the idea that allosteric anionic activators bind at the dimer-dimer interface, changing the conformation and environment of the loop to varying degrees to promote activated GAC tetramers (FIG. 12). The findings further suggest that the activation loop influences the global structure of the enzyme, which can lead to the formation of polytetrameric GAC complexes (Ferreira et al., "Active Glutaminase C Self-Assembles into a Supratetrameric Oligomer That Can Be Disrupted by an Allosteric Inhibitor," *J. Biol. Chem.* 288:28009-20 (2013); Møller et al., "Small Angle X-Ray Scattering Studies of Mitochondrial Glutaminase C Reveal Extended Flexible Regions, and Link Oligomeric State with Enzyme Activity," *PLoS ONE* 8:e74783 (2013), each of which is hereby incorporated by reference in its entirety).

In conclusion, Examples 1-8 highlight the important roles the activation loop of GAC plays in regulating enzyme activity. The results presented here show that BPTES and CB-839 interact with the activation loop in a similar manner and demonstrate the utility of this novel F327W mutant and accompanying fluorescence assays for screening the effects bisthiadiazoles exert on the GLS enzymes. Similarly, it is shown that allosteric anionic activators directly impact the conformational dynamics of the activation loop, pointing to the potential usefulness of the F327W mutant in screening for additional small molecules capable of activating these enzymes. It is also expected that other GLS proteins having a corresponding mutation may also be used in these screening assays.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of screening for compounds that bind to the activation loop of kidney-type glutaminase ("GLS") protein, said method comprising:
    contacting GLS protein, wherein the GLS protein comprises an activation loop and comprises a phenylalanine to tryptophan substitution at the residue corresponding to position 322 of SEQ ID NO: 2, with a test compound, wherein the test compound is a compound that potentially binds to the activation loop, to permit binding between the activation loop and the test compound;
    detecting fluorescence of the substituted tryptophan in the presence of the test compound;
    comparing the detected fluorescence to fluorescence of a control; and
    identifying, based on said comparing, that the test compound is a compound that binds to the activation loop of GLS, wherein a change in fluorescence relative to the control indicates that the test compound binds to the activation loop.

2. The method according to claim 1, wherein said contacting is carried out in vitro.

3. The method according to claim 1, wherein said contacting comprises incubating the protein with the test compound for ten to thirty minutes.

4. The method according to claim 1, wherein the test compound is selected from the group consisting of bis-thiadiazoles, small inorganic anions, and negatively-charged metabolites.

5. The method according to claim 1, wherein said comparing comprises:
    (a) calculating the binding affinity between the test compound and the protein from the detected fluorescence and
    (b) comparing the calculated binding affinity to that of the control.

6. The method according to claim 1, wherein the fluorescence of the control is the fluorescence of the substituted tryptophan in the absence of the test compound.

7. The method according to claim 1, wherein the control is a second kidney-type glutaminase ("GLS") protein comprising a phenylalanine to tryptophan substitution at the residue corresponding to position 322 of SEQ ID NO: 2 and the fluorescence of the control is the fluorescence of the substituted tryptophan of the second GLS protein detected in the absence of the test compound.

8. The method according to claim 1 further comprising:
    contacting kidney-type glutaminase ("GLS") protein with glutamine in the presence of the test compound under conditions effective for the protein, if active, to convert glutamine to glutamate;
    measuring production of glutamate, if any, following said contacting with glutamine;
    comparing the measured glutamate production to glutamate production of a second control; and
    further identifying, based on said comparing glutamate production, that the test compound is a modulator of glutaminase activity of GLS, wherein a change in glutamate production relative to the second control indicates that the test compound modulates glutaminase activity of GLS.

9. The method according to claim 1 further comprising identifying a compound that also modulates glutaminase activity of kidney-type glutaminase ("GLS") protein, said further method comprising:
    selecting a test compound identified as being a compound that binds to the activation loop according to said identifying step;
    contacting GLS protein with glutamine in the presence of the selected test compound under conditions effective for the protein, if active, to convert glutamine to glutamate;
    measuring production of glutamate, if any, following said contacting with glutamine;
    comparing the measured glutamate production to glutamate production of a second control; and
    further identifying, based on said comparing glutamate production, that the selected test compound is also a modulator of glutaminase activity of GLS, wherein a change in glutamate production relative to the second control indicates that the selected test compound also modulates glutaminase activity of GLS.

* * * * *

SEQUENCE LISTING

<160> NUMBER OF SEQ ID NOS: 17

<210> SEQ ID NO 1
<211> LENGTH: 12
<212> TYPE: PRT
<213> ORGANISM: Human

<400> SEQUENCE: 1

Lys Glu Pro Ser Gly Leu Arg Phe Asn Lys Leu Phe
1               5                   10

<210> SEQ ID NO 2
<211> LENGTH: 598
<212> TYPE: PRT
<213> ORGANISM: Human

<400> SEQUENCE: 2

Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Arg Pro Ala Ala Gly Pro
        35                  40                  45

Ala Ala Ala Ala Arg Leu His Pro Trp Trp Gly Gly Gly Trp Pro
    50                  55                  60

Ala Glu Pro Leu Ala Arg Gly Leu Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

```
Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
    290                 295                 300

Val His Arg Tyr Val Gly Lys Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
        355                 360                 365

Glu Tyr Val Gly Phe Ser Asn Ala Thr Phe Gln Ser Glu Arg Glu Ser
    370                 375                 380

Gly Asp Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
        435                 440                 445

Ser Pro Glu Ala Val Arg Asn Thr Leu Ser Leu Met His Ser Cys Gly
    450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
    530                 535                 540

Glu Gly Gly Asp Gln Arg His Ser Phe Gly Pro Leu Asp Tyr Glu Ser
545                 550                 555                 560

Leu Gln Gln Glu Leu Ala Leu Lys Glu Thr Val Trp Lys Lys Val Ser
                565                 570                 575

Pro Glu Ser Asn Glu Asp Ile Ser Thr Thr Val Val Tyr Arg Met Glu
            580                 585                 590

Ser Leu Gly Glu Lys Ser
        595
```

```
<210> SEQ ID NO 3
<211> LENGTH: 603
<212> TYPE: PRT
<213> ORGANISM: Mouse

<400> SEQUENCE: 3
```

| | | | | | | | | | | | | | | | |
|---|---|---|---|---|---|---|---|---|---|---|---|---|---|---|---|
| Met | Met | Arg | Leu | Arg | Gly | Ser | Ala | Met | Leu | Arg | Glu | Leu | Leu | Leu | Arg |
| 1 | | | | 5 | | | | | 10 | | | | | 15 | |
| Pro | Pro | Ala | Ala | Val | Gly | Ala | Val | Leu | Arg | Arg | Ala | Gln | Pro | Leu | Gly |
| | | | 20 | | | | | 25 | | | | | 30 | | |
| Thr | Leu | Cys | Arg | Arg | Pro | Arg | Gly | Gly | Ser | Arg | Pro | Thr | Ala | Gly | Leu |
| | | | 35 | | | | | 40 | | | | | 45 | | |
| Val | Ala | Ala | Ala | Arg | Leu | His | Pro | Trp | Trp | Gly | Gly | Gly | Arg | Ala | |
| | 50 | | | | | 55 | | | | | 60 | | | | |
| Lys | Gly | Pro | Gly | Ala | Gly | Gly | Leu | Ser | Ser | Pro | Ser | Glu | Ile | Leu | |
| 65 | | | | | 70 | | | | | 75 | | | | | 80 |
| Gln | Glu | Leu | Gly | Lys | Gly | Gly | Thr | Pro | Pro | Gln | Gln | Gln | Gln | Gln | Gln |
| | | | | 85 | | | | | 90 | | | | | 95 | |
| Gln | Gln | Gln | Pro | Gly | Ala | Ser | Pro | Pro | Ala | Ala | Pro | Gly | Pro | Lys | Asp |
| | | | 100 | | | | | 105 | | | | | 110 | | |
| Ser | Pro | Gly | Glu | Thr | Asp | Ala | Phe | Gly | Asn | Ser | Glu | Gly | Lys | Glu | Met |
| | | 115 | | | | | 120 | | | | | 125 | | | |
| Val | Ala | Ala | Gly | Asp | Asn | Lys | Ile | Lys | Gln | Gly | Leu | Leu | Pro | Ser | Leu |
| | 130 | | | | | 135 | | | | | 140 | | | | |
| Glu | Asp | Leu | Leu | Phe | Tyr | Thr | Ile | Ala | Glu | Gly | Gln | Glu | Lys | Ile | Pro |
| 145 | | | | | 150 | | | | | 155 | | | | | 160 |
| Val | His | Lys | Phe | Ile | Thr | Ala | Leu | Lys | Ser | Thr | Gly | Leu | Arg | Thr | Ser |
| | | | | 165 | | | | | 170 | | | | | 175 | |
| Asp | Pro | Arg | Leu | Lys | Glu | Cys | Met | Asp | Met | Leu | Arg | Leu | Thr | Leu | Gln |
| | | | 180 | | | | | 185 | | | | | 190 | | |
| Thr | Thr | Ser | Asp | Gly | Val | Met | Leu | Asp | Lys | Asp | Leu | Phe | Lys | Lys | Cys |
| | | 195 | | | | | 200 | | | | | 205 | | | |
| Val | Gln | Ser | Asn | Ile | Val | Leu | Leu | Thr | Gln | Ala | Phe | Arg | Arg | Lys | Phe |
| | 210 | | | | | 215 | | | | | 220 | | | | |
| Val | Ile | Pro | Asp | Phe | Met | Ser | Phe | Thr | Ser | His | Ile | Asp | Glu | Leu | Tyr |
| 225 | | | | | 230 | | | | | 235 | | | | | 240 |
| Glu | Ser | Ala | Lys | Lys | Gln | Ser | Gly | Gly | Lys | Val | Ala | Asp | Tyr | Ile | Pro |
| | | | | 245 | | | | | 250 | | | | | 255 | |
| Gln | Leu | Ala | Lys | Phe | Ser | Pro | Asp | Leu | Trp | Gly | Val | Ser | Val | Cys | Thr |
| | | | 260 | | | | | 265 | | | | | 270 | | |
| Val | Asp | Gly | Gln | Arg | His | Ser | Ile | Gly | Asp | Thr | Lys | Val | Pro | Phe | Cys |
| | | 275 | | | | | 280 | | | | | 285 | | | |
| Leu | Gln | Ser | Cys | Val | Lys | Pro | Leu | Lys | Tyr | Ala | Ile | Ala | Val | Asn | Asp |
| | 290 | | | | | 295 | | | | | 300 | | | | |
| Leu | Gly | Thr | Glu | Tyr | Val | His | Arg | Tyr | Val | Gly | Lys | Glu | Pro | Ser | Gly |
| 305 | | | | | 310 | | | | | 315 | | | | | 320 |
| Leu | Arg | Phe | Asn | Lys | Leu | Phe | Leu | Asn | Glu | Asp | Lys | Pro | His | Asn | |
| | | | | 325 | | | | | 330 | | | | | 335 | |
| Pro | Met | Val | Asn | Ala | Gly | Ala | Ile | Val | Val | Thr | Ser | Leu | Ile | Lys | Gln |
| | | | 340 | | | | | 345 | | | | | 350 | | |
| Gly | Val | Asn | Asn | Ala | Glu | Lys | Phe | Asp | Tyr | Val | Met | Gln | Phe | Leu | Asn |
| | | 355 | | | | | 360 | | | | | 365 | | | |
| Lys | Met | Ala | Gly | Asn | Glu | Tyr | Val | Gly | Phe | Ser | Asn | Ala | Thr | Phe | Gln |
| | 370 | | | | | 375 | | | | | 380 | | | | |

```
Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
            405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
            435                 440                 445

Gly Glu Arg Val Leu Ser Pro Glu Ala Val Arg Asn Thr Leu Ser Leu
            450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Ile Leu Leu Val
                485                 490                 495

Val Pro Asn Val Met Gly Met Cys Trp Ser Pro Leu Asp Lys
                500                 505                 510

Met Gly Asn Ser Val Lys Gly Ile His Phe Cys His Asp Leu Val Ser
            515                 520                 525

Leu Cys Asn Phe His Asn Tyr Asp Asn Leu Arg His Phe Ala Lys Lys
530                 535                 540

Leu Asp Pro Arg Arg Glu Gly Asp Gln Arg His Ser Phe Gly Pro
545                 550                 555                 560

Leu Asp Tyr Glu Ser Leu Gln Gln Glu Leu Ala Leu Lys Asp Thr Val
                565                 570                 575

Trp Lys Lys Val Ser Pro Glu Ser Ser Asp Asp Thr Ser Thr Thr Val
                580                 585                 590

Val Tyr Arg Met Glu Ser Leu Gly Glu Arg Ser
                595                 600

<210> SEQ ID NO 4
<211> LENGTH: 603
<212> TYPE: PRT
<213> ORGANISM: Rat

<400> SEQUENCE: 4

Met Met Arg Leu Arg Gly Ser Ala Met Leu Arg Glu Leu Leu Leu Arg
1               5                   10                  15

Pro Pro Ala Ala Val Gly Gly Val Leu Arg Arg Ala Gln Pro Leu Gly
            20                  25                  30

Thr Leu Cys Arg Arg Pro Arg Gly Gly Ser Arg Pro Ala Ala Gly Leu
            35                  40                  45

Val Ala Ala Ala Arg Leu His Pro Trp Trp Gly Gly Gly Arg Ala
        50                  55                  60

Lys Gly Pro Gly Ser Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

Gln Gln Gln Pro Gly Ala Ser Pro Ala Ala Pro Gly Pro Lys Asp
            100                 105                 110

Ser Pro Gly Glu Thr Asp Ala Phe Gly Asn Ser Glu Gly Lys Glu Met
            115                 120                 125

Val Ala Ala Gly Asp Asn Lys Val Lys Gln Gly Leu Leu Pro Ser Leu
        130                 135                 140

Glu Asp Leu Leu Phe Tyr Thr Ile Ala Glu Gly Gln Glu Lys Ile Pro
145                 150                 155                 160
```

```
Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
    210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
            340                 345                 350

Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
    370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
        435                 440                 445

Gly Glu Arg Val Leu Ser Pro Glu Ala Val Arg Asn Thr Leu Ser Leu
    450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Gly Ile Leu Leu Val
                485                 490                 495

Val Pro Asn Val Met Gly Met Met Cys Trp Ser Pro Pro Leu Asp Lys
            500                 505                 510

Met Gly Asn Ser Val Lys Gly Ile His Phe Cys His Asp Leu Val Ser
        515                 520                 525

Leu Cys Asn Phe His Asn Tyr Asp Asn Leu Arg His Phe Ala Lys Lys
    530                 535                 540

Leu Asp Pro Arg Arg Glu Gly Gly Asp Gln Arg His Ser Phe Gly Pro
545                 550                 555                 560

Leu Asp Tyr Glu Ser Leu Gln Gln Glu Leu Ala Leu Lys Asp Thr Val
                565                 570                 575
```

```
Trp Lys Lys Val Ser Pro Glu Ser Ser Asp Thr Ser Thr Ile
            580             585             590

Val Tyr Arg Met Glu Ser Leu Gly Glu Arg Ser
            595             600

<210> SEQ ID NO 5
<211> LENGTH: 669
<212> TYPE: PRT
<213> ORGANISM: Human

<400> SEQUENCE: 5

Met Met Arg Leu Arg Gly Ser Gly Met Leu Arg Asp Leu Leu Leu Arg
1               5                  10                  15

Ser Pro Ala Gly Val Ser Ala Thr Leu Arg Arg Ala Gln Pro Leu Val
            20                  25                  30

Thr Leu Cys Arg Arg Pro Arg Gly Gly Arg Pro Ala Ala Gly Pro
        35                  40                  45

Ala Ala Ala Ala Arg Leu His Pro Trp Trp Gly Gly Gly Trp Pro
    50                  55                  60

Ala Glu Pro Leu Ala Arg Gly Leu Ser Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
    290                 295                 300

Val His Arg Tyr Val Gly Lys Glu Pro Ser Gly Leu Arg Phe Asn Lys
305                 310                 315                 320

Leu Phe Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350
```

Glu Lys Phe Asp Tyr Val Met Gln Phe Leu Asn Lys Met Ala Gly Asn
            355                 360                 365

Glu Tyr Val Gly Phe Ser Asn Ala Thr Phe Gln Ser Glu Arg Glu Ser
        370                 375                 380

Gly Asp Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
            435                 440                 445

Ser Pro Glu Ala Val Arg Asn Thr Leu Ser Leu Met His Ser Cys Gly
        450                 455                 460

Met Tyr Asp Phe Ser Gly Gln Phe Ala Phe His Val Gly Leu Pro Ala
465                 470                 475                 480

Lys Ser Gly Val Ala Gly Ile Leu Leu Val Pro Asn Val Met
                485                 490                 495

Gly Met Met Cys Trp Ser Pro Leu Asp Lys Met Gly Asn Ser Val
            500                 505                 510

Lys Gly Ile His Phe Cys His Asp Leu Val Ser Leu Cys Asn Phe His
            515                 520                 525

Asn Tyr Asp Asn Leu Arg His Phe Ala Lys Lys Leu Asp Pro Arg Arg
530                 535                 540

Glu Gly Gly Asp Gln Arg Val Lys Ser Val Ile Asn Leu Leu Phe Ala
545                 550                 555                 560

Ala Tyr Thr Gly Asp Val Ser Ala Leu Arg Arg Phe Ala Leu Ser Ala
                565                 570                 575

Met Asp Met Glu Gln Arg Asp Tyr Asp Ser Arg Thr Ala Leu His Val
            580                 585                 590

Ala Ala Ala Glu Gly His Val Glu Val Val Lys Phe Leu Leu Glu Ala
            595                 600                 605

Cys Lys Val Asn Pro Phe Pro Lys Asp Arg Trp Asn Asn Thr Pro Met
        610                 615                 620

Asp Glu Ala Leu His Phe Gly His His Asp Val Phe Lys Ile Leu Gln
625                 630                 635                 640

Glu Tyr Gln Val Gln Tyr Thr Pro Gln Gly Asp Ser Asp Asn Gly Lys
                645                 650                 655

Glu Asn Gln Thr Val His Lys Asn Leu Asp Gly Leu Leu
            660                 665

<210> SEQ ID NO 6
<211> LENGTH: 674
<212> TYPE: PRT
<213> ORGANISM: Mouse

<400> SEQUENCE: 6

Met Met Arg Leu Arg Gly Ser Ala Met Leu Arg Glu Leu Leu Leu Arg
1               5                   10                  15

Pro Pro Ala Ala Val Gly Ala Val Leu Arg Arg Ala Gln Pro Leu Gly
                20                  25                  30

Thr Leu Cys Arg Arg Pro Arg Gly Gly Ser Arg Pro Thr Ala Gly Leu
            35                  40                  45

Val Ala Ala Ala Arg Leu His Pro Trp Trp Gly Gly Gly Gly Arg Ala

```
            50                  55                  60
Lys Gly Pro Gly Ala Gly Leu Ser Ser Pro Ser Glu Ile Leu
 65                  70                  75                  80
Gln Glu Leu Gly Lys Gly Thr Pro Gln Gln Gln Gln Gln Gln
                 85                  90                  95
Gln Gln Gln Pro Gly Ala Ser Pro Ala Ala Pro Gly Pro Lys Asp
            100                 105                 110
Ser Pro Gly Glu Thr Asp Ala Phe Gly Asn Ser Glu Gly Lys Glu Met
            115                 120                 125
Val Ala Ala Gly Asp Asn Lys Ile Lys Gln Gly Leu Leu Pro Ser Leu
        130                 135                 140
Glu Asp Leu Leu Phe Tyr Thr Ile Ala Glu Gly Gln Glu Lys Ile Pro
145                 150                 155                 160
Val His Lys Phe Ile Thr Ala Leu Lys Ser Thr Gly Leu Arg Thr Ser
            165                 170                 175
Asp Pro Arg Leu Lys Glu Cys Met Asp Met Leu Arg Leu Thr Leu Gln
            180                 185                 190
Thr Thr Ser Asp Gly Val Met Leu Asp Lys Asp Leu Phe Lys Lys Cys
        195                 200                 205
Val Gln Ser Asn Ile Val Leu Leu Thr Gln Ala Phe Arg Arg Lys Phe
    210                 215                 220
Val Ile Pro Asp Phe Met Ser Phe Thr Ser His Ile Asp Glu Leu Tyr
225                 230                 235                 240
Glu Ser Ala Lys Lys Gln Ser Gly Gly Lys Val Ala Asp Tyr Ile Pro
            245                 250                 255
Gln Leu Ala Lys Phe Ser Pro Asp Leu Trp Gly Val Ser Val Cys Thr
            260                 265                 270
Val Asp Gly Gln Arg His Ser Ile Gly Asp Thr Lys Val Pro Phe Cys
        275                 280                 285
Leu Gln Ser Cys Val Lys Pro Leu Lys Tyr Ala Ile Ala Val Asn Asp
    290                 295                 300
Leu Gly Thr Glu Tyr Val His Arg Tyr Val Gly Lys Glu Pro Ser Gly
305                 310                 315                 320
Leu Arg Phe Asn Lys Leu Phe Leu Asn Glu Asp Lys Pro His Asn
            325                 330                 335
Pro Met Val Asn Ala Gly Ala Ile Val Val Thr Ser Leu Ile Lys Gln
            340                 345                 350
Gly Val Asn Asn Ala Glu Lys Phe Asp Tyr Val Met Gln Phe Leu Asn
        355                 360                 365
Lys Met Ala Gly Asn Glu Tyr Val Gly Phe Ser Asn Ala Thr Phe Gln
    370                 375                 380
Ser Glu Arg Glu Ser Gly Asp Arg Asn Phe Ala Ile Gly Tyr Tyr Leu
385                 390                 395                 400
Lys Glu Lys Lys Cys Phe Pro Glu Gly Thr Asp Met Val Gly Ile Leu
            405                 410                 415
Asp Phe Tyr Phe Gln Leu Cys Ser Ile Glu Val Thr Cys Glu Ser Ala
            420                 425                 430
Ser Val Met Ala Ala Thr Leu Ala Asn Gly Gly Phe Cys Pro Ile Thr
        435                 440                 445
Gly Glu Arg Val Leu Ser Pro Glu Ala Val Arg Asn Thr Leu Ser Leu
    450                 455                 460
Met His Ser Cys Gly Met Tyr Asp Phe Ser Gly Gln Phe Ala Phe His
465                 470                 475                 480
```

```
Val Gly Leu Pro Ala Lys Ser Gly Val Ala Gly Ile Leu Leu Val
            485                 490                 495

Val Pro Asn Val Met Gly Met Met Cys Trp Ser Pro Pro Leu Asp Lys
            500                 505                 510

Met Gly Asn Ser Val Lys Gly Ile His Phe Cys His Asp Leu Val Ser
            515                 520                 525

Leu Cys Asn Phe His Asn Tyr Asp Asn Leu Arg His Phe Ala Lys Lys
        530                 535                 540

Leu Asp Pro Arg Arg Glu Gly Asp Gln Arg Val Lys Ser Val Ile
545                 550                 555                 560

Asn Leu Leu Phe Ala Ala Tyr Thr Gly Asp Val Ser Ala Leu Arg Arg
                565                 570                 575

Phe Ala Leu Ser Ala Met Asp Met Glu Gln Arg Asp Tyr Asp Ser Arg
                580                 585                 590

Thr Ala Leu His Val Ala Ala Glu Gly His Val Glu Val Val Lys
                595                 600                 605

Phe Leu Leu Glu Ala Cys Lys Val Asn Pro Phe Pro Lys Asp Arg Trp
            610                 615                 620

Asn Asn Thr Pro Met Asp Glu Ala Leu His Phe Gly His His Asp Val
625                 630                 635                 640

Phe Lys Ile Leu Gln Glu Tyr Gln Val Gln Tyr Thr Pro Gln Gly Asp
                645                 650                 655

Ser Asp Asp Gly Lys Gly Asn Gln Thr Val His Lys Asn Leu Asp Gly
                660                 665                 670

Leu Leu

<210> SEQ ID NO 7
<211> LENGTH: 674
<212> TYPE: PRT
<213> ORGANISM: Rat

<400> SEQUENCE: 7

Met Met Arg Leu Arg Gly Ser Ala Met Leu Arg Glu Leu Leu Leu Arg
1               5                   10                  15

Pro Pro Ala Ala Val Gly Gly Val Leu Arg Arg Ala Gln Pro Leu Gly
                20                  25                  30

Thr Leu Cys Arg Pro Arg Gly Gly Ser Arg Pro Ala Ala Gly Leu
            35                  40                  45

Val Ala Ala Ala Arg Leu His Pro Trp Trp Gly Gly Gly Arg Ala
50                  55                  60

Lys Gly Pro Gly Ser Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

Gln Gln Gln Pro Gly Ala Ser Pro Pro Ala Ala Pro Gly Pro Lys Asp
            100                 105                 110

Ser Pro Gly Glu Thr Asp Ala Phe Gly Asn Ser Glu Gly Lys Glu Met
            115                 120                 125

Val Ala Ala Gly Asp Asn Lys Val Lys Gln Gly Leu Leu Pro Ser Leu
        130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175
```

-continued

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Lys Glu Pro Ser Gly
305                 310                 315                 320

Leu Arg Phe Asn Lys Leu Phe Leu Asn Glu Asp Asp Lys Pro His Asn
                325                 330                 335

Pro Met Val Asn Ala Gly Ala Ile Val Val Thr Ser Leu Ile Lys Gln
            340                 345                 350

Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
    370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
        435                 440                 445

Gly Glu Arg Val Leu Ser Pro Glu Ala Val Arg Asn Thr Leu Ser Leu
    450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Ile Leu Leu Val
                485                 490                 495

Val Pro Asn Val Met Gly Met Met Cys Trp Ser Pro Pro Leu Asp Lys
        500                 505                 510

Met Gly Asn Ser Val Lys Gly Ile His Phe Cys His Asp Leu Val Ser
    515                 520                 525

Leu Cys Asn Phe His Asn Tyr Asp Asn Leu Arg His Phe Ala Lys Lys
530                 535                 540

Leu Asp Pro Arg Arg Glu Gly Gly Asp Gln Arg Val Lys Ser Val Ile
545                 550                 555                 560

Asn Leu Leu Phe Ala Ala Tyr Thr Gly Asp Val Ser Ala Leu Arg Arg
                565                 570                 575

Phe Ala Leu Ser Ala Met Asp Met Glu Gln Arg Asp Tyr Asp Ser Arg
            580                 585                 590

```
Thr Ala Leu His Val Ala Ala Glu Gly His Val Glu Val Val Lys
            595                 600                 605

Phe Leu Leu Glu Ala Cys Lys Val Asn Pro Phe Pro Lys Asp Arg Trp
        610                 615                 620

Asn Asn Thr Pro Met Asp Glu Ala Leu His Phe Gly His His Asp Val
625                 630                 635                 640

Phe Lys Ile Leu Gln Glu Tyr Gln Val Gln Tyr Thr Pro Gln Gly Asp
                645                 650                 655

Ser Asp Asp Gly Lys Glu Asn Gln Thr Val His Lys Asn Leu Asp Gly
            660                 665                 670

Leu Leu

<210> SEQ ID NO 8
<211> LENGTH: 598
<212> TYPE: PRT
<213> ORGANISM: Artificial
<220> FEATURE:
<223> OTHER INFORMATION: Human GAC with F322W Substitution

<400> SEQUENCE: 8

Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Gly Arg Pro Ala Ala Gly Pro
        35                  40                  45

Ala Ala Ala Ala Arg Leu His Pro Trp Trp Gly Gly Gly Trp Pro
50                  55                  60

Ala Glu Pro Leu Ala Arg Gly Leu Ser Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
```

```
                275                 280                 285
Lys Pro Leu Lys Tyr Ala Ile Ala Val Asn Asp Leu Gly Thr Glu Tyr
        290                 295                 300

Val His Arg Tyr Val Gly Lys Glu Pro Ser Gly Leu Arg Phe Asn Lys
305                 310                 315                 320

Leu Trp Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
        355                 360                 365

Glu Tyr Val Gly Phe Ser Asn Ala Thr Phe Gln Ser Glu Arg Glu Ser
370                 375                 380

Gly Asp Arg Asn Phe Ala Ile Gly Tyr Tyr Leu Lys Glu Lys Lys Cys
385                 390                 395                 400

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
        435                 440                 445

Ser Pro Glu Ala Val Arg Asn Thr Leu Ser Leu Met His Ser Cys Gly
450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
530                 535                 540

Glu Gly Gly Asp Gln Arg His Ser Phe Gly Pro Leu Asp Tyr Glu Ser
545                 550                 555                 560

Leu Gln Gln Glu Leu Ala Leu Lys Glu Thr Val Trp Lys Lys Val Ser
                565                 570                 575

Pro Glu Ser Asn Glu Asp Ile Ser Thr Thr Val Val Tyr Arg Met Glu
            580                 585                 590

Ser Leu Gly Glu Lys Ser
        595

<210> SEQ ID NO 9
<211> LENGTH: 603
<212> TYPE: PRT
<213> ORGANISM: Artificial
<220> FEATURE:
<223> OTHER INFORMATION: Mouse GAC with F327W substitution

<400> SEQUENCE: 9

Met Met Arg Leu Arg Gly Ser Ala Met Leu Arg Glu Leu Leu Leu Arg
1               5                   10                  15

Pro Pro Ala Ala Val Gly Ala Val Leu Arg Arg Ala Gln Pro Leu Gly
            20                  25                  30

Thr Leu Cys Arg Arg Pro Arg Gly Gly Ser Arg Pro Thr Ala Gly Leu
```

```
            35                  40                  45
Val Ala Ala Arg Leu His Pro Trp Trp Gly Gly Gly Arg Ala
 50                  55                  60
Lys Gly Pro Gly Ala Gly Gly Leu Ser Ser Pro Ser Glu Ile Leu
 65                  70                  75                  80
Gln Glu Leu Gly Lys Gly Gly Thr Pro Pro Gln Gln Gln Gln Gln
                     85                  90                  95
Gln Gln Gln Pro Gly Ala Ser Pro Pro Ala Ala Pro Gly Pro Lys Asp
            100                 105                 110
Ser Pro Gly Glu Thr Asp Ala Phe Gly Asn Ser Glu Gly Lys Glu Met
            115                 120                 125
Val Ala Ala Gly Asp Asn Lys Ile Lys Gln Gly Leu Leu Pro Ser Leu
            130                 135                 140
Glu Asp Leu Leu Phe Tyr Thr Ile Ala Glu Gly Gln Glu Lys Ile Pro
145                 150                 155                 160
Val His Lys Phe Ile Thr Ala Leu Lys Ser Thr Gly Leu Arg Thr Ser
                    165                 170                 175
Asp Pro Arg Leu Lys Glu Cys Met Asp Met Leu Arg Leu Thr Leu Gln
                    180                 185                 190
Thr Thr Ser Asp Gly Val Met Leu Asp Lys Asp Leu Phe Lys Lys Cys
            195                 200                 205
Val Gln Ser Asn Ile Val Leu Leu Thr Gln Ala Phe Arg Arg Lys Phe
            210                 215                 220
Val Ile Pro Asp Phe Met Ser Phe Thr Ser His Ile Asp Glu Leu Tyr
225                 230                 235                 240
Glu Ser Ala Lys Lys Gln Ser Gly Gly Lys Val Ala Asp Tyr Ile Pro
                    245                 250                 255
Gln Leu Ala Lys Phe Ser Pro Asp Leu Trp Gly Val Ser Val Cys Thr
                    260                 265                 270
Val Asp Gly Gln Arg His Ser Ile Gly Asp Thr Lys Val Pro Phe Cys
            275                 280                 285
Leu Gln Ser Cys Val Lys Pro Leu Lys Tyr Ala Ile Ala Val Asn Asp
            290                 295                 300
Leu Gly Thr Glu Tyr Val His Arg Tyr Val Gly Lys Glu Pro Ser Gly
305                 310                 315                 320
Leu Arg Phe Asn Lys Leu Trp Leu Asn Glu Asp Asp Lys Pro His Asn
                    325                 330                 335
Pro Met Val Asn Ala Gly Ala Ile Val Val Thr Ser Leu Ile Lys Gln
            340                 345                 350
Gly Val Asn Asn Ala Glu Lys Phe Asp Tyr Val Met Gln Phe Leu Asn
            355                 360                 365
Lys Met Ala Gly Asn Glu Tyr Val Gly Phe Ser Asn Ala Thr Phe Gln
            370                 375                 380
Ser Glu Arg Glu Ser Gly Asp Arg Asn Phe Ala Ile Gly Tyr Tyr Leu
385                 390                 395                 400
Lys Glu Lys Lys Cys Phe Pro Glu Gly Thr Asp Met Val Gly Ile Leu
                    405                 410                 415
Asp Phe Tyr Phe Gln Leu Cys Ser Ile Glu Val Thr Cys Glu Ser Ala
                    420                 425                 430
Ser Val Met Ala Ala Thr Leu Ala Asn Gly Gly Phe Cys Pro Ile Thr
            435                 440                 445
Gly Glu Arg Val Leu Ser Pro Glu Ala Val Arg Asn Thr Leu Ser Leu
            450                 455                 460
```

```
Met His Ser Cys Gly Met Tyr Asp Phe Ser Gly Gln Phe Ala Phe His
465                 470                 475                 480

Val Gly Leu Pro Ala Lys Ser Gly Val Ala Gly Ile Leu Leu Val
            485                 490                 495

Val Pro Asn Val Met Gly Met Met Cys Trp Ser Pro Leu Asp Lys
        500                 505                 510

Met Gly Asn Ser Val Lys Gly Ile His Phe Cys His Asp Leu Val Ser
                515                 520                 525

Leu Cys Asn Phe His Asn Tyr Asp Asn Leu Arg His Phe Ala Lys Lys
530                 535                 540

Leu Asp Pro Arg Arg Glu Gly Asp Gln Arg His Ser Phe Gly Pro
545                 550                 555                 560

Leu Asp Tyr Glu Ser Leu Gln Gln Glu Leu Ala Leu Lys Asp Thr Val
                565                 570                 575

Trp Lys Lys Val Ser Pro Glu Ser Ser Asp Asp Thr Ser Thr Thr Val
                580                 585                 590

Val Tyr Arg Met Glu Ser Leu Gly Glu Arg Ser
        595                 600

<210> SEQ ID NO 10
<211> LENGTH: 603
<212> TYPE: PRT
<213> ORGANISM: Artificial
<220> FEATURE:
<223> OTHER INFORMATION: Rat GAC with F327W substitution

<400> SEQUENCE: 10

Met Met Arg Leu Arg Gly Ser Ala Met Leu Arg Glu Leu Leu Leu Arg
1               5                   10                  15

Pro Pro Ala Ala Val Gly Gly Val Leu Arg Arg Ala Gln Pro Leu Gly
            20                  25                  30

Thr Leu Cys Arg Arg Pro Arg Gly Gly Ser Arg Pro Ala Ala Gly Leu
        35                  40                  45

Val Ala Ala Ala Arg Leu His Pro Trp Trp Gly Gly Gly Gly Arg Ala
50                  55                  60

Lys Gly Pro Gly Ser Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

Gln Gln Gln Pro Gly Ala Ser Pro Pro Ala Ala Pro Gly Pro Lys Asp
            100                 105                 110

Ser Pro Gly Glu Thr Asp Ala Phe Gly Asn Ser Glu Gly Lys Glu Met
        115                 120                 125

Val Ala Ala Gly Asp Asn Lys Val Lys Gln Gly Leu Leu Pro Ser Leu
130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
210                 215                 220
```

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
            245                 250                 255

Gln Leu Ala Lys Phe Ser Pro Asp Leu Trp Gly Val Ser Val Cys Thr
        260                 265                 270

Val Asp Gly Gln Arg His Ser Ile Gly Asp Thr Lys Val Pro Phe Cys
    275                 280                 285

Leu Gln Ser Cys Val Lys Pro Leu Lys Tyr Ala Ile Ala Val Asn Asp
290                 295                 300

Leu Gly Thr Glu Tyr Val His Arg Tyr Val Gly Lys Glu Pro Ser Gly
305                 310                 315                 320

Leu Arg Phe Asn Lys Leu Trp Leu Asn Glu Asp Asp Lys Pro His Asn
            325                 330                 335

Pro Met Val Asn Ala Gly Ala Ile Val Val Thr Ser Leu Ile Lys Gln
        340                 345                 350

Gly Val Asn Asn Ala Glu Lys Phe Asp Tyr Val Met Gln Phe Leu Asn
    355                 360                 365

Lys Met Ala Gly Asn Glu Tyr Val Gly Phe Ser Asn Ala Thr Phe Gln
370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
            405                 410                 415

Asp Phe Tyr Phe Gln Leu Cys Ser Ile Glu Val Thr Cys Glu Ser Ala
        420                 425                 430

Ser Val Met Ala Ala Thr Leu Ala Asn Gly Gly Phe Cys Pro Ile Thr
    435                 440                 445

Gly Glu Arg Val Leu Ser Pro Glu Ala Val Arg Asn Thr Leu Ser Leu
450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Gly Ile Leu Leu Val
            485                 490                 495

Val Pro Asn Val Met Gly Met Met Cys Trp Ser Pro Pro Leu Asp Lys
        500                 505                 510

Met Gly Asn Ser Val Lys Gly Ile His Phe Cys His Asp Leu Val Ser
    515                 520                 525

Leu Cys Asn Phe His Asn Tyr Asp Asn Leu Arg His Phe Ala Lys Lys
530                 535                 540

Leu Asp Pro Arg Arg Glu Gly Gly Asp Gln Arg His Ser Phe Gly Pro
545                 550                 555                 560

Leu Asp Tyr Glu Ser Leu Gln Gln Glu Leu Ala Leu Lys Asp Thr Val
            565                 570                 575

Trp Lys Lys Val Ser Pro Glu Ser Ser Asp Asp Thr Ser Thr Thr Ile
        580                 585                 590

Val Tyr Arg Met Glu Ser Leu Gly Glu Arg Ser
    595                 600

<210> SEQ ID NO 11
<211> LENGTH: 669
<212> TYPE: PRT
<213> ORGANISM: Artificial
<220> FEATURE:

<223> OTHER INFORMATION: Human KGA with F322W substitution

<400> SEQUENCE: 11

```
Met Met Arg Leu Arg Gly Ser Gly Met Leu Arg Asp Leu Leu Leu Arg
1               5                   10                  15

Ser Pro Ala Gly Val Ser Ala Thr Leu Arg Arg Ala Gln Pro Leu Val
            20                  25                  30

Thr Leu Cys Arg Arg Pro Arg Gly Gly Gly Arg Pro Ala Ala Gly Pro
        35                  40                  45

Ala Ala Ala Ala Arg Leu His Pro Trp Trp Gly Gly Gly Trp Pro
50                  55                  60

Ala Glu Pro Leu Ala Arg Gly Leu Ser Ser Pro Ser Glu Ile Leu
65                  70                  75                  80

Gln Glu Leu Gly Lys Gly Ser Thr His Pro Gln Pro Gly Val Ser Pro
                85                  90                  95

Pro Ala Ala Pro Ala Ala Pro Gly Pro Lys Asp Gly Pro Gly Glu Thr
            100                 105                 110

Asp Ala Phe Gly Asn Ser Glu Gly Lys Glu Leu Val Ala Ser Gly Glu
        115                 120                 125

Asn Lys Ile Lys Gln Gly Leu Leu Pro Ser Leu Glu Asp Leu Leu Phe
    130                 135                 140

Tyr Thr Ile Ala Glu Gly Gln Glu Lys Ile Pro Val His Lys Phe Ile
145                 150                 155                 160

Thr Ala Leu Lys Ser Thr Gly Leu Arg Thr Ser Asp Pro Arg Leu Lys
                165                 170                 175

Glu Cys Met Asp Met Leu Arg Leu Thr Leu Gln Thr Thr Ser Asp Gly
            180                 185                 190

Val Met Leu Asp Lys Asp Leu Phe Lys Lys Cys Val Gln Ser Asn Ile
        195                 200                 205

Val Leu Leu Thr Gln Ala Phe Arg Arg Lys Phe Val Ile Pro Asp Phe
    210                 215                 220

Met Ser Phe Thr Ser His Ile Asp Glu Leu Tyr Glu Ser Ala Lys Lys
225                 230                 235                 240

Gln Ser Gly Gly Lys Val Ala Asp Tyr Ile Pro Gln Leu Ala Lys Phe
                245                 250                 255

Ser Pro Asp Leu Trp Gly Val Ser Val Cys Thr Val Asp Gly Gln Arg
            260                 265                 270

His Ser Thr Gly Asp Thr Lys Val Pro Phe Cys Leu Gln Ser Cys Val
        275                 280                 285

Lys Pro Leu Lys Tyr Ala Ile Ala Val Asn Asp Leu Gly Thr Glu Tyr
    290                 295                 300

Val His Arg Tyr Val Gly Lys Glu Pro Ser Gly Leu Arg Phe Asn Lys
305                 310                 315                 320

Leu Trp Leu Asn Glu Asp Asp Lys Pro His Asn Pro Met Val Asn Ala
                325                 330                 335

Gly Ala Ile Val Val Thr Ser Leu Ile Lys Gln Gly Val Asn Asn Ala
            340                 345                 350

Glu Lys Phe Asp Tyr Val Met Gln Phe Leu Asn Lys Met Ala Gly Asn
        355                 360                 365

Glu Tyr Val Gly Phe Ser Asn Ala Thr Phe Gln Ser Glu Arg Glu Ser
    370                 375                 380

Gly Asp Arg Asn Phe Ala Ile Gly Tyr Tyr Leu Lys Glu Lys Lys Cys
385                 390                 395                 400
```

Phe Pro Glu Gly Thr Asp Met Val Gly Ile Leu Asp Phe Tyr Phe Gln
                405                 410                 415

Leu Cys Ser Ile Glu Val Thr Cys Glu Ser Ala Ser Val Met Ala Ala
            420                 425                 430

Thr Leu Ala Asn Gly Gly Phe Cys Pro Ile Thr Gly Glu Arg Val Leu
        435                 440                 445

Ser Pro Glu Ala Val Arg Asn Thr Leu Ser Leu Met His Ser Cys Gly
    450                 455                 460

Met Tyr Asp Phe Ser Gly Gln Phe Ala Phe His Val Gly Leu Pro Ala
465                 470                 475                 480

Lys Ser Gly Val Ala Gly Gly Ile Leu Leu Val Val Pro Asn Val Met
                485                 490                 495

Gly Met Met Cys Trp Ser Pro Pro Leu Asp Lys Met Gly Asn Ser Val
            500                 505                 510

Lys Gly Ile His Phe Cys His Asp Leu Val Ser Leu Cys Asn Phe His
        515                 520                 525

Asn Tyr Asp Asn Leu Arg His Phe Ala Lys Lys Leu Asp Pro Arg Arg
    530                 535                 540

Glu Gly Gly Asp Gln Arg Val Lys Ser Val Ile Asn Leu Leu Phe Ala
545                 550                 555                 560

Ala Tyr Thr Gly Asp Val Ser Ala Leu Arg Arg Phe Ala Leu Ser Ala
                565                 570                 575

Met Asp Met Glu Gln Arg Asp Tyr Asp Ser Arg Thr Ala Leu His Val
            580                 585                 590

Ala Ala Ala Glu Gly His Val Glu Val Val Lys Phe Leu Leu Glu Ala
        595                 600                 605

Cys Lys Val Asn Pro Phe Pro Lys Asp Arg Trp Asn Asn Thr Pro Met
    610                 615                 620

Asp Glu Ala Leu His Phe Gly His His Asp Val Phe Lys Ile Leu Gln
625                 630                 635                 640

Glu Tyr Gln Val Gln Tyr Thr Pro Gln Gly Asp Ser Asp Asn Gly Lys
                645                 650                 655

Glu Asn Gln Thr Val His Lys Asn Leu Asp Gly Leu Leu
            660                 665

<210> SEQ ID NO 12
<211> LENGTH: 674
<212> TYPE: PRT
<213> ORGANISM: Artificial
<220> FEATURE:
<223> OTHER INFORMATION: Mouse KGA with F327W substitution

<400> SEQUENCE: 12

Met Met Arg Leu Arg Gly Ser Ala Met Leu Arg Glu Leu Leu Leu Arg
1               5                   10                  15

Pro Pro Ala Ala Val Gly Ala Val Leu Arg Arg Ala Gln Pro Leu Gly
                20                  25                  30

Thr Leu Cys Arg Arg Pro Arg Gly Gly Ser Arg Pro Thr Ala Gly Leu
            35                  40                  45

Val Ala Ala Ala Arg Leu His Pro Trp Trp Gly Gly Gly Arg Ala
        50                  55                  60

Lys Gly Pro Gly Ala Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

```
Gln Gln Gln Pro Gly Ala Ser Pro Ala Ala Pro Gly Pro Lys Asp
            100                 105                 110

Ser Pro Gly Glu Thr Asp Ala Phe Gly Asn Ser Glu Gly Lys Glu Met
        115                 120                 125

Val Ala Ala Gly Asp Asn Lys Ile Lys Gln Gly Leu Leu Pro Ser Leu
    130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205

Val Gln Ser Asn Ile Val Leu Leu Thr Gln Ala Phe Arg Arg Lys Phe
    210                 215                 220

Val Ile Pro Asp Phe Met Ser Phe Thr Ser His Ile Asp Glu Leu Tyr
225                 230                 235                 240

Glu Ser Ala Lys Lys Gln Ser Gly Gly Lys Val Ala Asp Tyr Ile Pro
                245                 250                 255

Gln Leu Ala Lys Phe Ser Pro Asp Leu Trp Gly Val Ser Val Cys Thr
            260                 265                 270

Val Asp Gly Gln Arg His Ser Ile Gly Asp Thr Lys Val Pro Phe Cys
        275                 280                 285

Leu Gln Ser Cys Val Lys Pro Leu Lys Tyr Ala Ile Ala Val Asn Asp
    290                 295                 300

Leu Gly Thr Glu Tyr Val His Arg Tyr Val Gly Lys Glu Pro Ser Gly
305                 310                 315                 320

Leu Arg Phe Asn Lys Leu Trp Leu Asn Glu Asp Lys Pro His Asn
                325                 330                 335

Pro Met Val Asn Ala Gly Ala Ile Val Val Thr Ser Leu Ile Lys Gln
            340                 345                 350

Gly Val Asn Asn Ala Glu Lys Phe Asp Tyr Val Met Gln Phe Leu Asn
        355                 360                 365

Lys Met Ala Gly Asn Glu Tyr Val Gly Phe Ser Asn Ala Thr Phe Gln
    370                 375                 380

Ser Glu Arg Glu Ser Gly Asp Arg Asn Phe Ala Ile Gly Tyr Tyr Leu
385                 390                 395                 400

Lys Glu Lys Lys Cys Phe Pro Glu Gly Thr Asp Met Val Gly Ile Leu
                405                 410                 415

Asp Phe Tyr Phe Gln Leu Cys Ser Ile Glu Val Thr Cys Glu Ser Ala
            420                 425                 430

Ser Val Met Ala Ala Thr Leu Ala Asn Gly Gly Phe Cys Pro Ile Thr
        435                 440                 445

Gly Glu Arg Val Leu Ser Pro Glu Ala Val Arg Asn Thr Leu Ser Leu
    450                 455                 460

Met His Ser Cys Gly Met Tyr Asp Phe Ser Gly Gln Phe Ala Phe His
465                 470                 475                 480

Val Gly Leu Pro Ala Lys Ser Gly Val Ala Gly Ile Leu Leu Val
                485                 490                 495

Val Pro Asn Val Met Gly Met Met Cys Trp Ser Pro Pro Leu Asp Lys
            500                 505                 510

Met Gly Asn Ser Val Lys Gly Ile His Phe Cys His Asp Leu Val Ser
```

```
                515                 520                 525
Leu Cys Asn Phe His Asn Tyr Asp Asn Leu Arg His Phe Ala Lys Lys
    530                 535                 540

Leu Asp Pro Arg Arg Glu Gly Gly Asp Gln Arg Val Lys Ser Val Ile
545                 550                 555                 560

Asn Leu Leu Phe Ala Ala Tyr Thr Gly Asp Val Ser Ala Leu Arg Arg
                565                 570                 575

Phe Ala Leu Ser Ala Met Asp Met Glu Gln Arg Asp Tyr Asp Ser Arg
            580                 585                 590

Thr Ala Leu His Val Ala Ala Glu Gly His Val Glu Val Val Lys
        595                 600                 605

Phe Leu Leu Glu Ala Cys Lys Val Asn Pro Phe Pro Lys Asp Arg Trp
610                 615                 620

Asn Asn Thr Pro Met Asp Glu Ala Leu His Phe Gly His His Asp Val
625                 630                 635                 640

Phe Lys Ile Leu Gln Glu Tyr Gln Val Gln Tyr Thr Pro Gln Gly Asp
                645                 650                 655

Ser Asp Asp Gly Lys Gly Asn Gln Thr Val His Lys Asn Leu Asp Gly
            660                 665                 670

Leu Leu

<210> SEQ ID NO 13
<211> LENGTH: 674
<212> TYPE: PRT
<213> ORGANISM: Artificial
<220> FEATURE:
<223> OTHER INFORMATION: Rat KGA with F327W substitution

<400> SEQUENCE: 13

Met Met Arg Leu Arg Gly Ser Ala Met Leu Arg Glu Leu Leu Leu Arg
1               5                   10                  15

Pro Pro Ala Ala Val Gly Gly Val Leu Arg Arg Ala Gln Pro Leu Gly
                20                  25                  30

Thr Leu Cys Arg Arg Pro Arg Gly Gly Ser Arg Pro Ala Ala Gly Leu
            35                  40                  45

Val Ala Ala Arg Leu His Pro Trp Trp Gly Gly Gly Arg Ala
50                  55                  60

Lys Gly Pro Gly Ser Gly Gly Leu Ser Ser Ser Pro Ser Glu Ile Leu
65                  70                  75                  80

Gln Glu Leu Gly Lys Gly Gly Thr Pro Pro Gln Gln Gln Gln Gln Gln
                85                  90                  95

Gln Gln Gln Pro Gly Ala Ser Pro Pro Ala Ala Pro Gly Pro Lys Asp
            100                 105                 110

Ser Pro Gly Glu Thr Asp Ala Phe Gly Asn Ser Glu Gly Lys Glu Met
        115                 120                 125

Val Ala Ala Gly Asp Asn Lys Val Lys Gln Gly Leu Leu Pro Ser Leu
    130                 135                 140

Glu Asp Leu Leu Phe Tyr Thr Ile Ala Glu Gly Gln Glu Lys Ile Pro
145                 150                 155                 160

Val His Lys Phe Ile Thr Ala Leu Lys Ser Thr Gly Leu Arg Thr Ser
                165                 170                 175

Asp Pro Arg Leu Lys Glu Cys Met Asp Met Leu Arg Leu Thr Leu Gln
            180                 185                 190

Thr Thr Ser Asp Gly Val Met Leu Asp Lys Asp Leu Phe Lys Lys Cys
        195                 200                 205
```

```
Val Gln Ser Asn Ile Val Leu Leu Thr Gln Ala Phe Arg Arg Lys Phe
    210                 215                 220
Val Ile Pro Asp Phe Met Ser Phe Thr Ser His Ile Asp Glu Leu Tyr
225                 230                 235                 240
Glu Ser Ala Lys Lys Gln Ser Gly Gly Lys Val Ala Asp Tyr Ile Pro
                245                 250                 255
Gln Leu Ala Lys Phe Ser Pro Asp Leu Trp Gly Val Ser Val Cys Thr
                260                 265                 270
Val Asp Gly Gln Arg His Ser Ile Gly Asp Thr Lys Val Pro Phe Cys
            275                 280                 285
Leu Gln Ser Cys Val Lys Pro Leu Lys Tyr Ala Ile Ala Val Asn Asp
    290                 295                 300
Leu Gly Thr Glu Tyr Val His Arg Tyr Val Gly Lys Glu Pro Ser Gly
305                 310                 315                 320
Leu Arg Phe Asn Lys Leu Trp Leu Asn Glu Asp Asp Lys Pro His Asn
                325                 330                 335
Pro Met Val Asn Ala Gly Ala Ile Val Val Thr Ser Leu Ile Lys Gln
                340                 345                 350
Gly Val Asn Asn Ala Glu Lys Phe Asp Tyr Val Met Gln Phe Leu Asn
            355                 360                 365
Lys Met Ala Gly Asn Glu Tyr Val Gly Phe Ser Asn Ala Thr Phe Gln
    370                 375                 380
Ser Glu Arg Glu Ser Gly Asp Arg Asn Phe Ala Ile Gly Tyr Tyr Leu
385                 390                 395                 400
Lys Glu Lys Lys Cys Phe Pro Glu Gly Thr Asp Met Val Gly Ile Leu
                405                 410                 415
Asp Phe Tyr Phe Gln Leu Cys Ser Ile Glu Val Thr Cys Glu Ser Ala
                420                 425                 430
Ser Val Met Ala Ala Thr Leu Ala Asn Gly Gly Phe Cys Pro Ile Thr
            435                 440                 445
Gly Glu Arg Val Leu Ser Pro Glu Ala Val Arg Asn Thr Leu Ser Leu
    450                 455                 460
Met His Ser Cys Gly Met Tyr Asp Phe Ser Gly Gln Phe Ala Phe His
465                 470                 475                 480
Val Gly Leu Pro Ala Lys Ser Gly Val Ala Gly Gly Ile Leu Leu Val
                485                 490                 495
Val Pro Asn Val Met Gly Met Met Cys Trp Ser Pro Pro Leu Asp Lys
                500                 505                 510
Met Gly Asn Ser Val Lys Gly Ile His Phe Cys His Asp Leu Val Ser
            515                 520                 525
Leu Cys Asn Phe His Asn Tyr Asp Asn Leu Arg His Phe Ala Lys Lys
    530                 535                 540
Leu Asp Pro Arg Arg Glu Gly Gly Asp Gln Arg Val Lys Ser Val Ile
545                 550                 555                 560
Asn Leu Leu Phe Ala Ala Tyr Thr Gly Asp Val Ser Ala Leu Arg Arg
                565                 570                 575
Phe Ala Leu Ser Ala Met Asp Met Glu Gln Arg Asp Tyr Asp Ser Arg
                580                 585                 590
Thr Ala Leu His Val Ala Ala Ala Glu Gly His Val Glu Val Val Lys
            595                 600                 605
Phe Leu Leu Glu Ala Cys Lys Val Asn Pro Phe Pro Lys Asp Arg Trp
    610                 615                 620
```

Asn Asn Thr Pro Met Asp Glu Ala Leu His Phe Gly His His Asp Val
625                 630                 635                 640

Phe Lys Ile Leu Gln Glu Tyr Gln Val Gln Tyr Thr Pro Gln Gly Asp
            645                 650                 655

Ser Asp Asp Gly Lys Glu Asn Gln Thr Val His Lys Asn Leu Asp Gly
            660                 665                 670

Leu Leu

<210> SEQ ID NO 14
<211> LENGTH: 287
<212> TYPE: PRT
<213> ORGANISM: Artificial
<220> FEATURE:
<223> OTHER INFORMATION: Wild-type pfam04960 domain consensus sequence
<220> FEATURE:
<221> NAME/KEY: MISC_FEATURE
<222> LOCATION: (32)..(32)
<223> OTHER INFORMATION: X at position 32 is I or T

<400> SEQUENCE: 14

Gly Lys Val Ala Asp Tyr Ile Pro Gln Leu Ala Lys Phe Ser Pro Asp
1               5                   10                  15

Leu Trp Gly Val Ser Val Cys Thr Val Asp Gly Gln Arg His Ser Xaa
            20                  25                  30

Gly Asp Thr Lys Val Pro Phe Cys Leu Gln Ser Cys Val Lys Pro Leu
            35                  40                  45

Lys Tyr Ala Ile Ala Val Asn Asp Leu Gly Thr Glu Tyr Val His Arg
50                  55                  60

Tyr Val Gly Lys Glu Pro Ser Gly Leu Arg Phe Asn Lys Leu Phe Leu
65                  70                  75                  80

Asn Glu Asp Asp Lys Pro His Asn Pro Met Val Asn Ala Gly Ala Ile
                85                  90                  95

Val Val Thr Ser Leu Ile Lys Gln Gly Val Asn Asn Ala Glu Lys Phe
            100                 105                 110

Asp Tyr Val Met Gln Phe Leu Asn Lys Met Ala Gly Asn Glu Tyr Val
        115                 120                 125

Gly Phe Ser Asn Ala Thr Phe Gln Ser Glu Arg Glu Ser Gly Asp Arg
130                 135                 140

Asn Phe Ala Ile Gly Tyr Tyr Leu Lys Glu Lys Lys Cys Phe Pro Glu
145                 150                 155                 160

Gly Thr Asp Met Val Gly Ile Leu Asp Phe Tyr Phe Gln Leu Cys Ser
                165                 170                 175

Ile Glu Val Thr Cys Glu Ser Ala Ser Val Met Ala Ala Thr Leu Ala
            180                 185                 190

Asn Gly Gly Phe Cys Pro Ile Thr Gly Glu Arg Val Leu Ser Pro Glu
        195                 200                 205

Ala Val Arg Asn Thr Leu Ser Leu Met His Ser Cys Gly Met Tyr Asp
210                 215                 220

Phe Ser Gly Gln Phe Ala Phe His Val Gly Leu Pro Ala Lys Ser Gly
225                 230                 235                 240

Val Ala Gly Gly Ile Leu Leu Val Val Pro Asn Val Met Gly Met Met
                245                 250                 255

Cys Trp Ser Pro Pro Leu Asp Lys Met Gly Asn Ser Val Lys Gly Ile
            260                 265                 270

His Phe Cys His Asp Leu Val Ser Leu Cys Asn Phe His Asn Tyr
        275                 280                 285

<210> SEQ ID NO 15
<211> LENGTH: 287
<212> TYPE: PRT
<213> ORGANISM: Artificial
<220> FEATURE:
<223> OTHER INFORMATION: pfam04960 domain consensus sequence with F79W substitution
<220> FEATURE:
<221> NAME/KEY: MISC_FEATURE
<222> LOCATION: (32)..(32)
<223> OTHER INFORMATION: X at position 32 is I or T

<400> SEQUENCE: 15

```
Gly Lys Val Ala Asp Tyr Ile Pro Gln Leu Ala Lys Phe Ser Pro Asp
1               5                   10                  15

Leu Trp Gly Val Ser Val Cys Thr Val Asp Gly Gln Arg His Ser Xaa
                20                  25                  30

Gly Asp Thr Lys Val Pro Phe Cys Leu Gln Ser Cys Val Lys Pro Leu
            35                  40                  45

Lys Tyr Ala Ile Ala Val Asn Asp Leu Gly Thr Glu Tyr Val His Arg
50                  55                  60

Tyr Val Gly Lys Glu Pro Ser Gly Leu Arg Phe Asn Lys Leu Trp Leu
65                  70                  75                  80

Asn Glu Asp Asp Lys Pro His Asn Pro Met Val Asn Ala Gly Ala Ile
                85                  90                  95

Val Val Thr Ser Leu Ile Lys Gln Gly Val Asn Ala Glu Lys Phe
            100                 105                 110

Asp Tyr Val Met Gln Phe Leu Asn Lys Met Ala Gly Asn Glu Tyr Val
115                 120                 125

Gly Phe Ser Asn Ala Thr Phe Gln Ser Glu Arg Glu Ser Gly Asp Arg
130                 135                 140

Asn Phe Ala Ile Gly Tyr Tyr Leu Lys Glu Lys Cys Phe Pro Glu
145                 150                 155                 160

Gly Thr Asp Met Val Gly Ile Leu Asp Phe Tyr Phe Gln Leu Cys Ser
                165                 170                 175

Ile Glu Val Thr Cys Glu Ser Ala Ser Val Met Ala Ala Thr Leu Ala
            180                 185                 190

Asn Gly Gly Phe Cys Pro Ile Thr Gly Glu Arg Val Leu Ser Pro Glu
        195                 200                 205

Ala Val Arg Asn Thr Leu Ser Leu Met His Ser Cys Gly Met Tyr Asp
210                 215                 220

Phe Ser Gly Gln Phe Ala Phe His Val Gly Leu Pro Ala Lys Ser Gly
225                 230                 235                 240

Val Ala Gly Gly Ile Leu Leu Val Val Pro Asn Val Met Gly Met Met
                245                 250                 255

Cys Trp Ser Pro Pro Leu Asp Lys Met Gly Asn Ser Val Lys Gly Ile
            260                 265                 270

His Phe Cys His Asp Leu Val Ser Leu Cys Asn Phe Asn Tyr
        275                 280                 285
```

<210> SEQ ID NO 16
<211> LENGTH: 12
<212> TYPE: PRT
<213> ORGANISM: Artificial
<220> FEATURE:
<223> OTHER INFORMATION: GLS activation loop with F12W substitution

<400> SEQUENCE: 16

```
Lys Glu Pro Ser Gly Leu Arg Phe Asn Lys Leu Trp
1               5                   10

<210> SEQ ID NO 17
<211> LENGTH: 7
<212> TYPE: PRT
<213> ORGANISM: Artificial
<220> FEATURE:
<223> OTHER INFORMATION: peptide fragment

<400> SEQUENCE: 17

Gly Leu Arg Phe Asn Lys Leu
1               5
```